(12) United States Patent
Gonzalez et al.

(10) Patent No.: US 11,781,120 B2
(45) Date of Patent: Oct. 10, 2023

(54) BIOSYNTHESIS OF POLYKETIDES

(71) Applicant: Ramon Gonzalez, Tampa, FL (US)

(72) Inventors: Ramon Gonzalez, Tampa, FL (US);
Seokjung Cheong, Houston, TX (US);
James M. Clomburg, Houston, TX (US)

(73) Assignee: Ramon Gonzalez, Tampa, FL (US)

( * ) Notice: Subject to any disclaimer, the term of this patent is extended or adjusted under 35 U.S.C. 154(b) by 120 days.

(21) Appl. No.: 16/930,220

(22) Filed: Jul. 15, 2020

(65) Prior Publication Data

US 2021/0054427 A1    Feb. 25, 2021

Related U.S. Application Data

(63) Continuation-in-part of application No. 15/749,000, filed as application No. PCT/US2016/045037 on Aug. 1, 2016, now abandoned.

(60) Provisional application No. 62/198,764, filed on Jul. 30, 2015.

(51) Int. Cl.
*C12N 9/10* (2006.01)
*C12P 15/00* (2006.01)
*C12P 17/06* (2006.01)

(52) U.S. Cl.
CPC ............ *C12N 9/1025* (2013.01); *C12P 17/06* (2013.01); *C12Y 203/01174* (2013.01)

(58) Field of Classification Search
CPC .............................. C12N 9/1025; C12P 17/06
See application file for complete search history.

(56) References Cited

PUBLICATIONS

Tan. A polyketoacyl-CoA thiolase-dependent pathway for the synthesis of polyketide backbones. Nat Catal 3, 593-603 (2020).*

* cited by examiner

*Primary Examiner* — Yong D Pak
(74) *Attorney, Agent, or Firm* — Boulware & Valoir, PLLC

(57) ABSTRACT

This disclosure generally relates to the use of microorganisms to make various functionalized polyketides through polyketoacyl-CoA thiolase-catalyzed non-decarboxylative condensation reactions instead of decarboxylative reactions catalyzed by polyketide synthases. Native or engineered polyketoacyl-CoA thiolases catalyze the non-decarboxylative Claisen condensation in an iterative manner (i.e. multiple rounds) between two either unsubstituted or functionalized ketoacyl-CoAs (and polyketoacyl-CoAs) serving as the primers and acyl-CoAs serving as the extender unit to generate (and elongate) polyketoacyl-CoAs. Before the next round of polyketoacyl-CoA thiolase reaction, the β-keto group of the polyketide chain of polyketoacyl-CoA can be reduced and modified step-wise by 3-OH-polyketoacyl-CoA dehydrogenase or polyketoenoyl-CoA hydratase or polyketoenoyl-CoA reductase. Dehydrogenase converts the β-keto group to β-hydroxy group. Hydratase converts the β-hydroxy group to α-β-double-bond. Reductase converts the α-β-double-bond to single bond. Spontaneous or thioesterase catalyzed termination reaction terminates the elongation of polyketide chain of polyketoacyl-CoA at any point through CoA removal and spontaneous reactions rearrange the structure, generating the final functional polyketide products.

13 Claims, 21 Drawing Sheets

Specification includes a Sequence Listing.

Geldanamycin

Doxycycline

Erythromycin

SEQUENCE LISTING

<160> NUMBER OF SEQ ID NOS: 1

<210> SEQ ID NO 1
<211> LENGTH: 36
<212> TYPE: DNA
<213> ORGANISM: Artificial Sequence
<220> FEATURE:
<223> OTHER INFORMATION: Synthetic primer: ppfadA-f1

<400> SEQUENCE: 1
gccaggatcc gaattcgagc ctgaatccgc gtgatg                36

BIOSYNTHESIS OF POLYKETIDES

PRIOR RELATED APPLICATIONS

This application claims priority to and is a Continuation-in-Part of U.S. Ser. No. 15/749,000, filed Jan. 30, 2018, which claims priority to PCT/US16/45037, filed Aug. 1, 2016, which claims priority to U.S. Ser. No. 62/198,764, filed Jul. 30, 2015, each is incorporated by reference herein in its entirety for all purposes.

FEDERALLY SPONSORED RESEARCH STATEMENT

Not applicable.

FIELD OF THE DISCLOSURE

This disclosure generally relates to the use of microorganisms or their enzymes to make various functionalized polyketides through iterative, non-decarboxylative condensation reactions catalyzed by native or engineered thiolases, herein referred to as polyketoacyl-CoA thiolases, instead of decarboxylative reactions catalyzed by polyketide synthases.

BACKGROUND OF THE DISCLOSURE

Polyketides are a class of secondary metabolites produced by certain living organisms in order to impart to them some survival advantage. Structurally, polyketides are complex organic compounds that are often highly active biologically, and are characterized by having a plurality of carbonyl groups (ketones). Many pharmaceuticals are derived from or inspired by polyketides. Exemplary polyketides include the antibiotics geldanamycin, doxycycline, and erythromycin (FIG. 1). Such polyketides can also be prenylated, to form derivative such as olivetol, also known as 5-pentylresorcinol (FIG. 2).

Polyketides are broadly divided into three classes: type I polyketides (often macrolides produced by multimodular megasynthases), type II polyketides (often aromatic molecules produced by the iterative action of dissociated enzymes), and type III polyketides (often small aromatic molecules produced by fungal species). Polyketide antibiotics, antifungals, cytostatics, anticholesteremic, antiparasitics, coccidiostats, animal growth promoters and natural insecticides are all in commercial use, illustrating the importance of this class of compounds.

Natural polyketide biosynthesis pathways utilize decarboxylative Claisen condensation reactions with malonyl-CoA thioesters as extender units. These pathways synthesize various polyketides with diverse chain lengths, structures and functionalities. This diversity is achieved by using functionalized primers, α-functionalized malonyl thioesters as extender units, and an array of pathways for termination of carbon chain elongation and subsequent product modification.

Despite the structural and functional diversity of these products, the use of malonyl-CoA thioester as the two-carbon extender unit requires the ATP-dependent activation of acetyl-CoA to malonyl-CoA, which in turn limits the energy efficiency of these pathways. Furthermore, owing to the decarboxylative nature of the condensation reaction, the β site of the extender units of the decarboxylative Claisen condensation must be a carboxylic group, restricting the range of extender units and potentially limiting the diversity of products that can be generated through these carbon chain elongation pathways.

Methods of overcoming the low energy efficiencies of these pathways as well as means of varying the extender unit are thus needed to increase the polyketides available as sources of therapeutics and feedstocks. This invention addresses one or more of those needs.

SUMMARY OF THE DISCLOSURE

In wild type bacteria, all polyketides are assembled by successive rounds of decarboxylative Claisen condensations between a thioesterified malonate derivative and an acyl thioester. The enzyme that catalyzes these condensations is a "polyketide synthase" or "PKS."

All PKSs catalyze condensation reactions between an activated carboxylic acid (e.g. acetyl-CoA, which is the activated form of acetate) and an activated dicarboxylic acid (e.g. malonyl-CoA, which is the activated form of malonate). These condensation reactions take place through a decarboxylative Claisen condensation mechanism in which the activated carboxylic acid (e.g. acetyl-CoA) serves as "starter" or "primer" and the activated dicarboxylic acid (e.g. malonyl-CoA) serves as "extender" unit. This reaction involves the decarboxylation of the extender and results in the formation of a di- or polyketide that is two carbons longer than the starter.

In order to overcome the inherently low ATP efficiency of natural polyketide synthesis pathways and further diversify the range of extender units, this disclosure demonstrates a general CoA-dependent polyketide synthesis and elongation platform based on the use of polyketoacyl-CoA thiolase-catalyzed non-decarboxylative Claisen condensation that accepts ketoacyl-CoA or polyketoacyl-CoA thioesters as primers and acetyl-CoA (or acetyl-CoA derivatives) as extender units to form a longer polyketoacyl-CoA. This reaction can be repeated as many times as desired to keep adding keto groups to the growing polyketide.

Wide-ranging product diversity (FIG. 3-4) from this iterative platform is achieved through the use of primers with omega-functionalization ($R_1$ in FIG. 3-4) and extender units with omega-functionalization ($R_2$ in FIG. 3-4) in combination with various degrees of keto group reductions. The proposed platform possesses the potential for both the high product diversity of a biosynthetic pathway combined and the high efficiency of a fermentative pathway.

Our novel pathway for the synthesis of polyketides is completely different/orthogonal to any polyketide biosynthesis pathway reported in the patent or peer-reviewed literature (and more efficient). The key features of the pathway are:

1) It proceeds through a non-decarboxylative Claisen condensation mechanism instead of a decarboxylative one.

2) It uses activated carboxylic acids (e.g. acetyl-CoA) as extender units instead of activated dicarboxylic acids (e.g. malonyl-CoA) used by PKS-based pathways;

3) It uses polyketoacyl-CoA thiolases instead of PKSs; these two types of enzymes have different structure and sequence (and are encoded by different/unrelated genes) and catalyze reactions that involve different reactants and products and use different reaction mechanisms (see "1)" and 2)" above).

Therefore, the new pathway is based on a different reaction mechanism, different reactants and products, and different enzymes/genes than those previously reported for polyketides.

The new pathway is based on native or engineered polyketoacyl-CoA thiolases capable of catalyzing the condensation between ketoacyl-CoA or polyketoacyl-CoA thioesters, which serve as the initiating primers, and acetyl-CoA (or acetyl-CoA derivatives), which serves as the extender units. These thiolases catalyze the non-decarboxylative Claisen condensation in an iterative manner (i.e. multiple rounds of the addition cycle) between two either unsubstituted or omega-functionalized primer and extender units to generate and elongate polyketoacyl-CoAs.

If desired, a particular keto group can be reduced and modified step-wise by 3-OH-polyketoacyl-CoA dehydrogenase or polyketoenoyl-CoA hydratase or polyketoenoyl-CoA reductase. 3-OH-polyketoacyl-CoA dehydrogenase converts the β-keto group to β-hydroxy group. Polyketoenoyl-CoA hydratase converts the β-hydroxy group to α-β-double-bond. Polyketoenoyl-CoA reductase converts the α-β-double-bond to single bond.

At any point, the polyketide can be released and isolated. Spontaneous or thioesterase catalyzed termination reaction terminates the elongation of polyketide chain at any point through CoA removal and spontaneous reactions rearrange the structure, for example through ring closure/cyclization, generating the final functional polyketide products.

The process involves performing traditional fermentations using industrial organisms (e.g., *E. coli, B. subtillus, S. cerevisiae* and the like) that convert different feedstocks into longer-chain polyketides. Media preparation, sterilization, inoculum preparation, and fermentation are the main steps of the process.

The microorganisms can be used as living chemical manufacturing systems, or can be harvested and the bacteria used as bioreactors for as long as the enzymes remain functional in the non-growing cells. Alternatively, the enzymes can be purified and used in an in vitro system reconstituted from the purified enzymes. Such an embodiment may be preferred as allowing the most control over the synthesis of complicated polyketides. However, living systems may be preferred as allowing continuous production and would be suitable for simple polyketides or polyketide precursors for downstream products.

The pathways in a living system are generally made by transforming the microbe with an expression vector encoding one or more of the proteins, but the genes can also be added to the chromosome by recombineering, homologous recombination, and similar techniques. Where the needed protein is endogenous, as is the case in some instances, it may suffice as is, but it is usually overexpressed using an inducible promoter for better functionality and user-control over the level of active enzyme.

Reference to proteins herein can be understood to include reference to the gene encoding such protein. Thus, a claimed "permease" protein can include the related gene encoding that permease. However, it is preferred herein to refer to the protein by standard name per ecoliwiki.net or Human Genome Organisation (HUGO) since both enzymatic and gene names have varied widely, especially in the prokaryotic arts.

Once an exemplary protein is obtained, many additional examples of proteins with similar activity can be identified by BLAST search. Further, every protein record is linked to a gene record, making it easy to design overexpression vectors. Many of the needed enzymes are already available in vectors, and can often be obtained from cell depositories or from the researchers who cloned them. But, if necessary, new clones can be prepared based on available sequence information using e.g., RT-PCR techniques. Thus, it should be easily possible to obtain all of the needed enzymes for overexpression.

Another way of finding suitable enzymes/proteins for use in the invention is to consider other enzymes with the same EC number, since these numbers are assigned based on the reactions performed by a given enzyme. An enzyme that thus be obtained, e.g., from AddGene.org or from the author of the work describing that enzyme, and tested for functionality as described herein. In addition, many sites provide lists of proteins that all catalyze the same reaction.

Understanding the inherent degeneracy of the genetic code allows one of ordinary skill in the art to design multiple nucleotides that encode the same amino acid sequence. NCBI™ provides codon usage databases for optimizing DNA sequences for protein expression in various species. Using such databases, a gene or cDNA may be "optimized" for expression in *E. coli*, yeast, algal or other species using the codon bias for the species in which the gene will be expressed.

Initial cloning experiments have proceeded in *E. coli* for convenience since most of the required genes are already available in plasmids suitable for bacterial expression, but the addition of genes to bacteria is of nearly universal applicability. Indeed, since recombinant methods were invented in the 70's and are now so commonplace, even school children perform genetic engineering experiments using bacteria. Such species include e.g., *Bacillus, Streptomyces, Azotobacter, Trichoderma, Rhizobium, Pseudomonas, Micrococcus, Nitrobacter, Proteus, Lactobacillus, Pediococcus, Lactococcus, Salmonella, Streptococcus, Paracoccus, Methanosarcina,* and *Methylococcus*, or any of the completely sequenced bacterial species. Indeed, hundreds of bacterial genomes have been completely sequenced, and this information greatly simplifies both the generation of vectors encoding the needed genes, as well as the planning of a recombinant engineering protocol. Such species are listed along with links at en.wikipedia.org/wiki/List of sequenced bacterial genomes.

Additionally, yeast, such as *Saccharomyces*, are a common species used for microbial manufacturing, and many species can be successfully transformed. Indeed, yeast are already available that express recombinant thioesterases—one of the termination enzymes described herein—and the reverse beta oxidation pathway has also been achieved in yeast. Other species include but are not limited to *Candida, Aspergillus*, Arxula adeninivorans, *Candida boidinii, Hansenula polymorpha (Pichia angusta), Kluyveromyces lactis, Pichia pastoris,* and *Yarrowia lipolytica*, to name a few.

It is also possible to genetically modify many species of algae, including e.g., *Spirulina, Apergillus, Chlamydomonas, Laminaria japonica, Undaria pinnatifida, Porphyra, Eucheuma, Kappaphycus, Gracilaria, Monostroma, Enteromorpha, Arthrospira, Chlorella, Dunaliella, Aphanizomenon, Isochrysis, Pavlova, Phaeodactylum, Ulkenia, Haematococcus, Chaetoceros, Nannochloropsis, Skeletonema, Thalassiosira,* and *Laminaria japonica*. Indeed, the microalga *Pavlova lutheri* is already being used as a source of economically valuable docosahexaenoic (DHA) and eicosapentaenoic acids (EPA), and *Crypthecodinium cohnii* is the heterotrophic algal species that is currently used to produce the DHA used in many infant formulas.

Furthermore, a number of databases include vector information and/or a repository of vectors and can be used to choose vectors suitable for the chosen host species. See, for example, AddGene.org, which provides both a repository and a searchable database allowing vectors to be easily located and obtained from colleagues. See also Plasmid Information Database (plasmid.med.harvard.edu) and DNA-SU.org having over 191,000 plasmids. A collection of cloning vectors of *E. coli* is also kept at the National Institute of Genetics as a resource for the biological research community.

The enzymes can be added to the genome or via expression vectors, as desired. Preferably, multiple enzymes are expressed in one vector or multiple enzymes can be combined into one operon by adding the needed signals between coding regions. Further improvements can be had by over-expressing one or more, or even all of the enzymes, e.g., by adding extra copies to the cell via plasmid or other vector. Initial experiments may employ expression plasmids hosting multigene operons or 2 or more open reading frames (ORFs) encoding the needed genes for convenience, but it may be preferred to insert operons or individual genes into the genome for long term stability.

Still further improvements in yield can be had by reducing competing pathways, such as those pathways for making e.g., acetate, formate, ethanol, and lactate, and it is already well known in the art how to reduce or knockout these pathways. See for example, the Rice patent portfolio by Ka-Yiu San and George Bennett (U.S. Pat. Nos. 7,569,380, 7,262,046, 8,962,272, 8,795,991) and patents by these inventors (U.S. Pat. Nos. 8,129,157 and 8,691,552) (each incorporated by reference herein in its entirety for all purposes).

As used herein, "homolog" means an enzyme with at least 40% identity to one of the listed sequences and also having the same general catalytic activity, although kinetic parameters can of course vary. While higher identity (60%, 70%, 80%) and the like may be preferred, it is typical for bacterial sequences to diverge significantly (40-60%), yet still be identifiable as homologs, while mammalian species tend to diverge less (80-90%).

As used herein, a "primer" is a starting molecule for the iterative cycle to add multiple-carbon extender units to a growing ketoacyl-CoA or polyketoacyl-CoA. The "initial primer" or "initiating primer" is typically acetoacetyl-CoA, a ketoacyl-CoA, but as the chain grows by adding extender units in each cycle, the primer will accordingly increase in size (e.g. condensation of acetoacetyl-CoA and acetyl-CoA generates 3,5-diketohexanoyl-CoA, which can be used as primer in the following iteration). In this application, the beta-keto acyl from one round of condensation is immediately condensed with the next extender unit, adding another two carbons, including a carbonyl. Additionally, non-traditional primers can also be used in which the terminal omega carbon has been functionalized (i.e., omega-hydroxylated, omega-carboxylated, etc.).

In some cases, the bacteria can also be provided with larger primers, e.g., C4 primers, etc. added to the media or obtained from other cell pathways. In addition, the beta-keto group created during the condensation can be further reduced and modified step-wise by dehydrogenase or hydratase or reductase, thus generating different primers. Such primers may be endogenous, and if not, can be added to the cell media, or an enzyme pathway to make same can be provided.

Note that the term "omega" refers to the last carbon, the first being linked to the -CoA group, and this terminology is retained even once the CoA has been hydrolyzed off the growing polyketide.

As used herein, the "extender unit" is acetyl-CoA or acetyl-CoA derivatives that react with the primer in iterative condensations to add carbons on the polyketide chain. In biological systems, the extender unit is typically acetyl-CoA. One aspect of the disclosed methods is the use of non-traditional extender units in which the terminal omega carbon has been functionalized (i.e., omega-hydroxylated extender unit, omega-carboxylated extender unit, etc. . . . ). Of course, the polyketoacyl-CoA thiolase selected for over-expression must be able to accept and act on the omega-functionalized extender unit.

As used herein, "ketoacyl-CoA" is an acyl-CoA with a keto group at the acyl group chain.

As used herein, "polyketoacyl-CoA" is an acyl-CoA with more than one keto group at the acyl group chain.

As used herein, "ketoacyl-CoA thiolase", also called "thiolase I" (EC 2.3.1.16) is an enzyme that mainly degrades a ketoacyl-CoA to two acyl-CoAs without keto groups. It also catalyzes the non-decarboxylative Claisen condensation between two acyl-CoAs, one serving as the primer and the other serving as the extender unit, to form a ketoacyl-CoA, the reverse of its degradation reaction. The forward and reverse reactions are shown below:

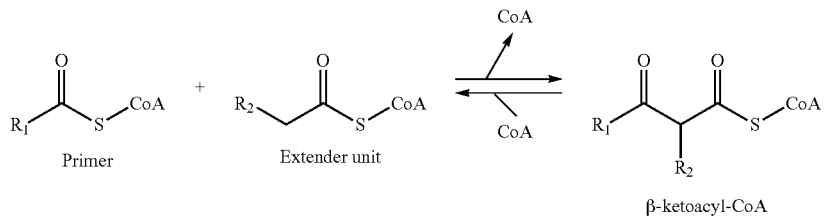

As used herein, "acetoacetyl-CoA thiolase", also called "thiolase II" (EC 2.3.1.9), is an enzyme that mainly catalyzes the non-decarboxylative Claisen condensation between two acetyl-CoAs, one serving as the primer and the other serving as the extender unit, to form an acetoacetyl-CoA. The reaction is shown below:

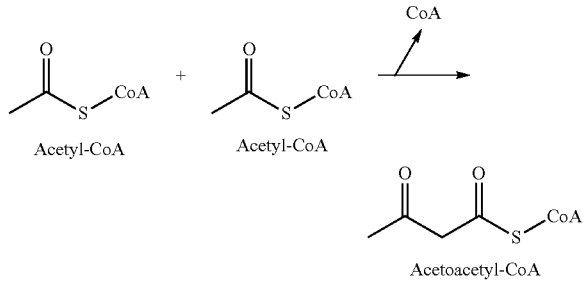

There are many known examples of TYPE II thiolases, including P76461, ATOB_ECOLI; P44873, ATOB_HAEIN;

Q9I2A8, ATOB_PSEAE; Q0KBP1, BKTB_CUPNH; P66927, FADA4_MYCBO; P46707, FADA4_MYCLE; A0R1Y7, FADA4_MYCS2; P9WG68, FADA4_MYCTO; P9WG69, FADA4_MYCTU; Q12598, THIA_CANTR; Q04677, THIB_CANTR; Q8S4Y1, THIC1_ARATH; Q9FIK7, THIC2_ARATH; Q9BWD1, THIC_HUMAN; Q8CAY6, THIC_MOUSE; Q5XI22, THIC_RAT; Q86AD9, THIL1_DICDI; Q6NU46, THILA_XENLA; Q6GN02, THILB_XENLA; P45369, THIL_ALLVD; Q29RZ0, THIL_BOVIN; Q9ZHI1, THIL_CHRVO; P14611, THIL_CUPNH; Q6AZA0, THIL_DANRE; P24752, THIL_HUMAN; Q8HXY6, THIL_MACFA; Q8QZT1, THIL_MOUSE; P54810, THIL_PARDE; P14610, THIL_PIG; P17764, THIL_RAT; P50174, THIL_RHIME; P10551, THIL_SACMO; Q9UQW6, THIL_SCPO; P45363, THIL_THIVI; Q5BKN8, THIL_XENTR; Q6L8K7, THIL_YARLI; P41338, THIL_YEAST; P07097, THIL_ZOORA; P45359, THLA_CLOAB; Q18AR0, THLA_PEPD6; Q2FJQ9, THLA_STAA3; Q2G124, THLA_STAA8; Q2YVF5, THLA_STAAB; Q5HIU0, THLA_STAAC; Q99WM3, THLA_STAAM; Q7A7L2, THLA_STAAN; Q6GJW4, THLA_STAAR; Q6GCB8, THLA_STAAS; Q8NY95, THLA_STAAW; Q5HS07, THLA_STAEQ; Q8CQN7, THLA_STAES; P45855, THL_BACSU; P81347, THL_CLOPA; P45362, THL_PEPDI; Q46939, YQEF_ECOLI.

As used herein, "polyketoacyl-CoA thiolase," (EC 2.3.1.—(EC number not yet assigned)) is an enzyme that catalyzes the non-decarboxylative Claisen condensation between a ketoacyl-CoA or a polyketoacyl-CoA primer and acetyl-CoA (or acetyl-CoA derivative) as the extender unit to form a polyketoacyl-CoA. The reaction is shown below with n being >zero<30, or less than 25, 20, or preferably 4-18, 6-16, or integer therebetween:

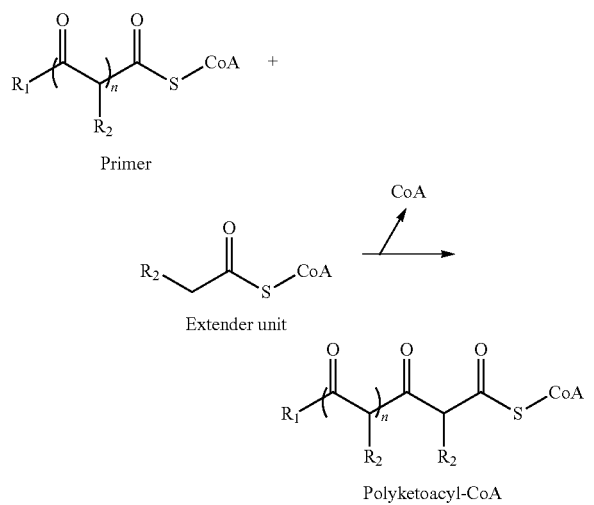

We have identified a few of such enzymes herein, and have provided a number of different screening methods for identifying additional members of this family, or members can be identified by homology to those described herein. Further, although not all thiolases can function as polyketoacyl-CoA thiolases (e.g., AtoB), some of them can, and thus each of the genes above can be tested for polyketoacyl-CoA thiolase activity.

This reaction can be repeated as many times as needed, with each iteration adding another ketone to the growing polyketoacyl-CoA chain.

In preferred embodiments, the same thiolase can catalyzes ketoacyl-CoA forming and polyketoacyl-CoA forming reactions.

As used herein, a "3-OH-polyketoacyl-CoA dehydrogenase" is an enzyme that catalyzes the reduction of the β-keto group of a polyketoacyl-CoA to a β-hydroxy group as shown in the reaction below (n below is larger than zero):

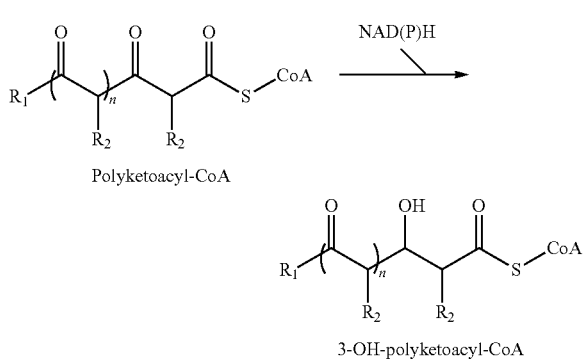

As used herein, "3-OH-polyketoacyl-CoA" is the acyl-CoA generated from polyketoacyl-CoA after dehydrogenation reaction catalyzed by 3-OH-polyketoacyl-CoA dehydrogenase.

As used herein, "polyketoenoyl-CoA hydratase (ECH)" is an enzyme that catalyzes the dehydration of a β-hydroxy group of a 3-OH-polyketoacyl-CoA to an α,β double bond as shown in the reaction below (n below is larger than zero):

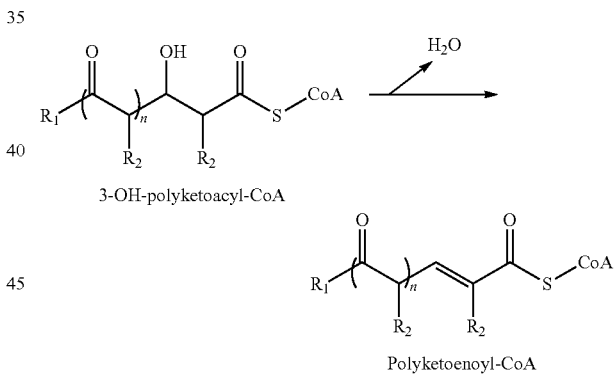

As used herein, a "polyketoenoyl-CoA" is the acyl-CoA generated from 3-OH-polyketoacyl-CoA after the dehydration reaction catalyzed by polyketoenoyl-CoA hydratase.

As used herein, a "polyketoenoyl-CoA reductase (ECR)" is an enzyme that catalyzes the reduction of an α,β double bond of a polyketoenoyl-CoA to a α,β single bond as shown in the reaction below (n below is larger than zero):

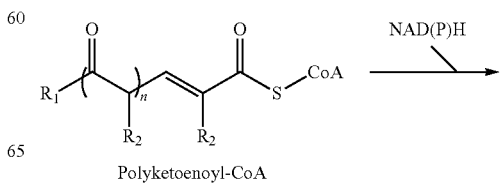

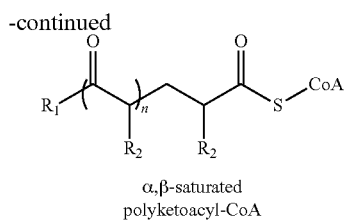

α,β-saturated
polyketoacyl-CoA

As used herein, an "α,β-saturated polyketoacyl-CoA" is the acyl-CoA generated from polyketoenoyl-CoA after the reduction reaction catalyzed by polyketoenoyl-CoA reductase.

3-OH-polyketoacyl-CoA, polyketoenoyl-CoA and α,β-saturated polyketoacyl-CoA can serve as the primer for polyketoacyl-CoA thiolase catalyzed non-decarboxylative Claisen condensation reaction to add another ketone to the n-reduced polyketide chain.

As used herein, "R1" and "R2" are omega functional groups originating from the omega-functionalized group of extender or primer units. Examples of R1 and R2 groups are as below:

TABLE 1

Examples of R1 and R2 groups

—H
Alkyl
Aryl
—OH
—X
—NH₂
Arylacyl
Hydroxyacyl
Carboxyacyl
Aminoacyl
Ketoacyl
Halongenated acyl
Ester As used herein, "termination reactions" refers to spontaneous or enzyme catalyzed reactions that will pull polyketoacyl-CoA thioester intermediates out the polyketide chain elongation platform and produce the desired end product, or a precursor thereof.

As used herein, "rearrangement" refers to spontaneous reaction of polyketide chain (to form cyclic or aromatic groups) during or after the termination reaction. As one example, diketoacyl-CoA 3,5-dioxohexanoyl-CoA spontaneously releases CoA and cyclizes to produce TAL. A polyketide can also be released with a thioesterase.

As used herein, references to cells or bacteria or strains and all such similar designations include progeny thereof. It is also understood that all progeny may not be precisely identical in DNA content, due to deliberate or inadvertent mutations that have been added to the parent. Mutant progeny that have the same function or biological activity as screened for in the originally transformed cell are included. Where distinct designations are intended, it will be clear from the context.

The terms "operably associated" or "operably linked," as used herein, refer to functionally coupled nucleic acid sequences.

As used herein "recombinant" or "engineered" is relating to, derived from, or containing genetically engineered material. In other words, the genome was intentionally manipulated in some way.

"Reduced activity" or "inactivation" (indicated by "-") is defined herein to be at least a 75% reduction in protein activity, as compared with an appropriate control species. Preferably, at least 80, 85, 90, 95% reduction in activity is attained, and in the most preferred embodiment, the activity is eliminated (100%, aka a "knock-out" or "null" mutants, indicated by Δ). Proteins can be inactivated with inhibitors, by mutation, or by suppression of expression or translation, and the like. Use of a frame shift mutation, early stop codon, point mutations of critical residues, or deletions or insertions, and the like, can completely inactivate (100%) gene product by completely preventing transcription and/or translation of active protein.

"Overexpression" or "overexpressed" (indicated by "+") is defined herein to be at least 150% of protein activity as compared with an appropriate control species, and preferably 200, 500, 1000%) or more, or any activity in a host that would otherwise lack that enzyme. Overexpression can be achieved by mutating the protein to produce a more active form or a form that is resistant to inhibition, by removing inhibitors, or adding activators, and the like. Overexpression can also be achieved by removing repressors, adding multiple copies of the gene to the cell, or upregulating the endogenous gene, and the like.

The term "endogenous" or "native" means that a gene originated from the species in question, without regard to subspecies or strain, although that gene may be naturally or intentionally mutated, or placed under the control of a promoter that results in overexpression or controlled expression of said gene. Thus, genes from Clostridia would not be endogenous to *Escherichia*, but a plasmid expressing a gene from *E. coli* would be considered to be endogenous to any genus of *Escherichia*, even though it may now be overexpressed. By contrast, the term "wild type" means a functional native gene that is not modified from its form in the wild.

"Expression vectors" are used in accordance with the art-accepted definition of a plasmid, virus or other propagatable sequence designed for protein expression in cells. There are thousands of such vectors commercially available, and typically each has an origin of replication (ori); a multiple cloning site; a selectable marker; ribosome binding sites; a promoter and often enhancers; and the needed termination sequences. Most expression vectors are inducible, although constitutive expressions vectors also exist and either can be used.

As used herein, "inducible" means that gene expression can be controlled by the hand-of-man, by adding e.g., a ligand to induce expression from an inducible promoter. Exemplary inducible promoters include the lac operon, inducible by IPTG, the yeast AOX1 promoter inducible with methanol, the strong LAC4 promoter inducible with lactate, and the like. Low level of constitutive protein synthesis may occur even in expression vectors with tightly controlled promoters.

As used herein, an "integrated sequence" means the sequence has been integrated into the host genome, as opposed to being maintained on an expression vector. It will still be expressable, and preferably is inducible as well, although in other cases a strong constitutive promoter may be preferred.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

The phrase "consisting of" is closed, and excludes all additional elements.

The phrase "consisting essentially of" excludes additional material elements, but allows the inclusions of non-material elements that do not substantially change the nature of the invention, such as instructions for use, buffers, background or silent mutations that do not effect the invention, and the like.

The following abbreviations may be used herein:

TABLE 2

Abbreviations

| ABBREVIATION | TERM |
|---|---|
| ACP | Acyl carrier protein |
| ATCC | American Tissue Culture Collection, atcc.org |
| BLAST | Basic Local Alignment Search Tool, ncbi.nlm.nih.gov/blast/ |
| BOX | Beta oxidation pathway |
| BSA | Bovine serum albumin |
| BSTFA | N,O-bis(trimethylsilyl)trifluoroacetamide |
| GC | Gas chromatography |
| HPLC | High pressure liquid chromatography |
| HUGO | Human Genome Organisation, genenames.org |
| ORF | Open reading frame |
| PCR | Polymerase chain reaction |
| RBOX | Reverse BOX |
| RT-PCR | Reverse transcription PCR |
| TAL | triacetic acid lactone |

DETAILED DESCRIPTION

Figure 1:
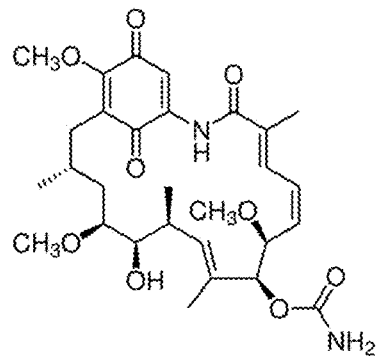
FIG. 1: Biologically important polyketides.
Figure 1:
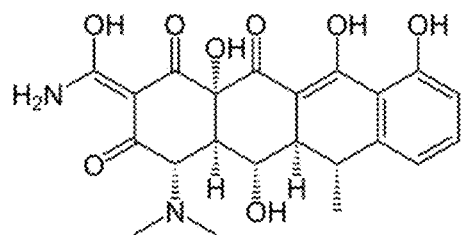
Figure 1:
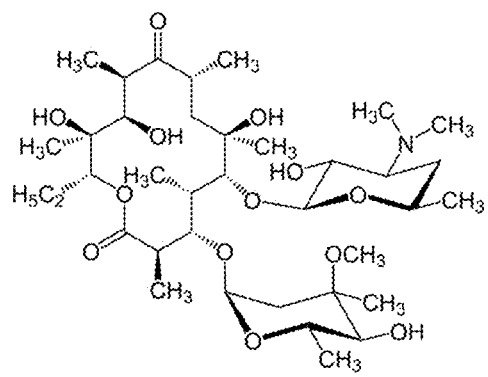
Figure 2:
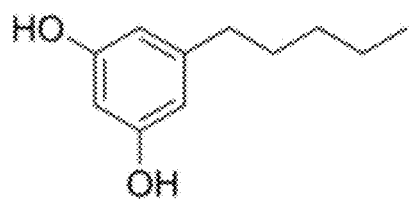
FIG. 2: Olivetol, also known as 5-pentylresorcinol or 5-pentyl-1,3-benzenediol, can be made with the invention, and then prenylated to produce prenylated aromatics (e.g. cannabigerolic acid or CBGA).

This disclosure generally relates to the use of microorganisms to make functionalized polyketides through polyketoacyl-CoA thiolase-catalyzed non-decarboxylative Claisen condensation reactions instead of decarboxylative Claisen condensation reactions catalyzed by polyketide synthases. Native or engineered polyketoacyl-CoA thiolases catalyze the non-decarboxylative Claisen condensation in an iterative manner (i.e. multiple rounds) between either unsubstituted or functionalized ketoacyl-CoAs (and polyketoacyl-CoAs) as primers and acetyl-CoA as extender unit to generate (and elongate) polyketoacyl-CoAs.

If desired, the β-keto group of the polyketide chain of polyketoacyl-CoA can be reduced and modified step-wise by 3-OH-polyketoacyl-CoA dehydrogenase or polyketoenoyl-CoA hydratase or polyketoacyl-CoA reductase. Dehydrogenase converts the β-keto group to β-hydroxy group. Hydratase converts the β-hydroxy group to α-β-double-bond. Reductase convert the α-β-double-bond to single bond. This molecule can then undergo additional rounds of polyketoacyl-CoA thiolase extension, to add on additional keto groups (the last beta keto group having been removed to leave a gap), or an exit to form product.

Spontaneous or thioesterase catalyzed termination reaction terminates the elongation of polyketide chain at any point through CoA removal and spontaneous reactions rearrange the structure, generating the final functional polyketide products, or precursors for further modification.

In more detail, the invention includes any one or more of the following embodiment(s) in any combination(s) thereof:

TABLE 3

Embodiments of the invention

A method of making a polyketide, comprising growing a genetically engineered microorganism in a nutrient broth for a time sufficient to product a polyketide and isolating said polyketide or a spontaneously rearranged form of said polyketide, wherein said microorganism has a polyketide-producing pathway comrprising the following substrate(s) to product(s) conversions:
C(n)-acyl-CoA + acetyl-CoA → C(n+2)-ketoacyl-CoA;
C(n+2)-ketoacyl-CoA + acetyl-CoA → C(n+4)-polyketoacyl-CoA;
iterations of reaction in step b, wherein said iterations are achieved by utilizing the polyketoacyl-CoA generated in step b as a substrate for condensation with acetyl-CoA to elongate the polyketoacyl-CoA chain by two carbons and add a beta-keto group; and
conversion of said polyketoacyl-CoA in steps b or c to a polyketide or a spontaneously rearranged form of said polyketide.

TABLE 3-continued

Embodiments of the invention

A method of making a polyketide, comprising growing a genetically engineered microorganism in
a nutrient broth for a time sufficient to produce a polyketide and isolating said polyketide or a
spontaneously rearranged form of said polyketide, wherein said microorganism has a polyketide-
producing pathway comprising the following substrate(s) to product(s) conversions:
a. C(n)-acyl-CoA + acetyl-CoA → C(n+2)-ketoacyl-CoA;
b. C(n+2)-ketoacyl-CoA + acetyl-CoA → C(n+4)-polyketoacyl-CoA;
c. C(n+4)-polyketoacyl-CoA → 3-OH- C(n+4)-polyketoacyl-CoA;
d. 3-OH- C(n+4)-polyketoacyl-CoA → C+4)-polyketoenoyl-CoA;
e. C(n+4)-polyketoenoyl-CoA→ C(n+4)-α,β-unsaturated-polyketoacyl-CoA;
f. iterations of reactions in steps b, c, d, and e wherein said iterations are achieved by
  utilizing the polyketoacyl-CoAs, 3-OH-polyketoacyl-CoAs, and polyketoenoyl-CoA
  generated in reactions steps b, c, d, and 3 as substrates for condensation with acetyl-CoA
  to elongate said polyketoacyl-CoAs, 3-OH-polyketoacyl-CoAs, polyketoenoyl-CoA, and
  α,β-unsaturated-polyketoacyl-CoA chains by two carbons and add a beta-keto group; and,
g. conversion of said polyketoacyl-CoA in steps b, c, d, e, or f to a polyketide or a
  spontaneously rearranged form of said polyketide.
A method as herein described, wherein the conversion of said C(n)-acyl-CoA and acetyl-CoA into
said C(n+2)-ketoacyl-CoA is catalyzed by a ketoacyl-CoA thiolase.
A method as herein described, wherein the conversion of said C(n+2)-ketoacyl-CoA and acetyl-
CoA into said C(n+4)-polyketoacyl-CoA is catalyzed by polyketoacyl-CoA thiolase.
A method as herein described, wherein the conversion of said polyketoacyl-CoA and acetyl-CoA
into said longer polyketoacyl-CoA is catalyzed by a polyketoacyl-CoA thiolase.
A method as herein described, wherein the conversion of said C(n+4)-polyketoacyl-CoA into said
3-OH-C(n+4)-polyketoacyl-CoA is catalyzed by a 3-OH-polyketoacyl-CoA dehydrogenase.
A method as herein described, wherein the conversion of said 3-OH-C(n+4)-polyketoacyl-CoA into
said C(n+4)-polyketoenoyl-CoA is catalyzed by a 3-OH-polyketoacyl-CoA dehydratase.
A method as herein described, wherein the conversion of said C(n+4)-polyketoenoyl-CoA into said
α,β-unsaturated-polyketoacyl-CoA is catalyzed by a polyketoenoyl-CoA reductase.
A method as herein described, wherein the conversion of said polyketoacyl-CoA, 3-OH-
polyketoacyl-CoA, polyketoenoyl-CoA, or α,β-unsaturated-polyketoacyl-CoA and acetyl-Co into
said longer polyketoacyl-CoA, 3-OH-polyketoacyl-CoA, or polyketoenoyl-CoA is catalyzed by
a polyketoacyl-CoA thiolase.
A method as herein described, wherein the conversion of said polyketoacyl-CoA to a polyketide is
catalyzed by a thioesterase or takes polace spontaneously. Sometimes, the thioesterase is
overexpressed, but in many cases reduced expression is preferred, and it is also known to change
product length by changing length specificity of the thioesterase.
A method of making a polyketide, comprising growing a microorganism in a nutrient broth for a
time sufficient to produce a polyketide or a spontaneous rearrangement form of said polyketide
and isolating said polyketide or said spontaneous rearrangement form of said polyketide,
wherein said microorganism has means for:
a polyketoacyl-CoA thioase catalyzing a non-decarboxylative Claisen condensation between an
acetyl-coA extender unit (or an omega-functionalized variant thereof) and ketoacyl-coA primer
(or an omega-functionalized variant thereof) to form a polyketoacyl-CoA (or an ometa-
functionalized variant thereof);
optional iterations of step i, wherein said polyketoacyl-CoA is the primer in said iteration to produce
a polyketoacyl-CoA that is two carbons longer;
converting said polyketoacyl-CoA to a polyketide or a spontaneous rearrangement form of said
polyketide.
A method of making polyketides, comprising:
combining a polyketoacyl-CoA thiolase with a keto-acyl primer and an acetyl-coA extender unit to
make a polyketoacyl-CoA, wherein said polyketoacyl-CoA thiolase catalyzes the following reaction
and its iterations:

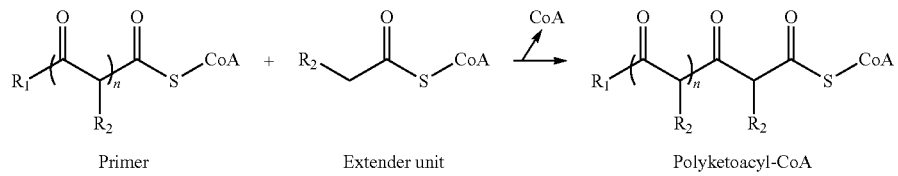

Primer                    Extender unit                    Polyketoacyl-CoA wherein R1 and R1 can independently or both be Alkyl, Aryl, —OH, —NH2, —H, —X Arylacyl,
Hydroxyacyl, Carboxyacyl, Aminoacyl, Ketoacyl, Halongenated acyl, or Ester; releasing a
polyketide or a spontaneous rearrangement form of said polyketide and free coA from said
polyketoacyl-CoA by a thioesterase or by spontaneous hydrolysis; and
isolating said polyketide or said spontaneous rearrangement form of said polyketide.
A method as herein described, wherein said polyketoacyl-CoA thiolase is encoded by a gene(s)
selected from the group consisting of Rhodococcus opacus pcaF, Pseudomonas putida, pcaF,
Streptomyces sp. pcaF, P. putida fadAx, P. putida fadA, Acinetobacter sp. ADP1 dcaF and
Ralstonia eutropha bktB. Homologs with the same catalytic activity can also be used, and in
certain embodiments, the polyketoacyl-CoA tholase is overexpressed.
A method, comprising:
conbining a polyketoacyl-CoA thiolase with acetyl-CoA under conditions sufficient to allow said
polyketoacyl-CoA thiolase to perform non-decarboxylative Claisen condensations with said acetyl-
CoA to form a polyketoacyl-CoA;

TABLE 3-continued

Embodiments of the invention hydrolyzing said polyketoacyl-CoA to form polyketide or a spontaneous rearrangement form of said polyketide and free Co-A; and
isolating said polyketide or said spontaneous rearrangement form of said polyketide.
A method as herein described, wherein said method is performed in vivo using a genetically engineered microorganism that overexpresses said polyketoacyl-CoA thiolase. Alternatively, said method is performed in vitro using purified polyketoacyl-CoA thiolase. In some embodiments, the acetyl-CoA (or some portion thereof) is omega functionalized.
Microorganisms, preferably bacteria, can also be engineered to have significantly overexpressed ketoacyl-CoA thiolases and/or polyketoacyl-CoA thiolases, along with the other genes described herein. Preferably that is at least 10 fold as much thiolase activity as beta oxidation enzymes, or 20, 50 or 100 fold higher, thus driving the desired formation of polyketides, rather than immediately reducing the beta keto group with reverse BOX reactions. Also, preferred, thioesterase is reduced.
A genetically engineered microorganism, wherein said microorganism has a polyketide-producing pathway comprising the following substrate(s) to product(s) conversion:
a) C(n)-acyl-CoA + acetyl-CoA → C(n+2)-ketoacyl-CoA;
b) C(n+2)-ketoacyl-CoA + acetyl-CoA → C(n+4)-polyketoacyl-CoA;
c) iterations of reaction in step b, wherein said iterations are achieved by utilizing the polyketoacyl-CoA generated in step b as a substrate for condensation with acetyl-CoA to elongate the polyketoacyl-CoA chain by two carbons and add a beta-keto group; and
d) conversion of said polyketoacyl-CoA in steps b or c to a polyketide or a spontaneously rearranged form of said polyketide.
A genetically engineered microorganism, wherein said microorganism has a polyketide-producing pathway comprising the following substrate(s) to product(s) conversions:
e) C(n)-acyl-CoA + acetyl-CoA → C(n+2)-ketoacyl-CoA;
f) C(n+2)-ketoacyl-CoA + acetyl-CoA → C(n+4)-polyketoacyl-CoA;
g) C(n+4)-polyketoacyl-CoA → 3-OH- C(n+4)-polyketoacyl-CoA;
h) 3-OH- C(n+4)-polyketoacyl-CoA → C(n+4)-polyketoenoyl-CoA;
i) C(n+4)-polyketoenoyl-CoA → C(n+4)-α,β-unsaturated-polyketoacyl-CoA;
j) iterations of reactions in steps f, g, h and i, wherein said iterations are achieved by utilizing the polyketoacyl-CoAs, 3-OH-polyketoacyl-CoAs, polyketoenoyl-CoA, and α,β-unsaturated-polyketoacyl-CoA generated in reactions steps f, g, h, and i as substrates for condensation with acetyl-CoA to elongate said polyketoacyl-CoAs, 3-OH-polyketoacyl-CoAs, and polyketoenoyl-CoA chains by two carbons and add a beta-keto group;
k) conversion of said polyketoacyl-CoA in steps f, g, h, I, or j to a polyketide or a spontaneously rearranged form of said polyketide.
The RBOX enzymes used herein can be any enzymes described herein, or any homologs have the same activity. Exemplary enzyme include a thioesterase encoded by gene(s) selected from the group consisting of *E. coli* tesA, *E. coli* tesB, *E. coli* yciA, *E. coli* fadM, *E. coli* ydil, *E. coli* ybhC, *E. coli* paal, *Mus musculus* acot8, *Alcanivorax borkumensis* tesB2, *Fibrobacter succinogenes*, Fs2108, *Prevotella ruminicola* Pr655, *Prevotella ruminicola* Pr1687, *Lycopersicon hirsutum* glabratum mks2; a 3-OH-polyketoacyl-CoA dehydrogenase encoded by gene(s) selected from the group consisting of *E. coli* fabG, *E. coli* fadB, *E. coli* fadJ, *E. coli* paaH, *P. putida* fadB, *P. putida* fadB2x, *Acinetobacter* sp. ADP1 dcaH, *Ralstonia eutrophus* phaB, *Clostridium acetobutylicum* hbd; a 3-OH-polyketoacyl-CoA dehydratase encoded by a gene(s) selected from the group consisting of *E. coli* fabA, *E. coli* fabZ, *E. coli* fadB, *E. coli* fadJ, *E. coli* paaF, *P. putida* fadB, *P. putida* fadB1x, *Acinetobacter* sp. ADP1 dcaE, *Clostridium acetobutylicum* crt, *Aeromonas caviae* phaJ.
A recombinant microorganism having an overexpressed thiolase that catalyzes the following reaction:

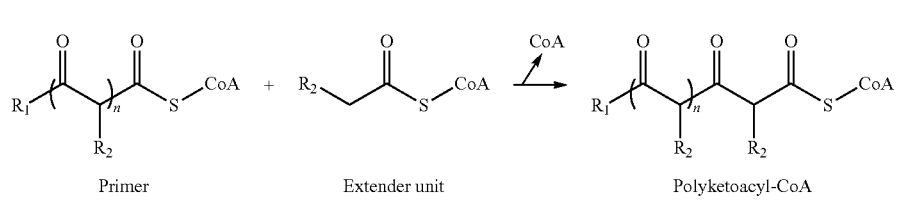

Primer      Extender unit      Polyketoacyl-CoA as well as reduced activity of endogenous ketoacyl-CoA dehydrogenase activity, and optionally reduced activity of endogenous thioesterase activity.
A recombinant microorganism having overexpressed genes encoding at least two different thiolases, said thiolases including a acetoacety-CoA thiolase or a ketoacyl thiolase and a polyketoacyl-CoA thiolase. Another option is a recombinant microorganism having overexpressed genes encoding a ketoacyl-CoA thiolase or acetoacyl-CoA thiolase and a polyketoacyl-CoA thiolase, and reduced activity of endogenous thioesterase activity. In some embodiments, the thiolases have at least 10 fold more activity than ketoacyl-CoA dehydrogenase or polyketoacyl-CoA dehydrogenase activity, preferably, 20, 50, 100 fold or more. Preferably, the genes are under the control of an inducible promoter, or a constitutive promoter. They may also be integrated genes.
A microorganism as herein described further comprising reduced expression of fermentation enzymes leading to reduced production of lactate, acetate, ethanol and succinate, preferably ΔadhE, (Δpta or ΔackA or ΔackApt), ΔpoxB, ΔldhA, and ΔfrdA.
Method as described herein, wherein said polyketide is further modified to produce a polyketide derivative. Such derivatives include dehydroacetic acid, olivetolie acid, cannabigerolic acid, orsellinic acid, or 6-methylsalicyclic acid.

Many examples of polyketoacyl-CoA thiolase enzymes which can potentially catalyze the non-decarboxylative Claisen condensation of a ketoacyl-CoA or polyketoacyl-CoA primer and acyl-CoA extender unit are provided herein, and Table 4 below provides additional examples which can also serve as templates for engineered variants:

TABLE 4

Example polyketoacyl-CoA Thiolase Enzymes (EC Number 2.3.1.-)

| Source organism and gene name | Protein Accession Numbers |
|---|---|
| Ralstonia eutropha bktB | AAC38322.1 |
| Pseudomonas putida pcaF | AAA85138.1 Q51956 |
| Rhodococcus opacus pcaF | YP_002778248.1 |
| Streptomyces sp. pcaF | AAD22035.1 |

Other materials used in exemplifying the invention include those in Table 5:

TABLE 5

Exemplary materials

| Type | Name | Accession No. or Source |
|---|---|---|
| Thiolase | Escherichia coli AtoB | GenBank: NP_416728.1 |
| | Escherichia coli FadA | GenBank: YP_026272.1 |
| | Escherichia coli PaaJ | GenBank: NP_415915.1 |
| | Pseudomonas putida FadA | GenBank: AAK18168.1 |
| | Pseudomonas putida PcaF | GenBank: AAA85138.1 |
| | Pseudomonas putida FadAx | GenBank: AAK18171.1 |
| | Cupriavidus necator BtkB | UniProt: Q0KBP1 |
| | Rhodococcus opacus PcaF | GenBank: BAH49303.1 |
| | Streptomyces sp. PcaF | GenBank: AAD22035.1 |
| | Acinetobacter sp. ADP1 DcaF | GenBank: CAG68532.1 |
| | Ralstonia eutropha BktB | GenBank: AAC38322.1 |
| Hydroxyacyl-CoA dehydrogenase | Escherichia coli FadB | GenBank: NP_418288.1 |
| | Escherichia coli PaaH | GenBank: NP_415913.1 |
| | Escherichia coli FadJ | GenBank: NP_416843.1 |
| | Pseudomonas putida FadB | GenBank: AAK18167.2 |
| | Pseudomonas putida FadB2x | GenBank: AAK18170.1 |
| | Acinetobacter sp. ADP1 DcaH | GenBank: CAG68533.1 |
| | Ralstonia eutrophus PhaB | UniProt: P14697.1 |
| | Clostridium acetobutylicum Hbd | GenBank: AAA95971.1 |
| | Escherichia coli FabG | GenBank: NP_415611.1 |
| | Escherichia coli FadB | GenBank: NP_418288.1 |
| Enoyl-CoA hydratase | Escherichia coli FadJ | GenBank: NP_416843.1 |
| | Escherichia coli PaaF | GenBank: NP_415911.1 |
| | Pseudomonas putida FadB | GenBank: AAK18167.2 |
| | Pseudomona putida FadB1x | GenBank: AAK18173.1 |
| | Acinetobacter sp. ADP1 DcaE | GenBank: CAG68535.1 |
| | Clostridium acetobutylicum Crt | GenBank: AAA95967.1 |
| | Aeromonas caviae PhaJ | UniProt: O32472.1 |
| Enoyl-CoA reductase | Euglena gracilis TER | UniProt: Q5EU90.1 |
| Thioesterase | Escherichia coli TesA | GenBank: NP_415027.1 |
| | Escherichia coli TesB | GenBank: NP_414986.1 |
| | Escherichia coli YciA | GenBank: NP_415769.1 |
| | Escherichia coli FadM | GenBank: NP_414977.1 |
| | Escherichia coli Ydil | GenBank: NP_416201.1 |
| | Escherichia coli YbgC | GenBank: NP_415264.1 |
| | Mus musculus Acot8 | UniProt: P58137.1 |
| Olivetolic acid cyclase | Cannabis sativa OAC | GenBank: AFN42527.1 |
| Aromatic prenyl-transferase | Cannabis sativa CsPT1 | Source: US8884100 |
| | Humulus lupulus HIPT | GenBank: AJD80255.1 |
| | Escherichia coli UbiA | GenBank: NP_418464.1 |
| | Saccharomyces cerevisiae Coq2 | GenBank: AAA34507.1 |
| | Lithospermum erythrorhizon LePGT-1 | GenBank: BAB84122.1 |
| | Lithospermum erythrorhizon LePGT-2 | GenBank: BAB84123.1 |

TABLE 5-continued

Exemplary materials

| Type | Name | Accession No. or Source |
|---|---|---|
| Plasmid | pTrcHis2A | Source: Invitrogen, Carlsbad, CA |
| | pCA24N | GenBank: AB052891.2 |
| | pKD4 | Source: Datsenko and Wanner, 2000 |
| | pKD3 | Source: Datsenko and Wanner, 2000 |
| | pUCBB-ntH6 | Source: Vick et al. 2011 |
| | pUCBB-ntH6-eGFP | Source: Vick et al. 2011 |
| | pCDFDuet-1 | Source: Novagen, Darmstadt, Germany |
| | pETDuet-1 | Source: Novagen, Darmstadt, Germany |

Figure 6:
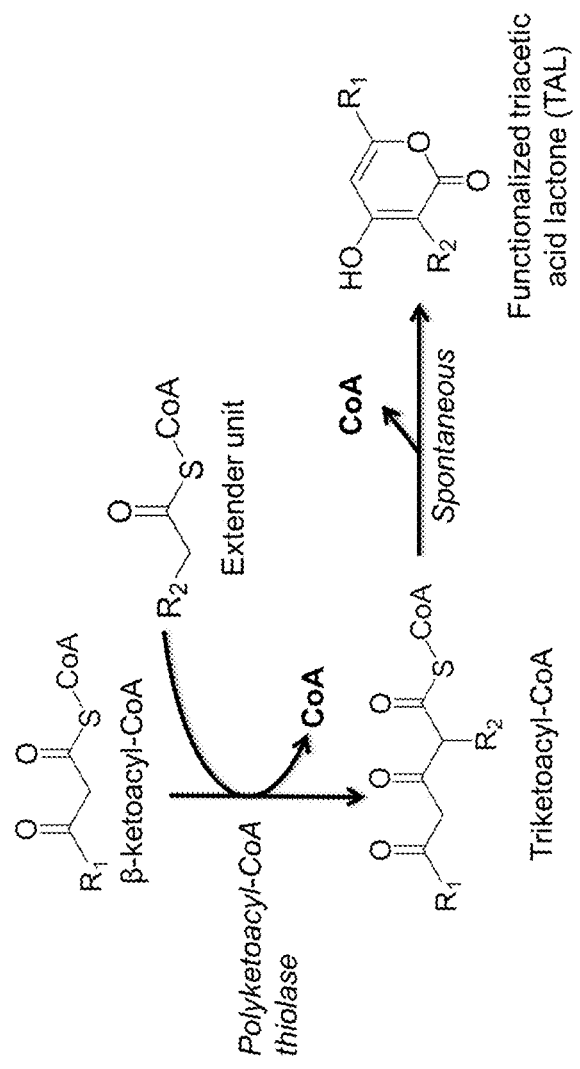
FIG. 6: Example pathway for the synthesis of triketide functionalized triacetic acid lactone (TAL). After non-decarboxylative condensations of primer β-ketoacyl CoA thioester with functionalized group R1 and the extender unit acyl-CoA with functionalized group R2 catalyzed by polyketoacyl-CoA thiolase, triketoacyl-CoA is produced and it can be spontaneously converted to TAL.

The disclosed methods can be used to produce a variety of polyketides with better energy efficiency than normal polyketide synthesis. FIGS. 3-4 and FIG. 6 display exemplary mechanisms.

Figure 3A:
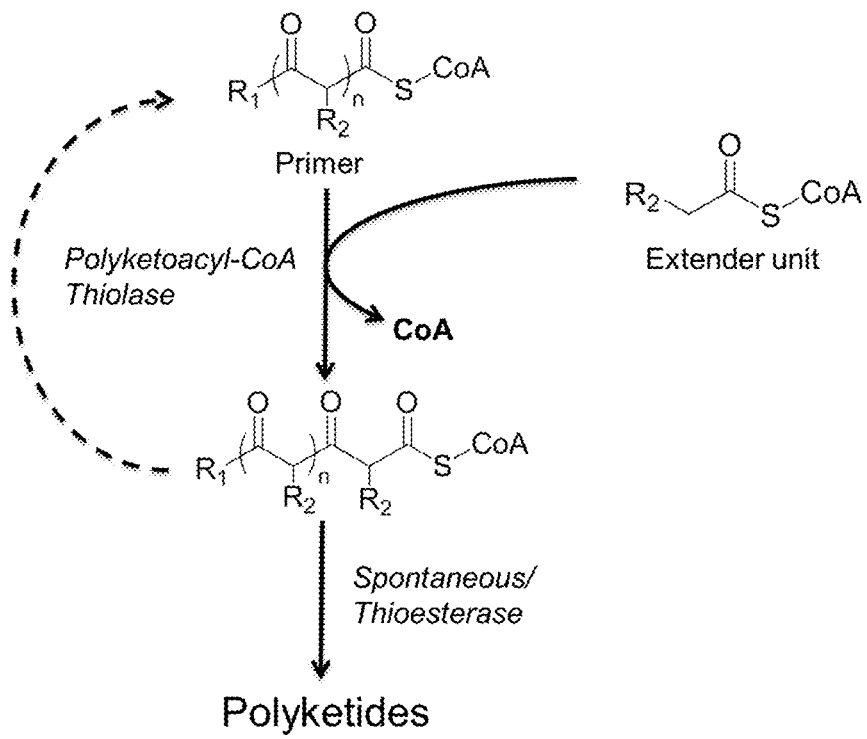
FIG. 3A: Synthesis of polyketides through polyketoacyl-CoA thiolase-catalyzed non-decarboxylative Claisen condensations. Thiolases naturally catalyze the condensation between an acyl-CoA thioester, serving as the primer, and another acyl-CoA thioester, serving as the extender unit, forming 3-ketoacyl-CoAs. As demonstrated in this invention, the aforementioned 3-ketoacyl-CoAs can also serve as the primer, which upon condensation with an extender unit generates a polyketide CoA thioester or polyketoacyl-CoA. Prior to this invention, thiolases had not been known to catalyze said condensation reaction between a 3-ketoacyl-CoA and acetyl-CoA to generate a polyketoacyl-CoA, and hence we herein define said thiolases as "polyketoacyl-CoA thiolases." After repeated condensations, polyketoacyl-CoAs of different chain lengths are formed. After hydrolysis (spontaneously or by the action of thioesterases) and subsequent spontaneous reactions, polyketides are produced. Primers and extender units can be omega-functionalized by R1 and R2 groups, respectively. The "n" means length of polyketides, and it is an integer number larger than one and less than 20, preferably about 4-16, 6-12 or any integer between. Dashed line indicates multiple iterations.
Figure 3B:
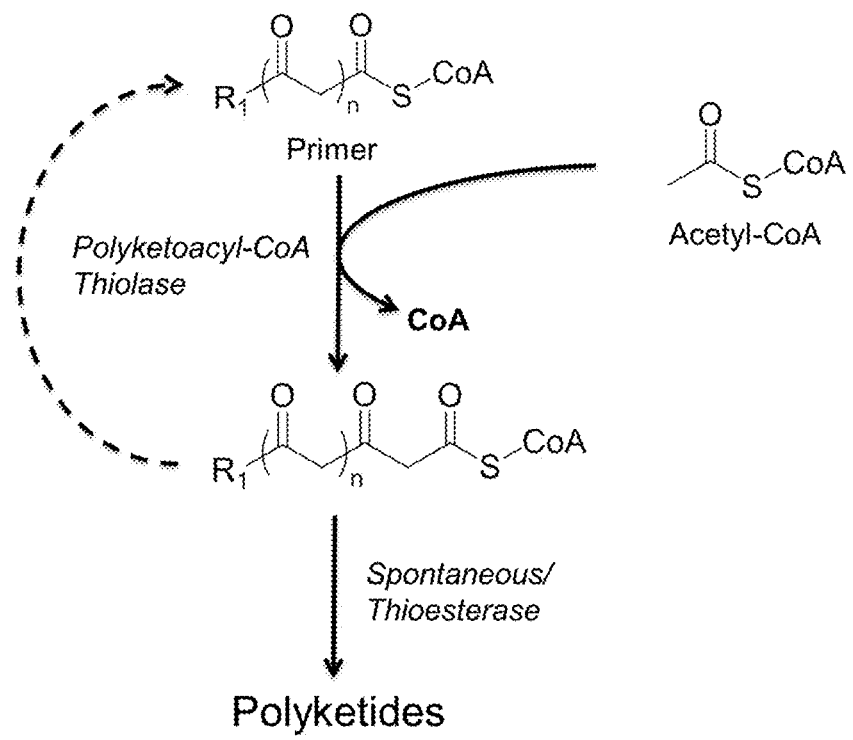
FIG. 3B: Polyketide synthesis pathway depicted in FIG. 3A with acetyl-CoA as the extender unit (R2=—H).

In FIG. 3A, generic synthesis of polyketides through native or engineered polyketoacyl-CoA thiolase-catalyzed non-decarboxylative Claisen condensations are shown. Ketoacyl-CoA thiolases catalyze the condensation between an acyl-CoA thioester, serving as the primer, and another acyl-CoA thioester, serving as the extender unit, forming β-keto acyl-CoA. This β-keto acyl-CoA can serve as the primer for the next polyketoacyl-CoA thiolase condensation with the extender unit in a series of iterated condensations to form polyketoacyl-CoAs. After hydrolysis (spontaneously or by the action of thioesterases) and subsequent spontaneous reactions, polyketides are produced. This variation in R groups allows for the generation of a diverse group of products, thus increasing what is available for end-use in e.g. therapeutics or a feedstock to make therapeutics. FIG. 3B is the polyketide synthesis pathway depicted in FIG. 3A with acetyl-CoA as the extender unit (R2=—H).

Figure 4A:
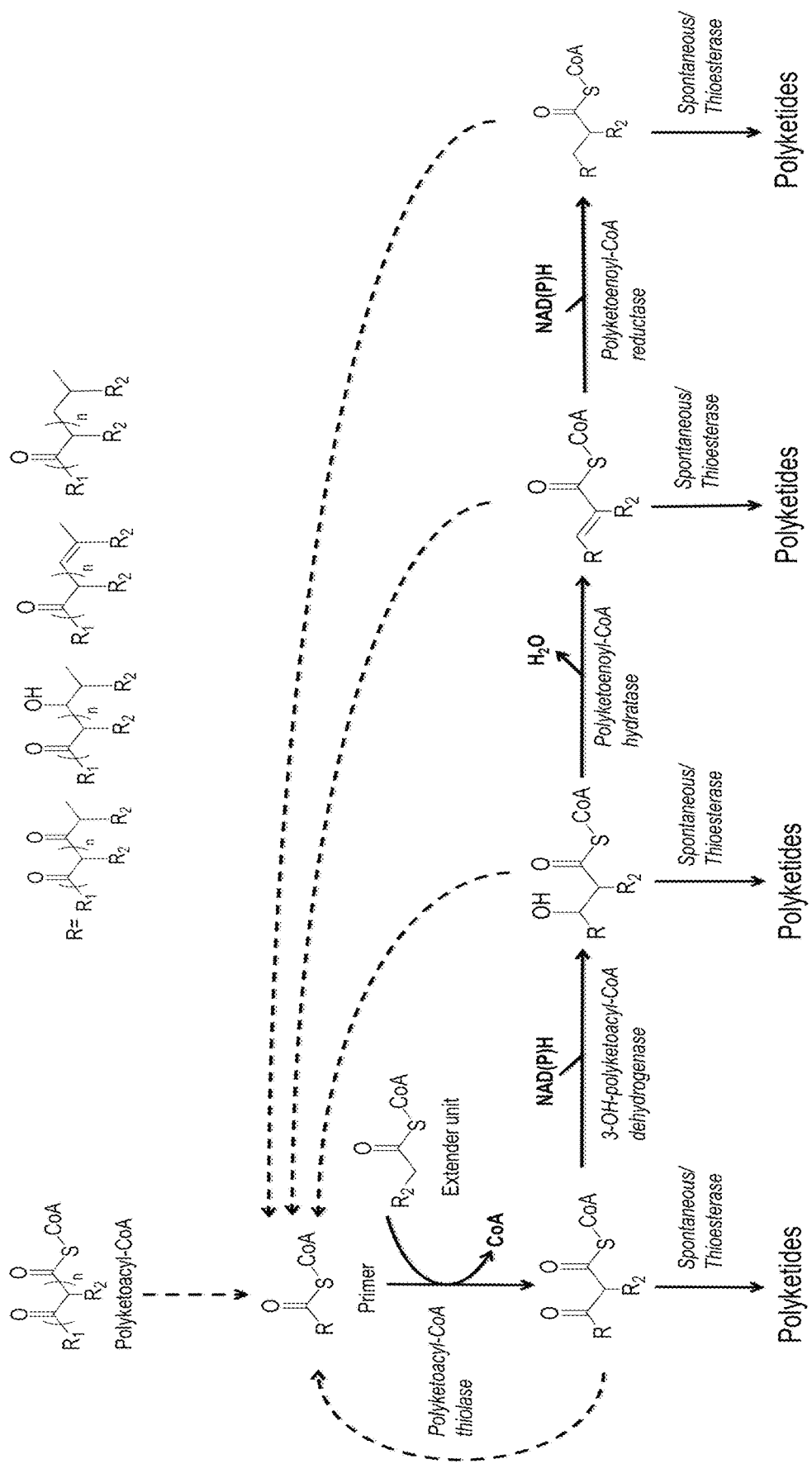
FIG. 4A: β-reductions of the polyketoacyl-CoA synthesized through polyketoacyl-CoA thiolase-catalyzed non-decarboxylative Claisen condensations. 3-OH-polyketoacyl-CoA dehydrogenases reduce the β-keto group of polyketoacyl-CoA synthesized by a series of polyketoacyl-CoA thiolase condensations to β-hydroxy group. Polyketoenoyl-CoA hydratases catalyze the dehydration of β-keto group to the α, β double bond. Polyketoenoyl-CoA reductases reduce the α, β double bond to the single bond. The β-reduced polyketoacyl-CoA can be hydrolyzed (spontaneously or by thioesterases) to yield polyketides. The β-reduced polyketoacyl-CoAs can also serve as the primers for the next round of non-decarboxylative condensation with the extender unit. The initial primer can be omega-functionalized by R1 group. Extender units can be omega-functionalized by R2 group. The "n" means length of polyketides, and it is larger than zero. The "R" group is selected from four groups containing R1 and R2 and is listed in the upper right side to show that any β-reduced polyketoacyl-CoAs can serve as the primers for the next round of non-decarboxylative condensation with the extender unit. Dashed lines indicate iterations of polyketide synthesis.
Figure 4B:
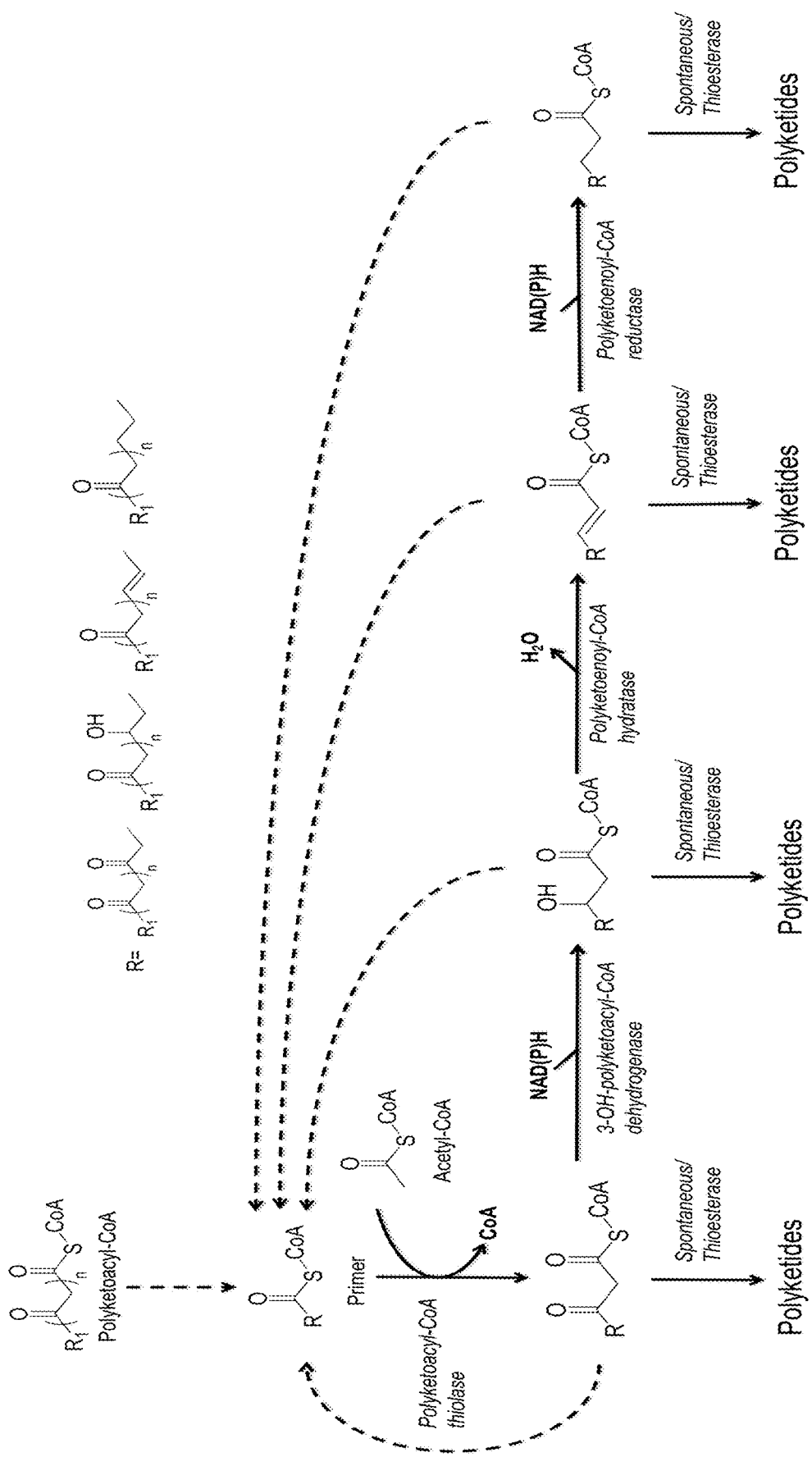
FIG. 4B: β-reductions of polyketides depicted in FIG. 4A with acetyl-CoA as the extender unit (R=—CH$_3$).

FIG. 4A shows β-reductions of polyketides synthesized through polyketoacyl-CoA thiolase-catalyzed non-decarboxylative Claisen condensations. 3-OH-polyketoacyl-CoA dehydrogenases reduce the β-keto group of polyketoacyl-CoA synthesized by a series of polyketoacyl-CoA thiolase condensations to β-hydroxy group. Polyketoenoyl-CoA hydratases catalyze the dehydration of β-keto group to the α, β double bond. Polyketoenoyl-CoA reductases reduce the α, β double bond to the single bond. The β-reduced polyketoacyl-CoA can be hydrolyzed (spontaneously or by thioesterases) to yield polyketides. The β-reduced polyketoacyl-CoAs can also serve as the primer for the next round of non-decarboxylative condensation with the extender unit. Dashed lines indicate iterations of polyketide synthesis. FIG. 4B shows the β-reductions of polyketides depicted in FIG. 4A with acetyl-CoA as the extender unit (R=—CH$_3$).

Figure 5:
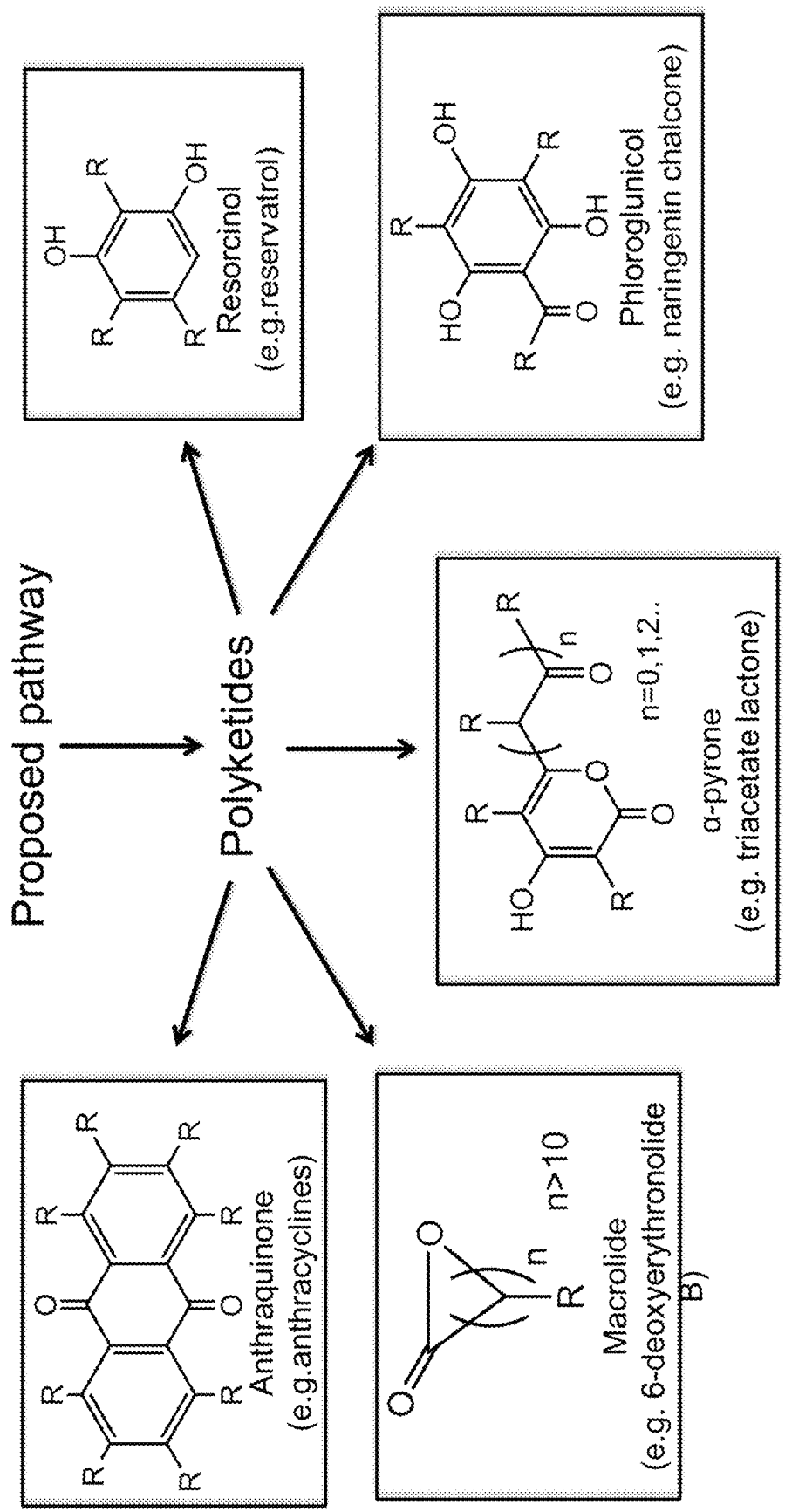
FIG. 5: Possible polyketide products of the proposed pathway, which include functionalized macrolides, phloroglunicols, α-pyrones, resorcinols and anthraquinones.

FIG. 5 shows possible polyketide products of the proposed pathway, which include functionalized macrolides, phloroglunicols, α-pyrones, resorcinols and anthraquinones.

In our proof of concept work, we made a triketide by polyketoacyl-CoA thiolase-catalyzed non-decarboxylative Claisen condensation between acetoacetyl-CoA (a ketoacyl-CoA acting as the primer) and acetyl-CoA (an acyl-CoA acting as extender unit), which generates 3,5-diketohexanoyl-CoA (a polyketoacyl-CoA). The spontaneous hydrolysis and cyclization of 3,5-diketohexanoyl-CoA formed triacetic acid lactone (4-hydroxy-6-methyl-2-pyrone):

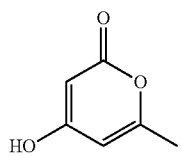

FIG. 6 shows the exemplary pathway of synthesis of triketide functionalized triacetic acid lactone (TAL) using the disclosed methods. After non-decarboxylative condensations of primer ketoacyl-CoA thioester with functionalized group (R1) and the extender unit acetyl-CoA with functionalized group (R2) catalyzed by polyketoacyl-CoA thiolase, the triketide diketoacyl-CoA is produced and it can be spontaneously converted to functionalized TAL.

Figure 7:
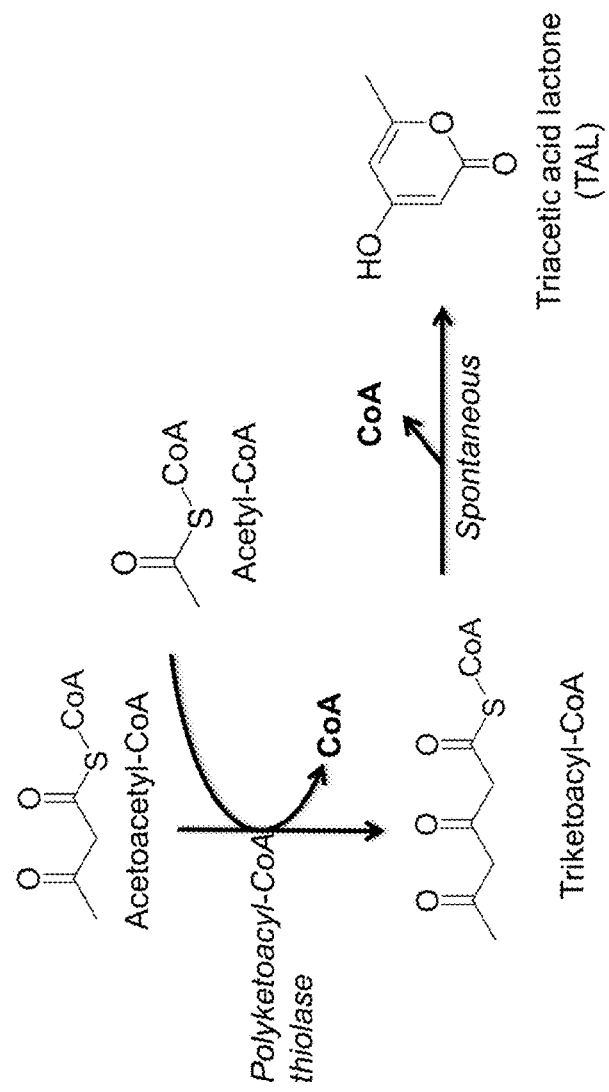
FIG. 7: Triketide synthesis pathway depicted in FIG. 6 with acetoacetyl-CoA as primer (R1=—CH$_3$) and acetyl-CoA as the extender unit (R2=—H). The final product is triacetic acid lactone (TAL).

FIG. 7 shows the synthesis of triacetic acid lactone (TAL) through the pathway depicted in FIG. 6 with R1=—CH$_3$ and R2=—H.

Figure 8:
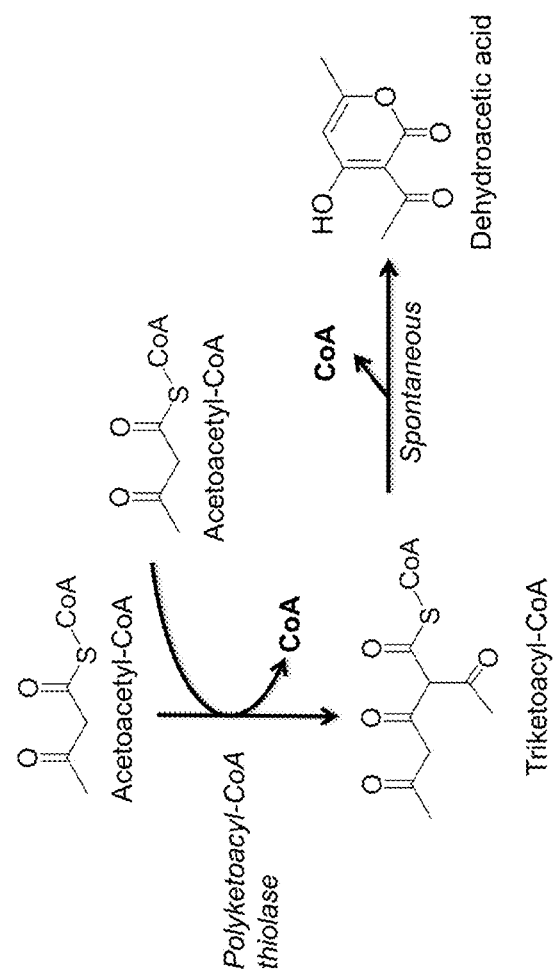
FIG. 8: Triketide synthesis pathway depicted in FIG. 6 with acetoacetyl-CoA as primer (R1=—CH$_3$) and acetoacetyl-CoA as the extender unit (R2=—COCH$_3$). The final product is dehydroacetic acid.

FIG. 8 shows the synthesis of dehydroacetic acid through the pathway depicted in FIG. 6 with R1=—CH$_3$ and R2=—COCH$_3$.

Standard molecular biology techniques were used for gene cloning, plasmid isolation, and E. coli transformation. Native E. coli genes were amplified from E. coli MG1655 genomic DNA using primers to append homology on each end of the gene insert for recombination into the vector backbone. Genes from other organisms were codon optimized and synthesized by either GeneArt (Life Technologies, Carlsbad, Calif.) or GenScript (Piscataway, N.J.). Plasmids were linearized by the appropriate restriction enzymes and recombined with the gene inserts using the In-Fusion HD Eco-Dry Cloning system (Clontech laboratories, Mountain View, Calif.). The mixture was subsequently transformed into Stellar competent cells (Clontech laboratories, Mountain View, Calif.).

Transformants that grew on solid media (LB+Agar) supplemented with the appropriate antibiotic were isolated and screened for the gene insert by PCR. Plasmid was isolated from the verified transformants and the sequence of the gene insert was further confirmed by DNA sequencing (Lone Star Labs, Houston, Tex.). Plasmids (also referred to as vectors) in each case contain at least one promoter, a ribosome binding site for each gene, the gene(s) of interest, at least one terminator, an origin of replication, and an antibiotic resistance marker.

Genes encoding Pseudomonas putida FadA and FadAx, Acinetobacter sp. DcaF, and Streptomyces collinus FadA were cloned into the pCDFDuet-1 vector and were expressed with an N-terminal 6-His-tag. The gene encoding Mus musculus Acot8 was cloned into the pETDuet-1 vector and was expressed with an N-terminal 6-His-tag. Genes encoding Pseudomonas putida PcaF and Euglena gracilis TER were cloned into the pTrcHis2A vector and were expressed with a C-terminal 6-His-tag. Genes encoding E. coli FadA and FadB, Clostridium acetobutylicum Hbd and Ralstonia eutropha BktB were cloned from genomic DNA into the pUCBB-ntH6 vector to yield a constitutively expressed gene with an N-terminal 6-His-tag. For E. coli AtoB, FadM, TesA, TesB, YbgC, YciA, YdiI, PaaJ and PaaH, the pCA24N- gene (-gfp) plasmids from the ASKA collection were used (Kitagawa et al., 2005).

Cultures were grown overnight in 25 mL of LB media in 125 mL baffled flasks (Wheaton Industries, Inc., Millville, N.J.) for thiolase assay on condensation between acetoacetyl-CoA and acetyl-CoA or in 100 mL of LB media in 250 mL baffled flasks (Wheaton Industries, Inc., Millville, N.J.) for other enzymatic assays at 37° C. in E. coli BL21 (DE3) cells induced with 1 mM IPTG (pCA24N, pTrcHis2A) at an OD600~0.6, or expressed constitutively (pUCBB-ntH6). Reactions were monitored on either a Synergy HT plate reader (BioTek Instruments, Inc., Winooski, Vt.) at 25° C. or in a Biomate 5 Spectrophotometer (Thermo Scientific, Waltham, Mass.).

For thiolase assay on the condensation reaction between acetoacetyl-CoA and acetyl-CoA, the cell lysis and protein purification processes are as below: After post-induction growth for 4 h for ASKA strains, or 16 for other strains, the cells were collected and washed twice by 9 g/L sodium chloride solution. Then, cells were re-suspended by lysis buffer (50 mM NaH$_2$PO$_4$, 300 mM NaCl, 10 mM imidazole, pH 8.0). After re-suspension, the cells were disrupted by Disruptor Genie (Scientific Industries), and then centrifuged at 4° C., 13000G, 10 min. The resultant supernatant is the crude enzyme extract.

The His-tagged enzymes were then purified from crude extract by using Ni-NTA spin kit (Qiagen, Valencia, Calif.). The crude extracts are centrifuged in spin columns that were equilibrated with lysis buffer for 270G, 5 min. The column was then washed twice with a wash buffer (50 mM NaH$_2$PO$_4$, 300 mM NaCl, 20 mM imidazole, pH 8.0). After washing, the enzyme was eluted twice in elution buffer (50 mM NaH$_2$PO$_4$, 300 mM NaCl, 500 mM imidazole, pH 8.0). Both washing and elution used centrifuge at 890G, 2 min.

The purified enzyme extracts were then further concentrated and dialyzed through Amicon® Ultra 10K Device (Millipore, Billerica, Mass.). The enzymes were first filtered through centrifugation at 4° C., 14000G, 10 min, and then washed with 100 mM potassium phosphate, pH 7 buffer at same centrifugation conditions. Finally, the concentrated and dialyzed enzymes were recovered through 4° C., 1000G, 2 min centrifugation. The protein concentration was established using the Bradford Reagent (Thermo Scientific, Waltham, Mass.) using bovine serum albumin (BSA) as the protein standard.

For other enzymatic assays, cells were lysed using Bacterial Protein Extraction Reagent (B-PER) (Thermo Scientific, Waltham, Mass.) as per the prescribed protocol in order to obtain the supernatant containing the active enzymes. Cell pellets were resuspended in 40 mL of 50 mM potassium phosphate buffer pH 7.2 and broken by disruption EmulsiFlex-05 homogenizer (Avestin, Ottawa, ON). Disrupted cells were then spun for 90 min at 4° C. at 120,000×g in an Optima L-80XP Ultracentrifuge (Beckman-Coulter, Schaumburg, Ill.) to produce the supernatant used for assays.

For specific activity assays (reported in μmol substrate/mg protein/min) these supernatant fractions were utilized and protein concentration was established using the Bradford Reagent (Thermo Scientific, Waltham, Mass.) using BSA as the protein standard. Linearity was established for each reaction and the background non-enzymatic rate was subtracted to establish the activity.

The assay of triacetic acid lactone (TAL) synthesis through thiolase condensation between acetoacetyl-CoA and acetyl-CoA was performed in the presence of 100 mM potassium phosphate pH 7, 3 mM EDTA, 1 mM acetoacetyl-CoA and 1 mM acetyl-CoA in a total volume of 220 μL for BktB or 200 μL for other tested thiolases at 25° C.

For BktB, 24 μL of undiluted enzyme elute was added in the assay system, while for other thiolases, 4 μL of undiluted enzymes were added. The activity was monitored by the increase of TAL at 298 nm using an extinction coefficient of 2.9443 mM$^{-1}$ cm$^{-1}$ measured through calibration of TAL standards. TAL formation in assay samples was then confirmed through HPLC Shimadzu LC-20AD HPLC system with an SPD-20A dual-wavelength UV-VIS detector and a Phenomonex Luna C18 column (25 cm×4.6 mm, 5 μm) (Tang et al. 2013). The TAL formation in assay samples was also identified through MicroTof ESI mass spectrometer with comparison to TAL standard.

Thiolases have never been shown to catalyze the needed condensation reactions to form polyketides. Therefore, one of our first experiments was to characterize the activity of the enzymes composing the pathway, in both the forward and reverse directions.

Thiolase thiolytic activity was determined in the presence of 0.5 mM DTT, 4.5 mM $MgCl_2$, 100 mM Tris HCl pH 7.5, and 2 mM CoA in a total volume of 200 μL at 25° C. Activity was monitored by the loss of acetoacetyl-CoA at 303 nm using an extinction coefficient of 14 $mM^{-1}$ $cm^{-1}$. Both the β-hydroxyacyl-CoA dehydrogenase assays and the thiolase biosynthetic activity were performed in the presence of 1.5 mM DTT, 4.5 mM $MgCl_2$, 100 mM Tris HCl pH 7.5 and 0.2 mM NADH in a total volume of 200 μL at 25° C. Thiolase activity in the biosynthetic direction was measured at 340 nm in a coupled assay in which 10 U excess of β-hydroxyacyl-CoA dehydrogenase was present to reduce the β-ketoacyl-CoA generated from thiolase activity.

Dehydrogenase activity was monitored by following the oxidation of NADH at 340 nm. Enoyl-CoA hydratase activity was monitored by following the loss of crotonoyl-CoA at 263 nm ($\varepsilon$=6.7 $mM^{-1}$ $cm^{-1}$) in the presence of 100 mM Tris HCL pH 7.5 in 200 μL total volume. Enoyl-CoA reductase activity was followed by monitoring the loss of NADH absorbance in the presence of 100 mM Tris HCL pH 7.5 and 0.2 mM NADH in a final volume of 200 μL at 25° C.

Thioesterase activity was monitored by following the production of thionitrobenzoic acid (TNB) at 412 nm ($\varepsilon$=4.3 $mM^{-1}$ $cm^{-1}$). Reactions were carried out in the presence of 100 mM Tris pH 7.5, 200 mM KCl, 25 mM 5,5-dithio-bis-(2-nitrobenzoic acid) (DTNB) and 200 μM of the "-CoA" substrate in a volume of 200 μL at 25° C.

FIG. 10-14 show time profiles for the increase in absorbance at 298 nm due to production of TAL by different thiolases. These data provide a demonstration of the ability of certain thiolases, referred to here as "polyketoacyl-CoA" thiolases (PcaF, BktB, FadA, DcaF, FadAx) to catalyze a non-decarboxylative Claisen condensation reaction between a ketoacyl-CoA or a polyketoacyl-CoA (e.g. acetoacetyl-CoA, serving as starter unit) and an acyl-CoA or activated carboxylic acid (e.g. acetyl-CoA, serving as extender unit) to generate a polyketoacyl-CoA (e.g. 3,5-diketohexanoyl-CoA), which undergoes hydrolysis and ring closure to produce TAL.

Figure 15:
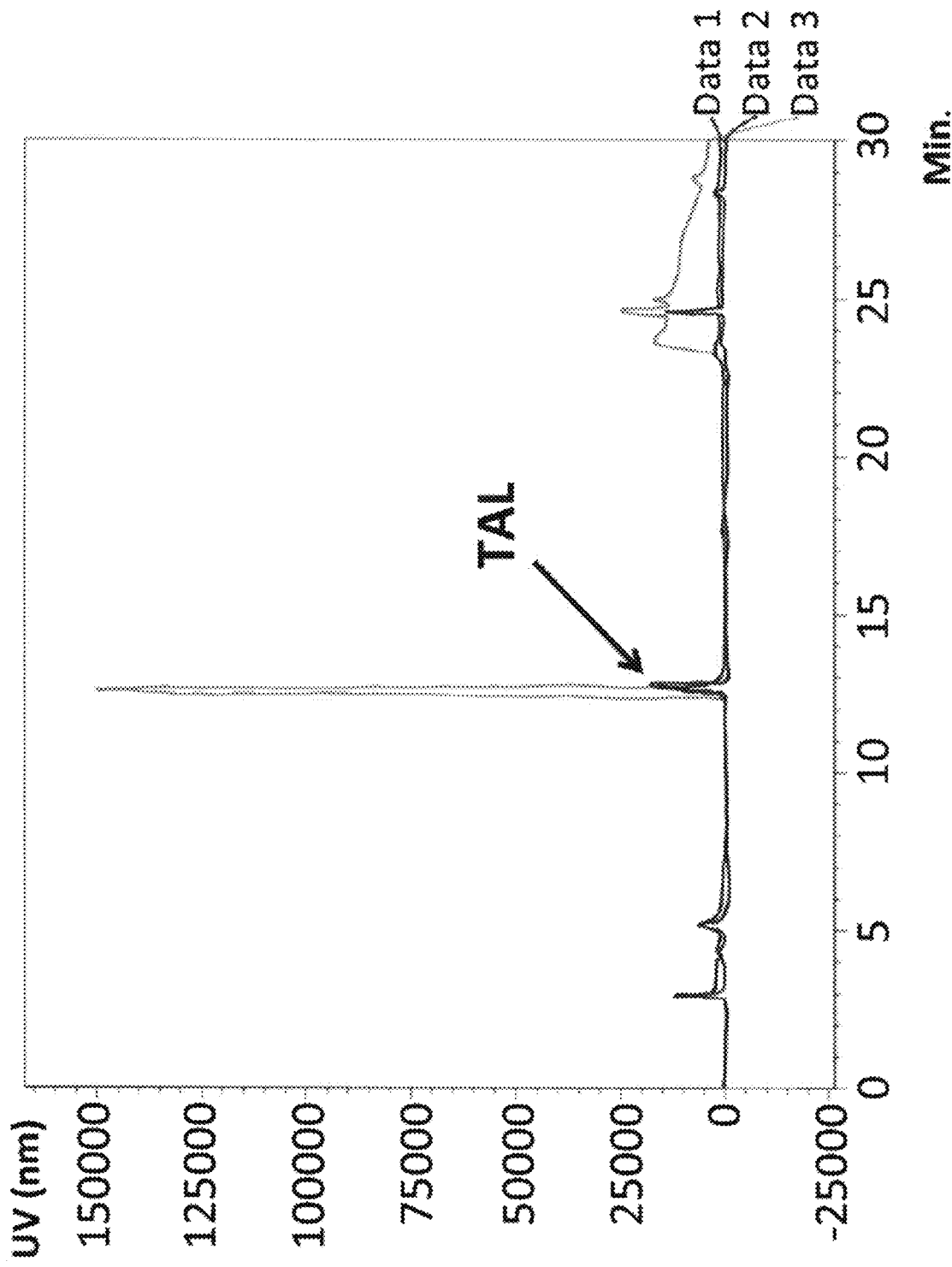
FIG. 15: HPLC chromatograms indicating TAL synthesis in assay samples of FadAx. Two replicate assay samples were tested, and their chromatograms are displayed in Data 1 and Data 2. The chromatogram of a 0.31 mM TAL standard solution is displayed in Data 3. The retention time of TAL is ~12.6 min, and the TAL peak is pointed by the arrow.

FIG. 15 shows an HPLC chromatogram indicating the formation of TAL through the condensation reaction between acetoacetyl-CoA and acetyl-CoA by thiolase FadAx. These results provide the basis of novel polyketide synthesis through non-decarboxylative condensation reactions catalyzed by thiolases instead of decarboxylative reactions catalyzed by polyketide synthases, and β-reduction modifications on polyketide carbon-chain by 3-OH-polyketoacyl-CoA dehydrogenases, polyketoenoyl-CoA hydratases and polyketoenoyl-CoA reductases.

Figure 16:
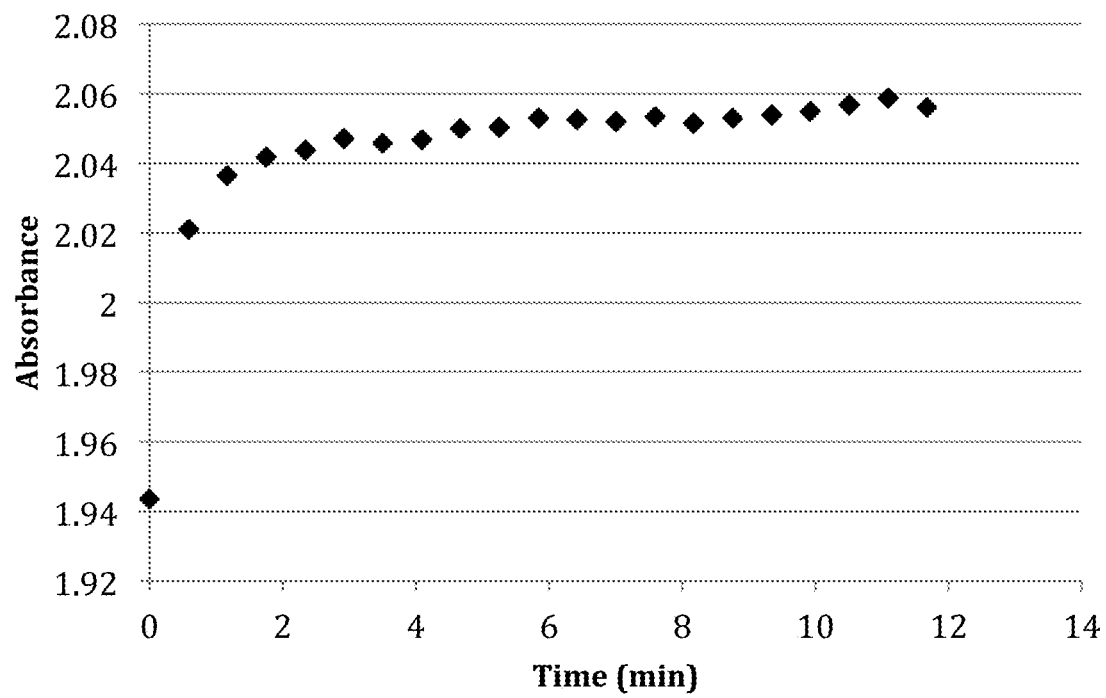
FIG. 16: Time profile for increase in absorbance at 312 nm due to production of dehydroacetic acid by *Pseudomonas putida* polyketoacyl-CoA thiolase PcaF.
Figure 17:
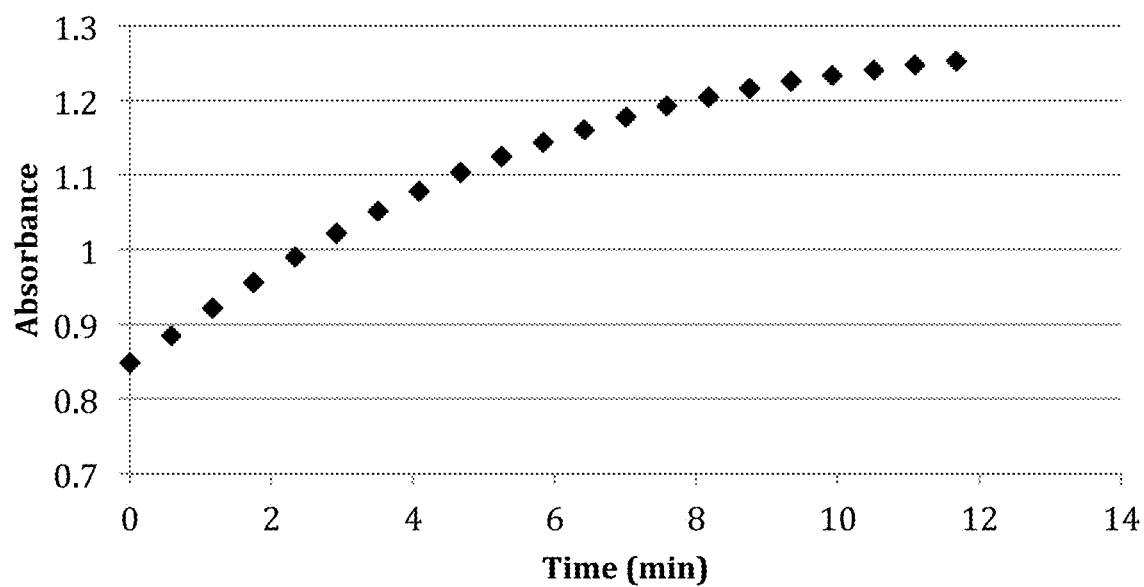
FIG. 17: Time profile for increase in absorbance at 312 nm due to production of dehydroacetic acid by *Pseudomonas putida* polyketoacyl-CoA thiolase FadAx.

FIG. 16-17 show time profiles for the increase in absorbance at 312 nm due to production of dehydroacetic acid by different polyketoacyl-CoA thiolases. These figures provide a demonstration of the ability of certain polyketoacyl-CoA thiolases (PcaF, FadAx) to catalyze a non-decarboxylative Claisen condensation reaction between a ketoacyl-CoA (acetoacetyl-CoA, serving as starter unit) and another ketoacyl-CoA (acetoacetyl-CoA, serving as extender unit) to generate a polyketoacyl-CoA, which undergoes ring closure to produce dehydroacetic acid.

Table 6 shows the characterization of several enzymes tested for use herein. Several enzymes with one substrate show the availability of several enzymes as catalysts for the same reaction. Testing of adipyl, crotonyl, and the like, shows activity on functionalized substrates.

TABLE 6

Characterization of enzymes depicted in the filing.

| ENZYME CLASS | ENZYME | SUBSTRATE | MEASURED ACTIVITY PROTEIN/MIN) | SPECIFIC REFERENCE (μMOL/MG |
|---|---|---|---|---|
| THIOLASE | E. COLI ATOB | ACETOACETYL-COA + ACETYL-COA | N.D. | THIS WORK |
| THIOLASE | E. COLI FADA | ACETOACETYL-COA + ACETYL-COA | N.D. | THIS WORK |
| THIOLASE | E. COLI PAAJ | ACETOACETYL-COA + ACETYL-COA | N.D. | THIS WORK |
| THIOLASE | PSEUDOMONAS PUTIDA FADA | ACETOACETYL-COA + ACETYL-COA | N.D. | THIS WORK |
| THIOLASE | PSEUDOMONAS PUTIDA FADAX | ACETOACETYL-COA + ACETYL-COA | 0.052 ± 0.014 | THIS WORK |
| THIOLASE | ACINETOBACTER SP. DCAF | ACETOACETYL-COA + ACETYL-COA | 0.041 | THIS WORK |
| THIOLASE | STREPTOMYCES COLLINUS FADA | ACETOACETYL-COA + ACETYL-COA | 0.007 | THIS WORK |
| THIOLASE | RALSTONIA EUTROPHA BKTB | ACETOACETYL-COA + ACETYL-COA | 0.00019 | THIS WORK |
| THIOLASE | E. COLI ATOB | ACETOACETYL-COA | 0.36 ± 0.05 | THIS WORK |
| THIOLASE | E. COLI FADA | ACETOACETYL-COA | 0.013 ± 0.002 | THIS WORK |
| THIOLASE | E. COLI ATOB | ACETYL-COA | 0.919 ± 0.002 ($K_M$: 892.0 ± 56.5 MM; $K_{CAT}$: 3.17 ± 0.18 $S^{-1}$. ASSAY COUPLED WITH DEHYDROGENASE HBD) | CLOMBURG ET AL. (2012) |
| THIOLASE | E. COLI PAAJ | SUCCINYL-COA + ACETYL-COA | 0.12 ± 0.02 (ASSAY COUPLED WITH DEHYDROGENASE PAAH) | THIS WORK |

TABLE 6-continued

Characterization of enzymes depicted in the filing.

| ENZYME CLASS | ENZYME | SUBSTRATE | MEASURED ACTIVITY (μMOL/MG PROTEIN/MIN) | SPECIFIC REFERENCE |
|---|---|---|---|---|
| THIOLASE | *PSEUDOMONAS PUTIDA* PCAF | SUCCINYL-COA + ACETYL-COA | 0.184 ± 0.009 (ASSAY COUPLED WITH DEHYDROGENASE PAAH) | THIS WORK |
| HYDROXYACYL-COA DEHYDROGENASE | *E. COLI* FADB | ACETOACETYL-COA | 0.185 ± 0.001 ($K_M$: 390.0 ± 19.2 MM; $K_{CAT}$: 25.9 ± 1.2 $S^{-1}$.) | CLOMBURG ET AL. (2012) |
| HYDROXYACYL-COA DEHYDROGENASE | *E. COLI* PAAH | ACETOACETYL-COA | 3.10 ± 0.22 | THIS WORK |
| HYDROXYACYL-COA DEHYDROGENASE | *CLOSTRIDIUM ACETOBUTYLICUM* HBD | ACETOACETYL-COA | 22.0 ± 1.0 | THIS WORK |
| ENOYL-COA HYDRATASE | *E. COLI* FADB | CROTONYL-COA | 0.051 ± 0.004 | THIS WORK |
| ENOYL-COA REDUCTASE | *EUGLENA GRACILIS* EGTER | CROTONYL-COA | 5.4 ± 0.6 ($K_M$: 98.5 ± 7.7 MM; $K_{CAT}$: 1.14 ± 0.08 $S^{-1}$.) | CLOMBURG ET AL. (2012) |
| THIOESTERASE | *E. COLI* FADM | ACETOACETYL-COA | 0.042 ± 0.004 | CLOMBURG ET AL. (2012) |
| THIOESTERASE | *E. COLI* TESA | ACETOACETYL-COA | 0.044 ± 0.005 | CLOMBURG ET AL. (2012) |
| THIOESTERASE | *E. COLI* TESB | ACETOACETYL-COA | 0.056 ± 0.001 | CLOMBURG ET AL. (2012) |
| THIOESTERASE | *E. COLI* YBGC | ACETOACETYL-COA | 0.065 ± 0.002 | CLOMBURG ET AL. (2012) |
| THIOESTERASE | *E. COLI* YCIA | ACETOACETYL-COA | 0.672 ± 0.007 | CLOMBURG ET AL. (2012) |
| THIOESTERASE | *E. COLI* YDII | ACETOACETYL-COA | 0.047 ± 0.001 | CLOMBURG ET AL. (2012) |
| THIOESTERASE | *E. COLI* FADM | 3-HYDROXYBUTYRYL-COA | 0.009 ± 0.002 | CLOMBURG ET AL. (2012) |
| THIOESTERASE | *E. COLI* TESA | 3-HYDROXYBUTYRYL-COA | 0.02 ± 0.01 | CLOMBURG ET AL. (2012) |
| THIOESTERASE | *E. COLI* TESB | 3-HYDROXYBUTYRYL-COA | 0.032 ± 0.002 | CLOMBURG ET AL. (2012) |
| THIOESTERASE | *E. COLI* YBGC | 3-HYDROXYBUTYRYL-COA | 0.016 ± 0.004 | CLOMBURG ET AL. (2012) |
| THIOESTERASE | *E. COLI* YCIA | 3-HYDROXYBUTYRYL-COA | 0.441 ± 0.009 | CLOMBURG ET AL. (2012) |
| THIOESTERASE | *E. COLI* YDII | 3-HYDROXYBUTYRYL-COA | 0.012 ± 0.002 | CLOMBURG ET AL. (2012) |
| THIOESTERASE | *E. COLI* FADM | CROTONYL-COA | 0.0017 ± 0.0003 | CLOMBURG ET AL. (2012) |
| THIOESTERASE | *E. COLI* TESA | CROTONYL-COA | 0.007 ± 0.003 | CLOMBURG ET AL. (2012) |
| THIOESTERASE | *E. COLI* TESB | CROTONYL-COA | 0.010 ± 0.001 | CLOMBURG ET AL. (2012) |
| THIOESTERASE | *E. COLI* YBGC | CROTONYL-COA | 0.006 ± 0.001 | CLOMBURG ET AL. (2012) |
| THIOESTERASE | *E. COLI* YCIA | CROTONYL-COA | 0.27 ± 0.03 | CLOMBURG ET AL. (2012) |
| THIOESTERASE | *E. COLI* YDII | CROTONYL-COA | 0.078 ± 0.005 | CLOMBURG ET AL. (2012) |
| THIOESTERASE | *E. COLI* FADM | BUTYRYL-COA | 0.027 ± 0.001 | CLOMBURG ET AL. (2012) |
| THIOESTERASE | *E. COLI* TESA | BUTYRYL-COA | 0.049 ± 0.002 | CLOMBURG ET AL. (2012) |
| THIOESTERASE | *E. COLI* TESB | BUTYRYL-COA | 0.101 ± 0.002 | CLOMBURG ET AL. (2012) |
| THIOESTERASE | *E. COLI* YBGC | BUTYRYL-COA | 0.045 ± 0.007 | CLOMBURG ET AL. (2012) |
| THIOESTERASE | *E. COLI* YCIA | BUTYRYL-COA | 2.9 ± 0.2 | CLOMBURG ET AL. (2012) |
| THIOESTERASE | *E. COLI* YDII | BUTYRYL-COA | 0.0917 ± 0.0007 | CLOMBURG ET AL. (2012) |
| THIOESTERASE | *E. COLI* FADM | DECANYL-COA | 0.034 ± 0.003 | CLOMBURG ET AL. (2012) |
| THIOESTERASE | *E. COLI* TESA | DECANYL-COA | 0.47 ± 0.04 | CLOMBURG ET AL. (2012) |
| THIOESTERASE | *E. COLI* TESB | DECANYL-COA | 0.6 ± 0.1 | CLOMBURG ET AL. (2012) |

TABLE 6-continued

Characterization of enzymes depicted in the filing.

| ENZYME CLASS | ENZYME | SUBSTRATE | MEASURED ACTIVITY PROTEIN/MIN) | SPECIFIC REFERENCE ($\mu$MOL/MG |
| --- | --- | --- | --- | --- |
| THIOESTERASE | E. COLI YBGC | DECANYL-COA | 0.06 ± 0.02 | CLOMBURG ET AL. (2012) |
| THIOESTERASE | E. COLI YCIA | DECANYL-COA | 3.7 ± 0.3 | CLOMBURG ET AL. (2012) |
| THIOESTERASE | E. COLI YDII | DECANYL-COA | 0.18 ± 0.04 | CLOMBURG ET AL. (2012) |
| THIOESTERASE | E. COLI TESB | ADIPYL-COA | 0.267 ± 0.002 | THIS WORK |
| THIOESTERASE | MUS MUSCULUS ACOT8 | ADIPYL-COA | 0.48 ± 0.02 | THIS WORK |

(N.D. means not detected)

Table 7 shows the results of testing several thiolases to ascertain that they will work to condense a ketoacyl-CoA with acetyl Co-A, thus forming a triketide.

TABLE 7

Screening thiolases for polyketoacyl-CoA thiolase activity through production of TAL via non-decarboxylative Claisen condensation between acetoacetyl-CoA (a ketoacyl-CoA serving as the primer) and acetyl-CoA (an acyl-CoA serving as the extender unit)

| Enzyme | Substrate | Measured specific activity ($\mu$mol/mg protein/min) | Reference |
| --- | --- | --- | --- |
| E. coli AtoB | Acetoacetyl-CoA + acetyl-CoA | N.D. | This work |
| E. coli FadA | Acetoacetyl-CoA + acetyl-CoA | N.D. | This work |
| E. coli PaaJ | Acetoacetyl-CoA + acetyl-CoA | N.D. | This work |
| Pseudomonas putida FadA | Acetoacetyl-CoA + acetyl-CoA | N.D. | This work |
| Pseudomonas putida FadAx | Acetoacetyl-CoA + acetyl-CoA | 0.052 ± 0.014 | This work |
| Acinetobacter sp. DcaF | Acetoacetyl-CoA + acetyl-CoA | 0.041 | This work |
| Streptomyces collinus FadA | Acetoacetyl-CoA + acetyl-CoA | 0.007 | This work |
| Ralstonia eutropha BktB | Acetoacetyl-CoA + acetyl-CoA | 0.00019 | This work |

N.D. means not detected.

Figure 18A:
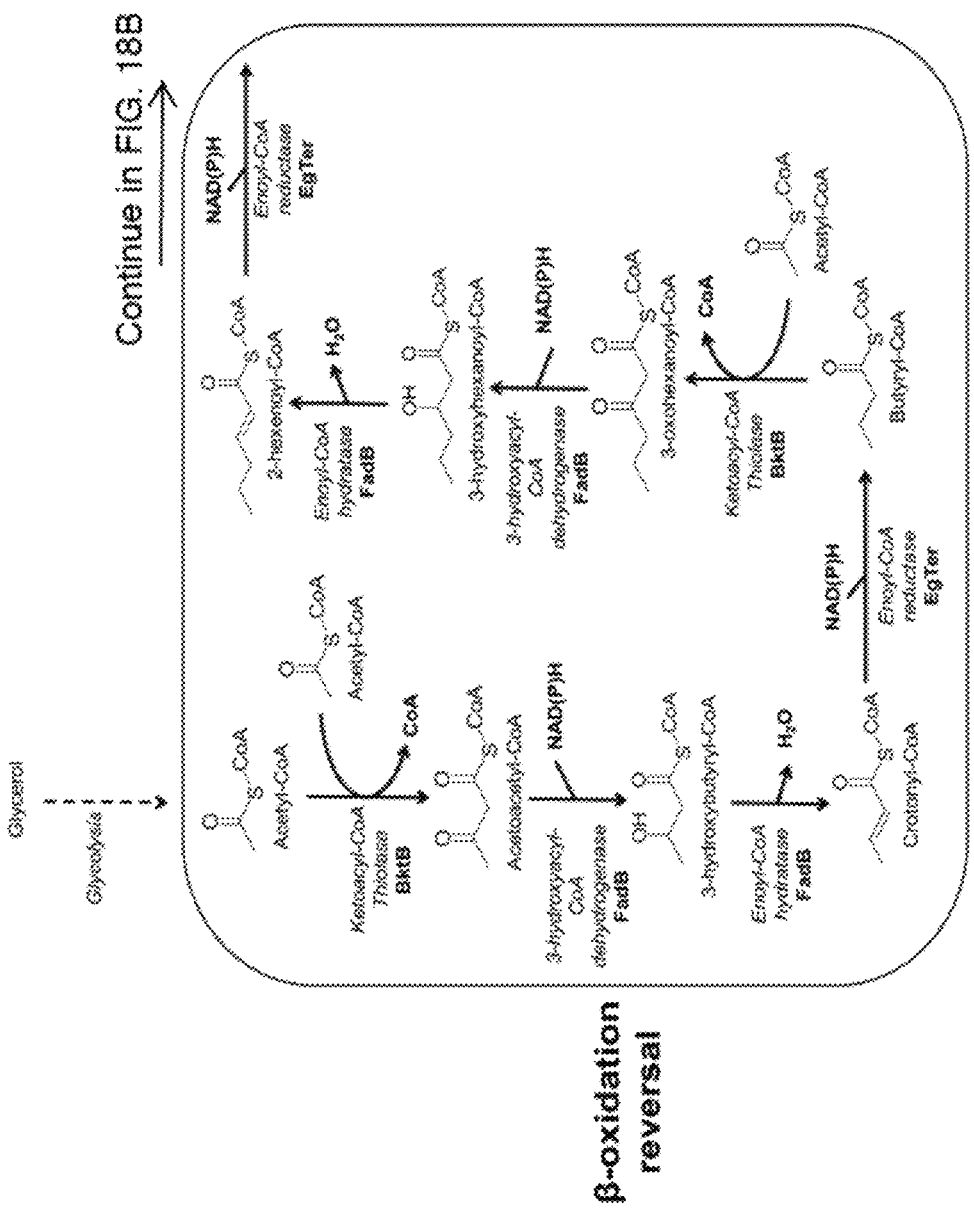
FIG. 18A-B: Example pathway for the synthesis of tetraketide derivative olivetolic acid. After two sequential non-decarboxylative Claisen condensation reactions of primer 3-oxooctanoyl-CoA and the extender unit acetyl-CoA catalyzed by polyketoacyl-CoA thiolase, triketoacyl-CoA 3,5,7-trioxododecanoyl-CoA is produced, which is then converted to olivetolic acid by olivetolic acid cyclase. 3-oxooctanoyl-CoA is supplied through non-decarboxylative Claisen condensation between primer hexanoyl-CoA and extender unit acetyl-CoA catalyzed by ketoacyl-CoA thiolase. Hexanoyl-CoA can be supplied through β-oxidation reversal with acetyl-CoA serving as primer and extender unit.
Figure 18B:
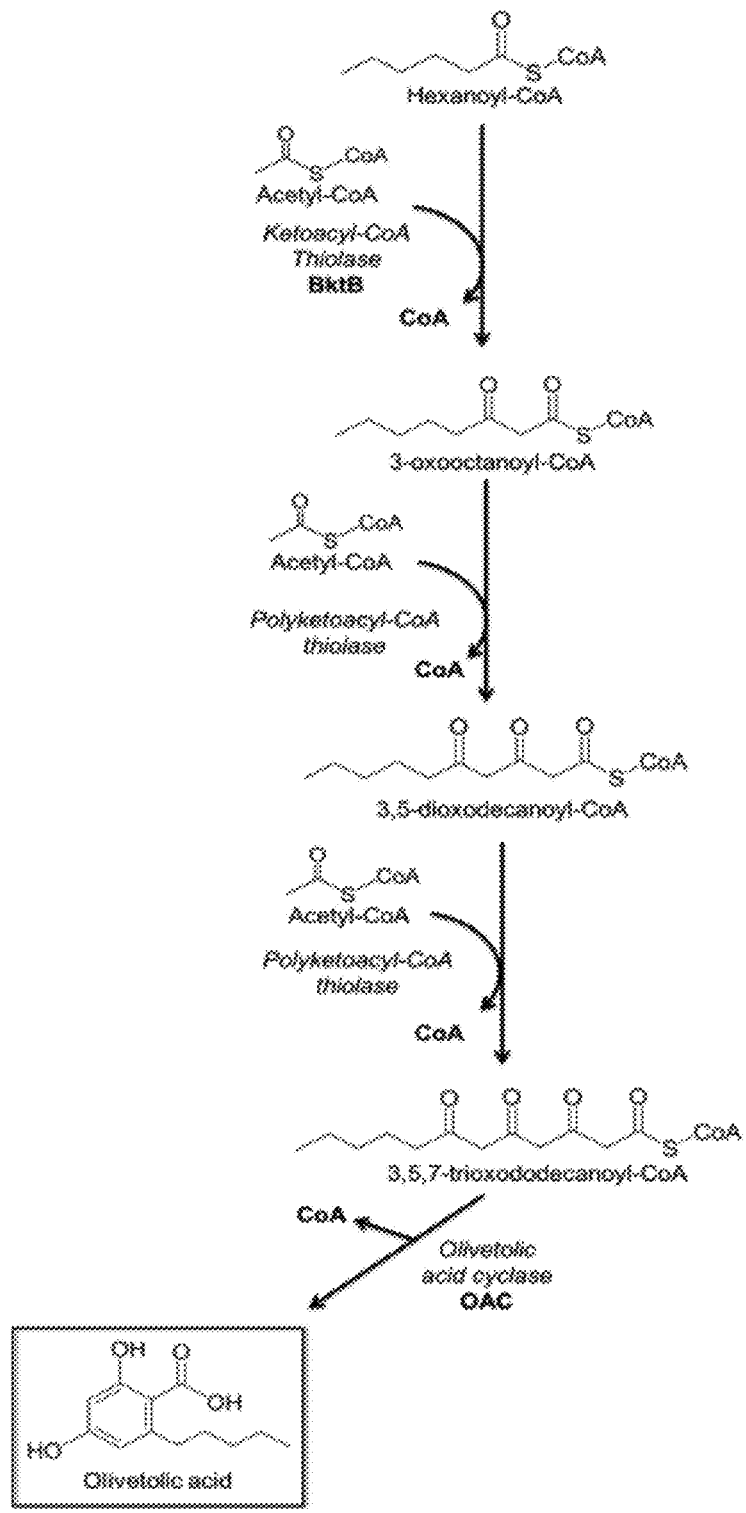

FIG. 18A-B shows an exemplary pathway for the synthesis of tetraketide derivative olivetolic acid using the disclosed methods. After two sequential non-decarboxylative Claisen condensation reactions of primer 3-oxooctanoyl-CoA and the extender unit acetyl-CoA catalyzed by polyketoacyl-CoA thiolase, triketoacyl-CoA 3,5,7-trioxododecanoyl-CoA is produced, which is then converted to olivetolic acid by olivetolic acid cyclase. 3-oxooctanoyl-CoA is supplied through non-decarboxylative Claisen condensation between primer hexanoyl-CoA and extender unit acetyl-CoA catalyzed by acetoacetyl-CoA thiolase. Hexanoyl-CoA can be supplied through β-oxidation reversal with acetyl-CoA serving as primer and extender unit.

Figure 19A:
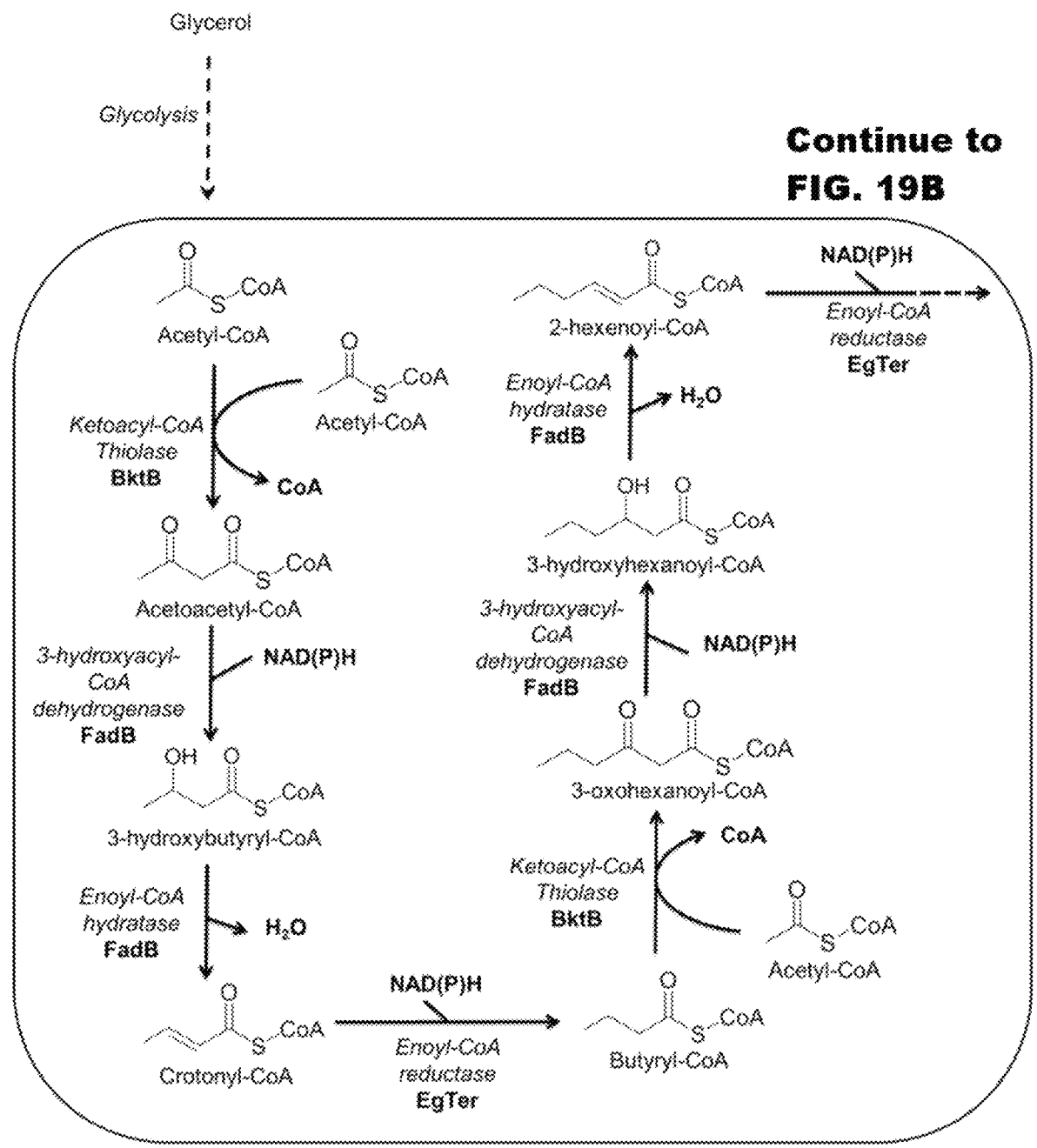
FIG. 19A-B: Example pathway for the synthesis of tetraketide derivative cannabigerolic acid (CBGA). After two sequential non-decarboxylative Claisen condensation reactions of primer hexanoyl-CoA and the extender unit acetyl-CoA catalyzed by polyketoacyl-CoA thiolase, triketoacyl-CoA 3,5,7-trioxododecanoyl-CoA is produced, which is then converted to olivetolic acid by olivetolic acid cyclase. Aromatic prenyltransferase transfers geranyl group from geranyl pyrophosphate to olivetolic acid, yielding cannabigerolic acid (CBGA). 3-oxooctanoyl-CoA is supplied through non-decarboxylative Claisen condensation between primer hexanoyl-CoA and extender unit acetyl-CoA catalyzed by ketoacyl-CoA thiolase. Hexanoyl-CoA can be supplied through β-oxidation reversal with acetyl-CoA serving as primer and extender unit. Geranyl pyrophosphate can be supplied through the endogenous pathway consisting methylerythritol phosphate pathway and the reaction of geranyl pyrophosphate synthase.
Figure 19B:
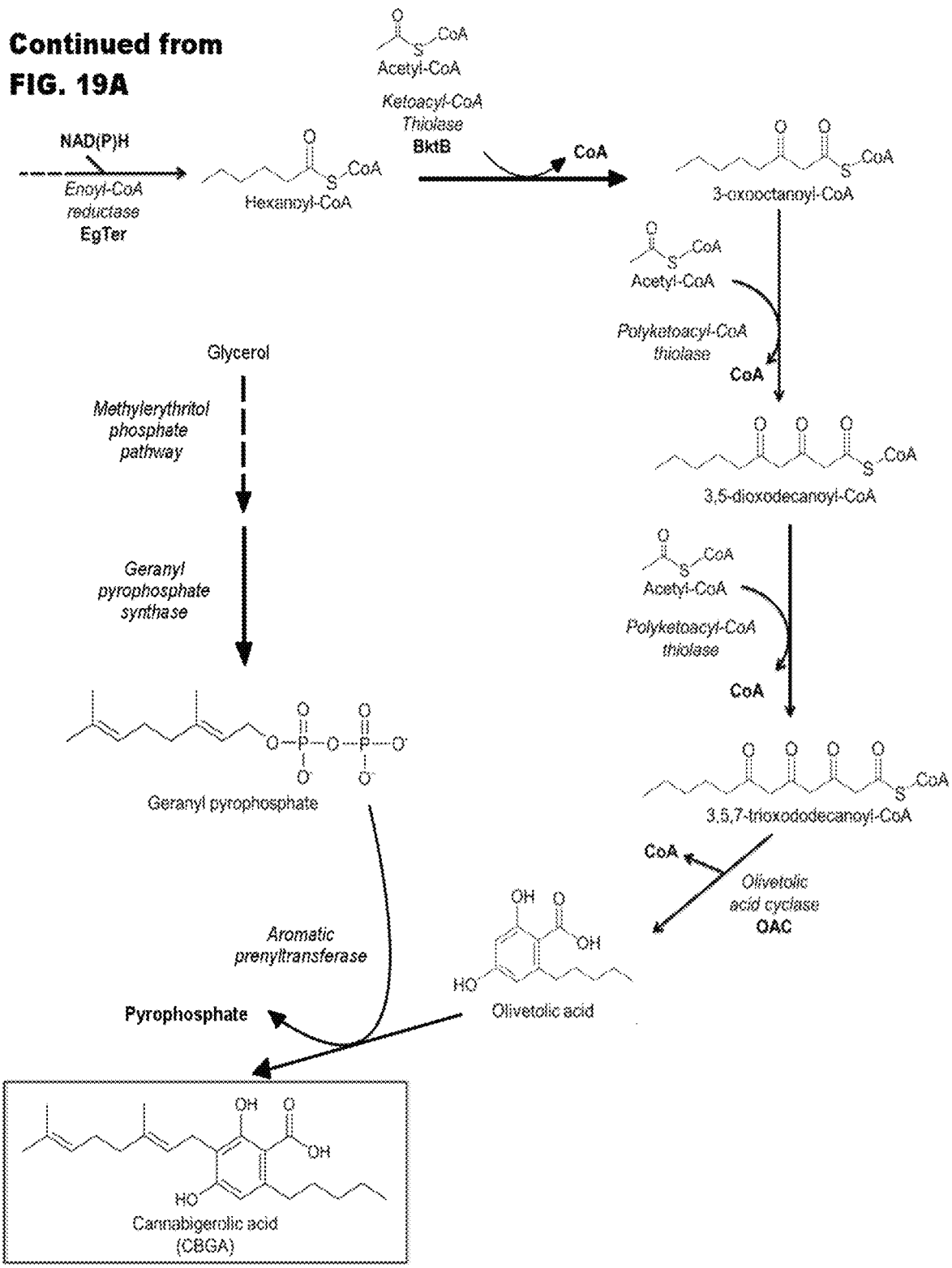

FIG. 19A-B shows an exemplary pathway for the synthesis of tetraketide derivative olivetolic acid using the disclosed methods. After two sequential non-decarboxylative Claisen condensation reactions of primer hexanoyl-CoA and the extender unit acetyl-CoA catalyzed by polyketoacyl-CoA thiolase, triketoacyl-CoA 3,5,7-trioxododecanoyl-CoA is produced, which is then converted to olivetolic acid by olivetolic acid cyclase. Aromatic prenyltransferase transfers geranyl group from geranyl pyrophosphate to olivetolic acid, yielding cannabigerolic acid (CBGA). 3-oxooctanoyl-CoA is supplied through non-decarboxylative Claisen condensation between primer hexanoyl-CoA and extender unit acetyl-CoA catalyzed by ketoacyl-CoA thiolase. Hexanoyl-CoA can be supplied through β-oxidation reversal with acetyl-CoA serving as primer and extender unit.

Figure 20:
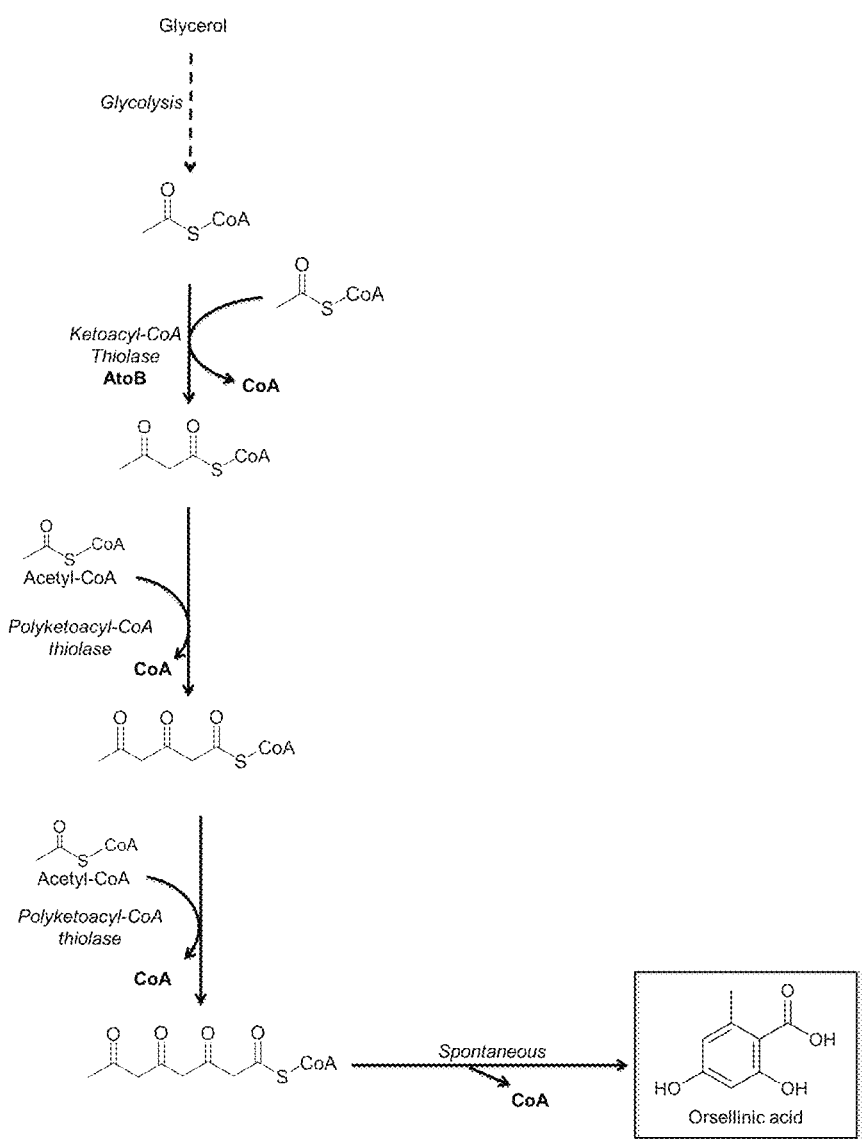
FIG. 20: Example pathway for the synthesis of tetraketide derivative orsellinic acid. After two sequential non-decarboxylative Claisen condensation reactions of primer acetoacetyl-CoA and the extender unit acetyl-CoA catalyzed by polyketoacyl-CoA thiolase, triketoacyl-CoA is produced, which is then spontaneously cyclized into orsellinic acid. Acetoacetyl-CoA can be supplied through non-decarboxylative Claisen condensation reaction between two acetyl-CoAs.

FIG. 20 shows an exemplary pathway for the synthesis of tetraketide derivative orsellinic acid using the disclosed methods. After two sequential non-decarboxylative Claisen condensation reactions of primer acetoacetyl-CoA and the extender unit acetyl-CoA catalyzed by polyketoacyl-CoA thiolase, triketoacyl-CoA is produced, which is then spontaneously cyclized into orsellinic acid. Acetoacetyl-CoA can be supplied through non-decarboxylative Claisen condensation reaction between two acetyl-CoAs.

Figure 21A:
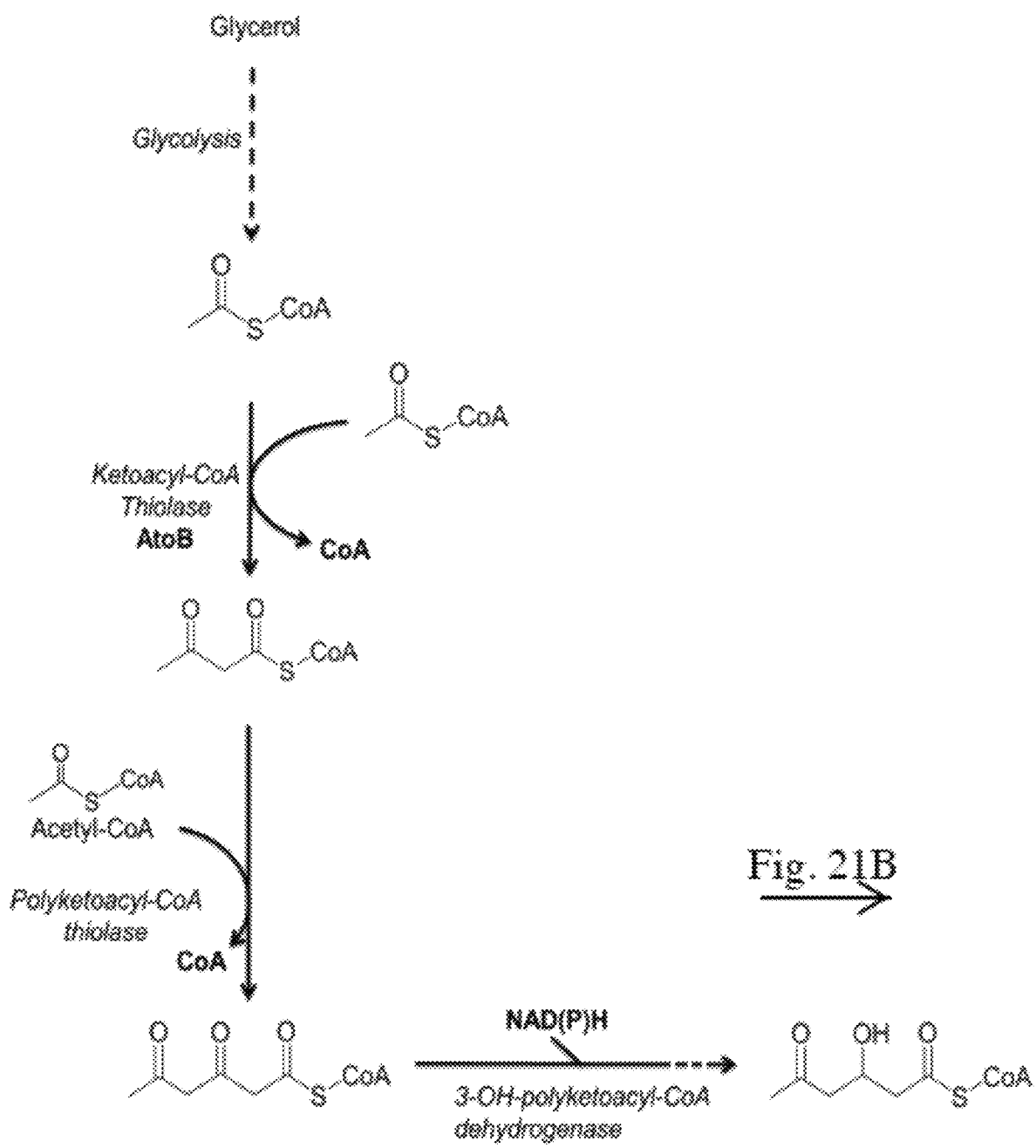
FIG. 21A-B: Example pathway for the synthesis of reduced tetraketide derivative 6-methyl salicylic acid. Polyketoacyl-CoA thiolase catalyzes non-decarboxylative Claisen condensation reaction with acetoacetyl-CoA as the primer and acetyl-CoA as the extender unit, yielding a diketoacyl-CoA (a triketide once the -CoA is removed). Sequential β-reduction reactions catalyzed by 3-OH-polyketoacyl-CoA dehydrogenase (end of FIG. 21A) and polyketoenoyl-CoA hydratase convert diketoacyl-CoA (beginning of FIG. 21B) to a 5-ketoenoyl-CoA. Polyketoacyl-CoA thiolase then catalyzes non-decarboxylative Claisen condensation reaction with 5-ketoenoyl-CoA as the primer and acetyl-CoA as the extender unit, and the condensation product is then spontaneously cyclized into 6-methylsalicylic acid. Acetoacetyl-CoA can be supplied through non-decarboxylative Claisen condensation reaction between two acetyl-CoAs.
Figure 21B:
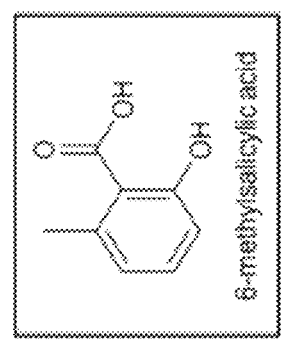
Figure 21B:
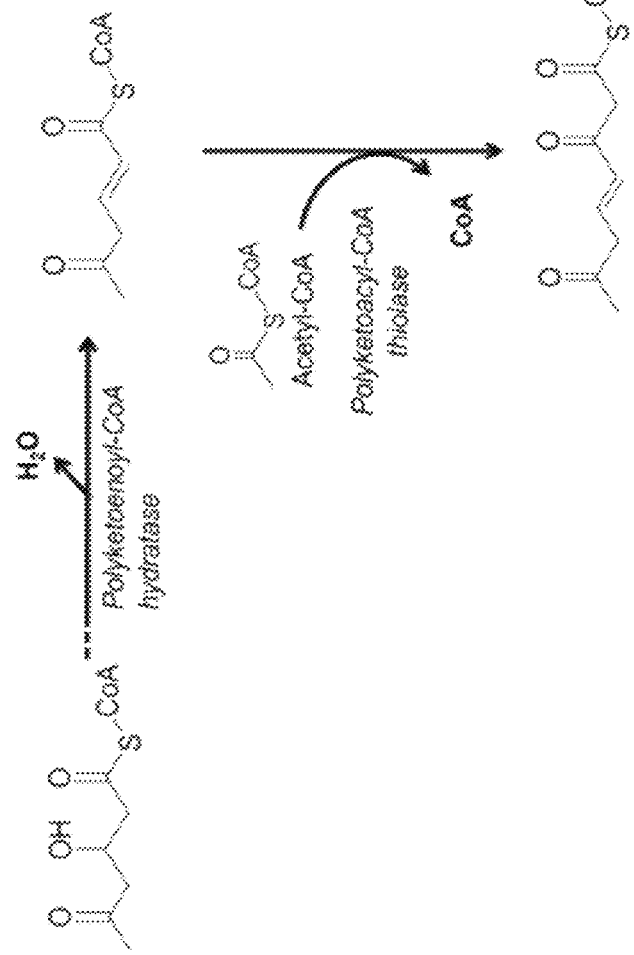

FIG. 21A-B shows an exemplary pathway for the synthesis of reduced tetraketide derivative 6-methylsalicylic acid using the disclosed methods. Polyketoacyl-CoA thiolase catalyzes non-decarboxylative Claisen condensation reaction with acetoacetyl-CoA as the primer and acetyl-CoA as the extender unit, yielding a diketoacyl-CoA. Sequential β-reduction reactions catalyzed by 3-OH-polyketoacyl-CoA dehydrogenase and polyketoenoyl-CoA hydratase convert diketoacyl-CoA to a 5-ketoenoyl-CoA. Polyketoacyl-CoA thiolase then catalyzes non-decarboxylative Claisen condensation reaction with 5-ketoenoyl-CoA as the primer and acetyl-CoA as the extender unit, and the condensation product is then spontaneously cyclized into 6-methylsalicylic acid. Acetoacetyl-CoA can be supplied through non-decarboxylative Claisen condensation reaction between two acetyl-CoAs.

Additional details are provided in the following experimental descriptions. Any single detail included therein (e.g., codon optimization or use of integrated genes) is intended for use in the appended claims in any combination(s) thereof. However, to repeat all possible combinations herein would be unnecessarily lengthy and duplicative.

In Vitro Synthesis of TAL

The purpose of this experiment was to clone, express and purify polyketoacyl-CoA thiolases and test their activity for in vitro synthesis of triacetic acid lactone (TAL) through non-decarboxylative Claisen condensation between acetoacetyl-CoA (a ketoacyl-CoA), serving as the primer, and acetyl-CoA, serving as the extender unit. The TAL synthesis reaction is shown in FIG. 7.

Nine enzymes were selected and tested for polyketoacyl-CoA thiolase activity: AtoB (NP_416728.1), FadA (YP_026272.1), PaaJ (NP_415915.1) from *E. coli*, ppFadA (AAK18168.1), FadAx (AAK18171.1) and PcaF (AAA85138.1) from *Pseudomonas putida*, DcaF (CAG68532.1) from *Acinetobacter* sp. ADP1, BktB (AAC38322.1) from *Ralstonia eutropha* and ScFadA (AAL10298.1) from *Streptomyces collinus*. AtoB, FadA and PaaJ were expressed in pCA24N- gene (-gfp) plasmids from the ASKA collection (Kitagawa et al., 2005). Genes encoding ppFadA, FadAx, PcaF, DcaF, BktB and ScFadA were codon optimized and synthesized by either GeneArt (Life Technologies, Carlsbad, Calif., USA) or GenScript (Piscataway, N.J.).

These genes were then amplified through PCR using primers to append homology on each end for recombination into the vector backbone with Phusion polymerase (Thermo Scientific, Waltham, Mass.) to serve as the gene insert. Plasmids were linearized by the appropriate restriction enzymes (New England Biolabs, Ipswich, Mass., USA) and recombined with the gene inserts using the In-Fusion HD Eco-Dry Cloning system (Clontech laboratories, Mountain View, Calif., USA). The mixture was subsequently transformed into Stellar competent cells (Clontech laboratories, Mountain View, Calif., USA). Transformants that grew on solid media (LB+Agar) supplemented with the appropriate antibiotic were isolated and screened for the gene insert by PCR. Plasmids from verified transformants were isolated and the sequence of the gene insert was further confirmed by DNA sequencing (Lone Star Labs, Houston, Tex.). Except for the expression of BktB, the sequence-confirmed plasmids were introduced to BL21(DE3) (Studier et al. 1986). The plasmid harboring the gene encoding BktB was introduced into AG1 (Agilent Technologies, Inc., Santa Clara, Calif.).

Primers used for genetic cloning in this example are shown in Table 8 below:

TABLE 8

List of primers used in Example 1.

| Seq. ID No. | Name | Sequence | Description |
| --- | --- | --- | --- |
| 1 | ppfadA-f1 | GCCAGGATCCGAATTCGAGCCTGAATCCGCGTGATG | ppfadA forward |
| 2 | ppfadA-r1 | CGCCGAGCTCGAATTCTTAAACACGTTCAAAAACG | ppfadA reverse |
| 3 | ppfadA-sf1 | CAGGACCTGTTTGGTGTTCG | ppfadA sequencing |
| 4 | ppfadA-sr1 | AAATGCCGGTTTCAGGCTGG | ppfadA sequencing |
| 5 | fadAx-f1 | GCCAGGATCCGAATTCGACCCTGGCAAATGATCCGAT | fadAx forward |
| 6 | fadAx-r1 | CGCCGAGCTCGAATTCTTAATACAGACATTCAACTGCC | fadAx reverse |
| 7 | fadAx-sf1 | GCACAGGCAAATGCCTTTAG | fadAx sequencing |
| 8 | fadAx-sr1 | TTCATCATCTTTGATCACGCG | fadAx sequencing |
| 9 | pcaF-f1 | GAGGAATAAACCATGCATGATGTCTTTATCTGTG | pcaF forward |
| 10 | pcaF-r1 | GATGATGATGGTCGACAACACGTTCAATAGCCAGAGC | pcaF reverse |
| 11 | pcaF-sf1 | CAGACAACGTGGCTGATGAC | pcaF sequencing |
| 12 | pcaF-sr1 | CAGTTTGGTCAGGGCTTCC | pcaF sequencing |
| 13 | dcaF-f1 | GCCAGGATCCGAATTCGCTGAACGCCTATATCTATGA | dcaF forward |
| 14 | dcaF-r1 | CGCCGAGCTCGAATTCTTAGCTCACATTTTCAATAACC | dcaF reverse |
| 15 | dcaF-sf1 | AAGCGCATATAGCCGTGATG | dcaF sequencing |
| 16 | dcaF-sr1 | TTTTGTTCGGGAAACGGGTG | dcaF sequencing |
| 17 | dcaF-sf2 | GCCAGCGGTATTAATGATGG | dcaF sequencing |
| 18 | dcaF-sr2 | TTTCTGACCTGCAACTTCGC | dcaF sequencing |
| 19 | bktB-f1 | CGCGCGGCAGCCATATGACGCGTGAAGTGGTAGTG | bktB forward |
| 20 | bktB-r1 | GCTCGACTCACTCGAGTCAGATACGCTCGAAGATGG | bktB reverse |

TABLE 8-continued

List of primers used in Example 1.

| Seq. ID No. | Name | Sequence | Description |
|---|---|---|---|
| 21 | bktB-sf1 | AAGGAATACGACATCTCGCG | bktB forward |
| 22 | bktB-sr1 | CGGTGTCGAAGGTCACGTC | bktB reverse |
| 23 | scfadA-f1 | GCCAGGATCCGAATTCAGCAGCGGTACAACCAGCAG | scfadA forward |
| 24 | scfadA-r1 | CGCCGAGCTCGAATTCTTATGCTTTCGGAACACGAAC | scfadA reverse |
| 25 | scfadA-sf1 | CAATGGCACATGATGGTCTG | scfadA sequencing |
| 26 | scfadA-sr1 | GGTAATGGTGCCATCTTTTGC | scfadA sequencing |

The codon-optimized ppfadA gene insert was PCR amplified with ppfadA-f1 and ppfadA-r1 primers and inserted into vector pCDFDuet-1 (Novagen, Darmstadt, Germany) cleaved by EcoRI (New England Biolabs, Ipswich, Mass.) through In-Fusion HD Eco-Dry Cloning system (Clontech laboratories, Mountain View, Calif.) to construct pCDF-ntH6-ppfadA. The sequence of the ppfadA gene insert was further confirmed by DNA sequencing (Lone Star Labs, Houston, Tex.) with usage of ppfadA-sf1 and ppfadA-sr1 sequencing primers. The protein was expressed with an n-terminal 6 His-tag.

The codon-optimized fadAx gene insert was PCR amplified with fadAx-f1 and fadAx-r1 primers and inserted into vector pCDFDuet-1 (Novagen, Darmstadt, Germany) cleaved by EcoRI (New England Biolabs, Ipswich, Mass.) through In-Fusion HD Eco-Dry Cloning system (Clontech laboratories, Mountain View, Calif.) to construct pCDF-ntH6-fadAx. The sequence of the fadAx gene insert was further confirmed by DNA sequencing (Lone Star Labs, Houston, Tex.) with usage of fadAx-sf1 and fadAx-sr1 sequencing primers. The protein was expressed with an n-terminal 6 His-tag.

The codon-optimized pcaF gene insert was PCR amplified with pcaF-f1 and pcaF-r1 primers and inserted into vector pTrcHis2A (Invitrogen, Carlsbad, Calif.) cleaved by NcoI and SalI (New England Biolabs, Ipswich, Mass., USA) through In-Fusion HD Eco-Dry Cloning system (Clontech laboratories, Mountain View, Calif.) to construct pTH-ctH6-pcaF. The sequence of the pcaF gene insert was further confirmed by DNA sequencing (Lone Star Labs, Houston, Tex.) with usage of pcaF-sf1 and pcaF-sr1 sequencing primers. The protein was expressed with a c-terminal 6 His-tag.

The codon-optimized dcaF gene insert was PCR amplified with dcaF-f1 and dcaF-r1 primers and inserted into vector pCDFDuet-1 (Novagen, Darmstadt, Germany) cleaved by EcoRI (New England Biolabs, Ipswich, Mass.) through In-Fusion HD Eco-Dry Cloning system (Clontech laboratories, Mountain View, Calif., USA) to construct pCDF-ntH6-dcaF. The sequence of the dcaF gene insert was further confirmed by DNA sequencing (Lone Star Labs, Houston, Tex.) with usage of dcaF-sf1, dcaF-sr1, dcaF-sf2 and dcaF-sr2 sequencing primers. The protein was expressed with an n-terminal 6 His-tag.

The codon-optimized bktB gene insert was PCR amplified with bktB-f1 and bktB-r1 primers and inserted into vector pUCBB-ntH6-eGFP (Vick et al. 2011) cleaved by NdeI and XhoI (New England Biolabs, Ipswich, Mass.) through In-Fusion HD Eco-Dry Cloning system (Clontech laboratories, Mountain View, Calif.) to construct pUCBB-ntH6-bktB. The sequence of the bktB gene insert was further confirmed by DNA sequencing (Lone Star Labs, Houston, Tex.) with usage of bktB-sf1 and bktB-sr1 sequencing primers. The protein was expressed with an n-terminal 6 His-tag.

The codon-optimized scfadA gene insert was PCR amplified with scfadA-f1 and scfadA-r1 primers and inserted into vector pCDFDuet-1 (Novagen, Darmstadt, Germany) cleaved by EcoRI (New England Biolabs, Ipswich, Mass.) through In-Fusion HD Eco-Dry Cloning system (Clontech laboratories, Mountain View, Calif.) to construct pCDF-ntH6-scfadA. The sequence of the scfadA gene insert was further confirmed by DNA sequencing (Lone Star Labs, Houston, Tex., USA) with usage of scfadA-sf1 and scfadA-sr1 sequencing primers. The protein was expressed with an n-terminal 6 His-tag.

For expression of polyketoacyl-CoA thiolases, cultures were grown in 25 mL of LB media in 125 mL flasks (Wheaton Industries, Inc., Millville, N.J.) at 37° C. A single colony of the desired strain was cultivated overnight (14-16 hrs) in 10 mL of LB medium in baffled flasks (Wheaton Industries, Inc., Millville, N.J.) with appropriate antibiotics and used as the inoculum (1 mL). Except for the expression of bktB, the cells were induced with 0.1 mM IPTG at an OD550~0.6, while bktB was expressed constitutively.

After post-induction growth for 4 h for ASKA strains, or 16 for other strains, the cells were collected and washed twice by 9 g/L sodium chloride solution. Cells were then re-suspended in lysis buffer (50 mM $NaH_2PO_4$, 300 mM NaCl, 10 mM imidazole, pH 8.0) to an OD~40. After re-suspension, the cells were disrupted using glass beads and then centrifuged at 4° C., 13000G, 10 min in an Optima L-80XP Ultracentrifuge (Beckman-Coulter, Schaumburg, Ill.). The resultant supernatant is the crude enzyme extract.

The His-tagged enzymes were then purified from crude extract by using Ni-NTA spin kit (Qiagen, Valencia, Calif.). The crude extracts are centrifuged (270G, 5 min) in spin columns, which have been equilibrated with lysis buffer and then washed twice by wash buffer (50 mM $NaH_2PO_4$, 300 mM NaCl, 20 mM imidazole, pH 8.0). After washing, the enzyme is eluted twice in elution buffer (50 mM $NaH_2PO_4$, 300 mM NaCl, 500 mM imidazole, pH 8.0). Both washing and elution steps are centrifuged at 890 g for 2 min. The purified enzyme extracts were then further concentrated and dialyzed through Amicon® Ultra 10K Device (Millipore, Billerica, Mass.). The enzymes were first filtered by centrifugation at 4° C., 14000G, 10 min, and then washed with 100 mM potassium phosphate, pH 7 buffer under the same centrifugation conditions. Finally, the concentrated and dialyzed enzymes were recovered through 4° C., 1000G, 2 min centrifugation.

The protein concentration was established using the Bradford Reagent (Thermo Scientific, Waltham, Mass.) using BSA as the protein standard. SDS-PAGE monitor of purified proteins was performed through XCell SureLock™ Mini-cell system (Invitrogen, Carlsbad, Calif.) with gels (12% acrylamide resolving gel and 4% acrylamide stacking gel) prepared through SureLock™ Mini-cell system (Invitrogen, Carlsbad, Calif.). The composition of the running buffer for SDS-PAGE was 3 g/L tris base, 14.4 g/L glycine and 1 g/L SDS in water.

Enzymatic assays for the formation of triacetic acid lactone (TAL) through polyketoacyl-CoA thiolase condensation between acetoacetyl-CoA and acetyl-CoA was performed in the presence of 100 mM potassium phosphate pH 7, 3 mM EDTA, 1 mM acetoacetyl-CoA and 1 mM acetyl-CoA in a total volume of 200 μL for DcaF, ScFadA and FadAx, or 220 μL for other tested thiolases at 25° C. For DcaF, ScFadA and FadAx, 4 μL of undiluted enzyme elute was added in the assay system, while for other thiolases, 24 μL of undiluted enzymes were added. Activity was monitored in a Biomate 5 Spectrophotometer (Thermo Scientific, Waltham, Mass.) by the increase of TAL at 298 nm using an extinction coefficient of 2.9443 $mM^{-1}$ $cm^{-1}$ measured through calibration of TAL standards. Two controls were also tested for each assay: one without the addition of substrates acetoacetyl-CoA and acetyl-CoA; one without the addition of enzyme. TAL formation in assay samples was then identified via HPLC using a Shimadzu LC-20AD HPLC system with an SPD-20A dual-wavelength UV-vis detector and a Phenomonex Luna C18 column (25 cm×4.6 mm, 5 μm) (Tang et al. 2013). The following elution profile (Xie et al. 2006) was used: solvent A, 1% (v/v) acetic acid in water; solvent B, 1% (v/v) acetic acid in acetonitrile; gradient: 5% B (0-5 min), 5-15% B (5-18 min), 15-100% B (18-23 min), 100% B (23-30 min); flow rate 1.0 mL/min; wavelength, 300 nm.

Figure 10:
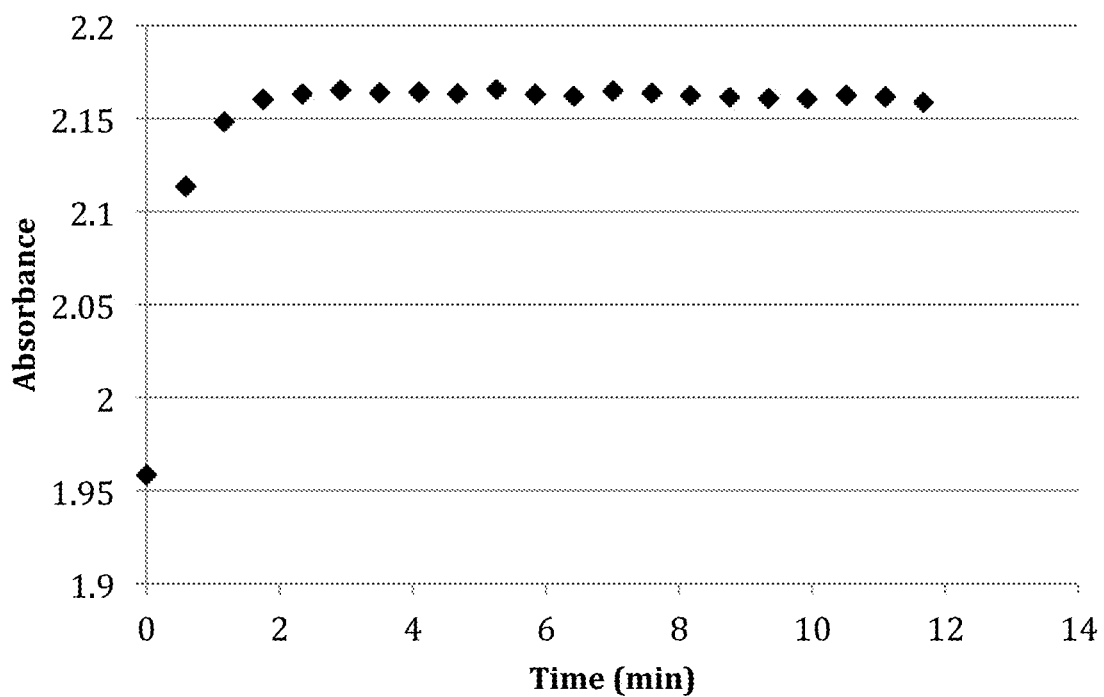
FIG. 10: Time profile for increase in absorbance at 298 nm due to production of TAL by *Pseudomonas putida* polyketoacyl-CoA thiolase PcaF.
Figure 11:
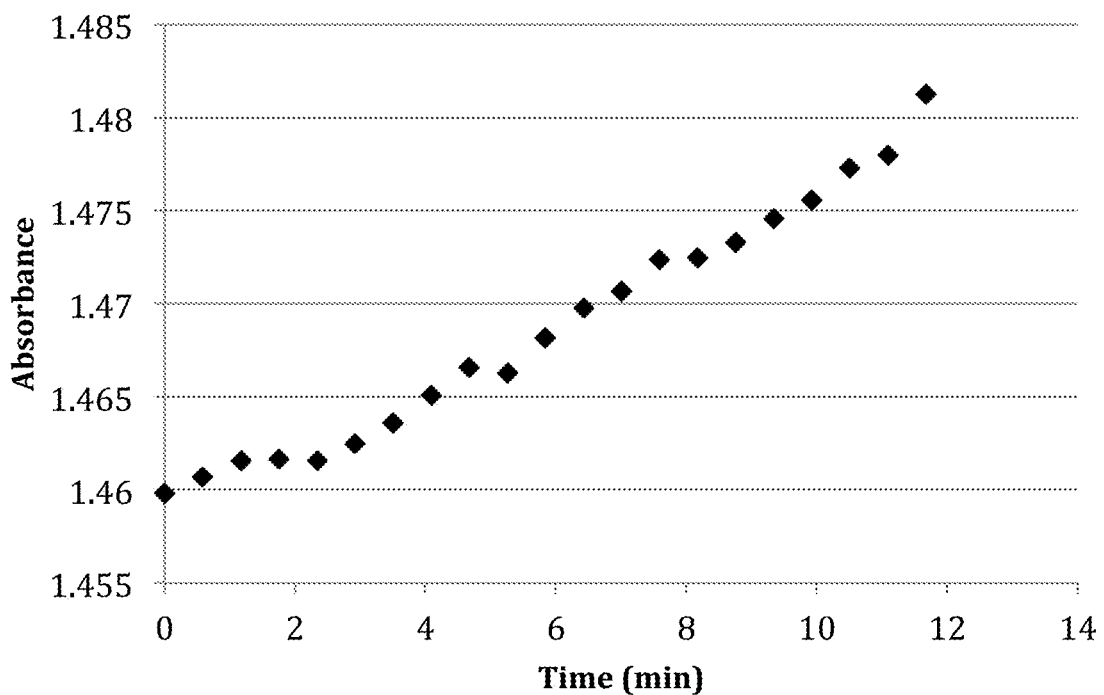
FIG. 11: Time profile for increase in absorbance at 298 nm due to production of TAL in the assay sample of *Ralstonia eutropha* polyketoacyl-CoA thiolase BktB.
Figure 12:
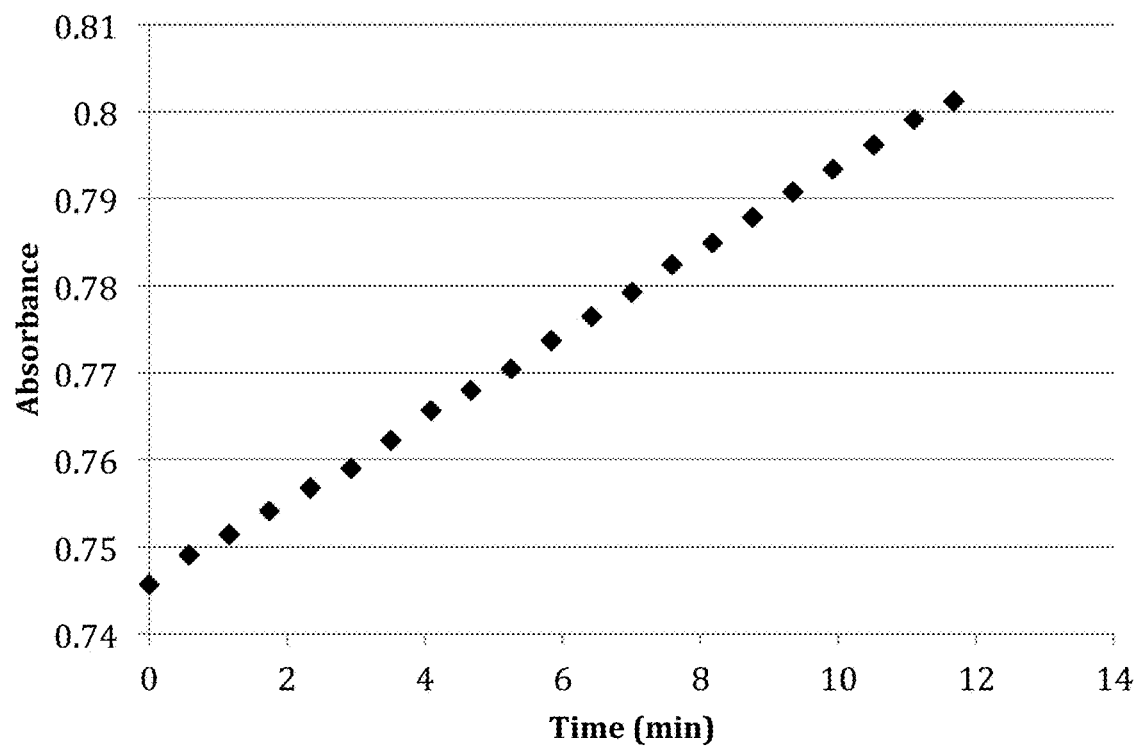
FIG. 12: Time profile for increase in absorbance at 298 nm due to production of TAL in the assay sample of *Streptomyces collinus* polyketoacyl-CoA thiolase FadA.
Figure 13:
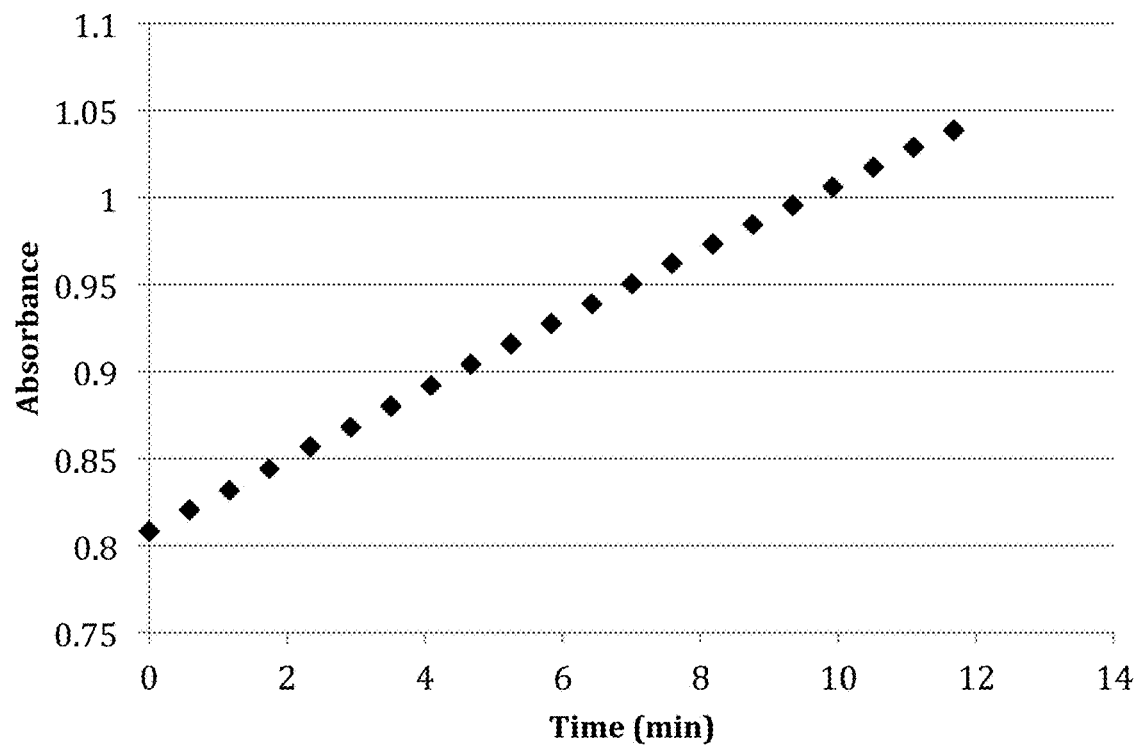
FIG. 13: Time profile for increase in absorbance at 298 nm due to production of TAL in the assay sample of *Acinetobacter* sp. polyketoacyl-CoA thiolase DcaF.
Figure 14:
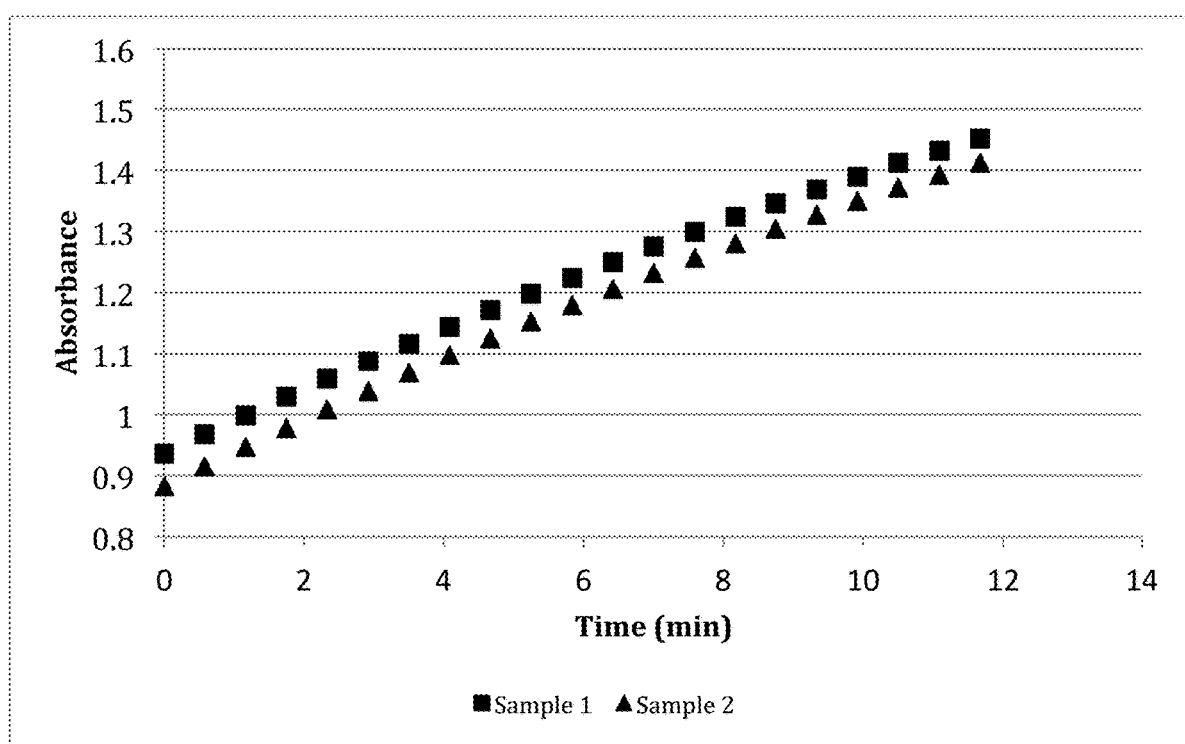
FIG. 14: Time profile for increase in absorbance at 298 nm due to production of TAL in the assay sample of *Pseudomonas putida* polyketoacyl-CoA thiolase FadAx.

Among the tested enzymes for polyketoacyl-CoA thiolase activity (AtoB, FadA, PaaJ, PpFadA, FadAx, PcaF, DcaF, BktB and ScFadA), samples of AtoB, FadA, PaaJ and PpFadA did not show the increase in absorbance at 298 nm expected from the production of TAL. PcaF showed a sharp increase in absorbance at of 298 nm first, then remained flat at saturated level, as shown in FIG. 10, indicating the synthesis of TAL. BktB, ScFadA, DcaF and FadAx also showed linear increase in absorbance at 298 nm, indicating their activity in the synthesis of TAL, as shown in FIG. 11-14 respectively. No controls showed the observed increase in absorbance at 298 nm.

Figure 9:
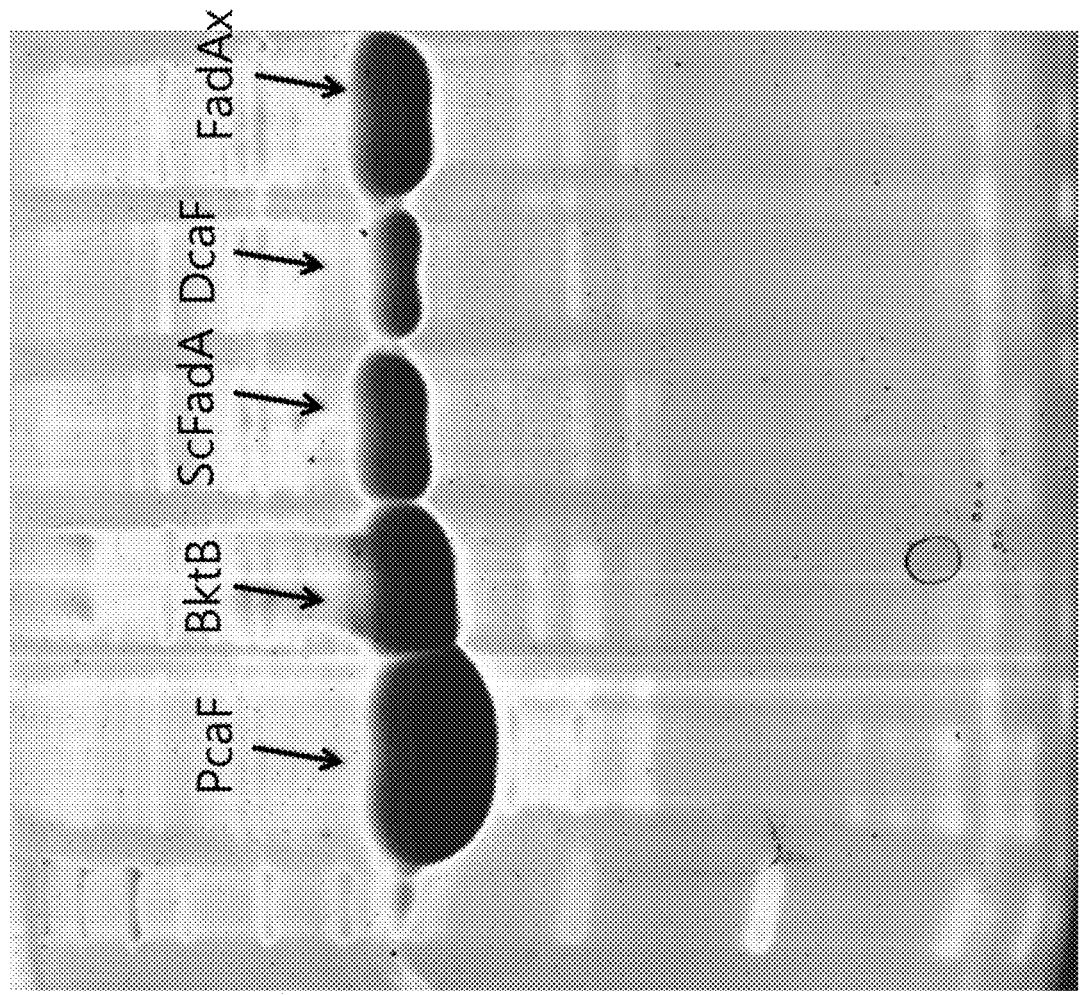
FIG. 9: SDS-PAGE gel showing purified polyketoacyl-CoA thiolases PcaF, BktB, ScFadA, DcaF and FadAx tested for in vitro TAL synthesis and in vitro dehydroacetic acid synthesis.

The SDS-PAGE gel of purified PcaF, BktB, ScFadA, DcaF and FadAx, (all the enzymes that showed the increase in absorbance 298 nm) in the assay of in vitro TAL synthesis, is shown in FIG. 9. The measured TAL synthesis specific activities of tested polyketoacyl-CoA thiolases calculated through linear 298 nm absorbance increase rates of their assay samples were as shown in Table 9:

TABLE 9

Identification of polyketoacyl-CoA thiolases for TAL synthesis through non-decarboxylative Claisen condensation between acetoacetyl-CoA (a ketoacyl-CoA acting as primer) and acetyl-CoA (an acyl-CoA acting as extender unit.

| Enzyme | Substrate | Measured specific activity (μmol/mg protein/min) | Reference |
|---|---|---|---|
| E. coli AtoB | Acetoacetyl-CoA + acetyl-CoA | N.D. | This work |
| E. coli FadA | Acetoacetyl-CoA + acetyl-CoA | N.D. | This work |
| E. coli PaaJ | Acetoacetyl-CoA + acetyl-CoA | N.D. | This work |
| Pseudomonas putida FadA | Acetoacetyl-CoA + acetyl-CoA | N.D. | This work |
| Pseudomonas putida PcaF | Acetoacetyl-CoA + acetyl-CoA | N.D. | This work |
| Pseudomonas putida FadAx | Acetoacetyl-CoA + acetyl-CoA | 0.052 ± 0.014 | This work |
| Acinetobacter sp. DcaF | Acetoacetyl-CoA + acetyl-CoA | 0.041 | This work |
| Streptomyces collinus FadA | Acetoacetyl-CoA + acetyl-CoA | 0.007 | This work |
| Ralstonia eutropha BktB | Acetoacetyl-CoA + acetyl-CoA | 0.00019 | This work |

N.D. means not detected.

Despite the increase in absorbance at 298 nm, the specific activity of PcaF on TAL synthesis was not calculated as the increase of absorbance was not linear.

Replicate assay samples of FadAx for in vitro TAL synthesis were then analyzed through RP-HPLC along with 0.31 mM TAL standard. Both samples showed the peak at the same retention time with that of TAL standard, indicating TAL formation in these samples. The quantified TAL titer in sample 1 was 0.0396 mM and the titer in sample 2 was 0.0346 mM.

In Vivo Synthesis of TAL

The purpose of this experiment was to clone and express polyketoacyl-CoA thiolases in an *Escherichia coli* strain already overexpressing a type II thiolase-acetoacetyl-CoA thiolase AtoB (NP_416728.1) for in vivo microbial synthesis of triacetic acid lactone (TAL) through polyketoacyl-CoA thiolase-catalyzed non-decarboxylative Claisen condensation between a ketoacyl-CoA (acetoacetyl-CoA), serving as the primer, and acetyl-CoA, serving as the extender unit. Acetoacetyl-CoA was supplied through AtoB-catalyzed non-decarboxylative Claisen condensation between two acetyl-CoAs. Acetyl-CoA was supplied through glycolysis from carbon source glycerol.

JST06(DE3) atoB$^{CT5}$ served as the host strain for the in vivo production of TAL. JST06(DE3) (MG1655(DE3) ΔldhA ΔpoxB Δpta ΔadhE ΔfrdA ΔyciA ΔybgC ΔydiI ΔtesA ΔfadM ΔtesB) (Cheong et al. 2016) is an *E. coli* strain deficient in mixed-acid fermentation pathways due to deletions of genes ldhA, poxB, pta, adhE and frdA, which maximizes the supply of acetyl-CoA, and deletions of genes encoding major thioesterases (yciA, ybgC, ydiI, tesA, fadM and tesB), which minimize the hydrolysis of acetyl-CoA and acetoacetyl-CoA.

The genotype atoB$^{CT5}$ refers to chromosomal atoB gene under the p$^{CT5}$ promoter for controlled induction by cumate. To enable the cumate-inducible chromosomal expression of atoB gene in JST06(DE3), *E. coli* atoB gene was first PCR amplified from genomic DNA extracted through Genomic DNA Purification kit (Promega, Fitchburg, Wis., USA), digested with BglII and NotI (New England Biolabs, Ipswich, Mass., USA), and ligated by T4 ligase (Invitrogen, Carlsbad, Calif.) into pUCBB-ntH6-eGFP (Vick et al. 2011) that was previously digested with BglII and NotI to produce pUCBB-$P^{CT5}$-atoB. The resulting ligation products were used to transform E. coli DH5α (Invitrogen, Carlsbad, Calif.), and positive clones identified by PCR were confirmed by DNA sequencing.

To integrate the cumate-controlled atoB construct into the chromosome of JST06(DE3), first the cumate repressor (cymR), promoter/operator regions ($P^{CT5}$), and respective ORFs were PCR amplified, as was the kanamycin drug construct via pKD4 (Datsenko and Wanner, 2000). These respective products were linked together via overlap extension PCR to create a final chromosomal targeting construct. Integration of the cumate-controlled constructs was achieved via standard recombineering protocols by using strain HME45 and selection on LB drug plates (Thomason et al. 2001). The primers used in the construction of JST06 (DE3) atoB$^{CT5}$ are listed as in Table 10 below:

Co., Inc., Edison, N.J.) at 200 rpm and 37° C. When optical density (550 nm, $OD_{550}$) reached ~0.3-0.5, 5 µM isopropyl β-D-1-thiogalactopyranoside (IPTG) was added for plasmid gene induction. For induction of controlled chromosomal expression of atoB constructs, 0.1 mM cumate was also added. Flasks were then incubated under the same conditions for 48 hours post-induction. After the fermentation, the supernatant obtained through 5000G, 5 min centrifuge in an Optima L-80XP Ultracentrifuge (Beckman-Coulter, Schaumburg, Ill.) of 2 mL culture was collected as the sample for HPLC analysis.

The quantification of TAL was performed via ion-exclusion HPLC using a Shimadzu Prominence SIL 20 system (Shimadzu Scientific Instruments, Inc., Columbia, Md.) equipped with an HPX-87H organic acid column (Bio-Rad, Hercules, Calif.) with operating conditions to optimize peak separation (0.3 mL/min flow rate, 30 mM $H_2SO_4$ mobile phase, column temperature 42° C.). Concentration of TAL in fermentation samples was determined through calibration to known TAL standards (1, 0.5, 0.25 and 0.1 g/L).

TABLE 10

List of primers used in the construction of strain JST06(DE3) atoB$^{CT5}$

| Seq. ID No. | Name | Sequence |
|---|---|---|
| 27 | kan-homatoE-L | TTGGTTTAACGCTGTTCTGACGGCACCCCTACAAACAGAAGGAATATAAACATATGAATATCCTCCTTA |
| 28 | kan-ovcymatoB-R | TCTGAAATTCTGCCTCGTGAGTGTAGGCTGGAGCTGCTTCG |
| 29 | cym-pCTC-atoB-ovkan-L | CGAAGCAGCTCCAGCCTACACTCACGAGGCAGAATTTCAGA |
| 30 | atoBintrecomb-R | GCCAGCCCGCTTTTTAAC |

Five polyketoacyl-CoA thiolases were selected the based on their ability to catalyze the synthesis of TAL in in vitro and overexpressed in JST06(DE3) atoB$^{CT5}$ strain: FadAx (AAK18171.1) and PcaF (AAA85138.1) from Pseudomonas putida, DcaF (CAG68532.1) from Acinetobacter sp. ADP1, BktB (AAC38322.1) from Ralstonia eutropha and ScFadA (AAL10298.1) from Streptomyces collinus. Codon-optimized genes encoding Pseudomonas putida FadAx, Acinetobacter sp. DcaF, and Streptomyces collinus FadA were cloned into the pCDFDuet-1 vector (Novagen, Darmstadt, Germany). Cloning and isolation of confirmed plasmids was conducted as described above. The sequence confirmed plasmids were then introduced to competent JST06(DE3) atoB$^{CT5}$ cells.

MOPS minimal medium (Neidhardt et al., 1974) with 125 mM MOPS and $Na_2HPO_4$ in place of $K_2HPO_4$ (2.8 mM), supplemented with 20 g/L glycerol, 10 g/L tryptone, 5 g/L yeast extract, 100 µM $FeSO_4$, 5 mM calcium pantothenate, 5 mM $(NH_4)_2SO_4$, and 30 mM $NH_4Cl$ was used for fermentations. Antibiotics (50 µg/mL carbenicillin and 50 µg/mL spectinomycin) were included when appropriate. All chemicals were obtained from Fisher Scientific Co. (Pittsburgh, Pa.) and Sigma-Aldrich Co. (St. Louis, Mo.).

Fermentations were performed in 25 mL Pyrex Erlenmeyer flasks (narrow mouth/heavy duty rim, Corning Inc., Corning, N.Y.) filled with 20 mL fermentation medium and sealed with foam plugs filling the necks. A single colony of the desired strain was cultivated overnight (14-16 hrs) in LB medium with appropriate antibiotics and used as the inoculum (1%). After inoculation, flasks were incubated in a NBS I24 Benchtop Incubator Shaker (New Brunswick Scientific Among the tested strains, JST06(DE3) atoB$^{CT5}$ overexpressing BktB showed the highest production of TAL at 0.36 g/L, demonstrating the in vivo synthesis of TAL using a polyketoacyl-CoA thiolase through non-decarboxylative Claisen condensation between acetoacetyl-CoA and acetyl-CoA. It also indicates that, JST06(DE3) atoB$^{CT5}$ is a suitable host strain for supplying acetoacetyl-CoA and acetyl-CoA. As such, this demonstrates the use of an acetoacetyl-CoA thiolase/ketoacyl-CoA thiolase for the generation of the ketoacetyl-CoA primer in combination with a polyketoacyl-CoA thiolase for the subsequent non-decarboxylative condensation of acetyl-CoA with said ketoacetyl-CoA primer to form a polyketoacyl-CoA.

In Vitro Synthesis of Dehydroacetic Acid

The purpose of this experiment was to clone, express and purify polyketoacyl-CoA thiolases and test their activities for in vitro synthesis of dehydroacetic acid through non-decarboxylative Claisen condensation between two acetoacetyl-CoAs (ketoacyl-CoAs), one serving as the primer, and the other serving as the extender unit. The dehydroacetic acid synthesis reaction is shown in FIG. 8.

Three polyketoacyl-CoA thiolases were selected based on their ability to catalyze the synthesis of TAL in vitro and tested: FadAx (AAK18171.1) and PcaF (AAA85138.1) from Pseudomonas putida, and ScFadA (AAL10298.1) from Streptomyces collinus. Cloning and isolation of confirmed plasmids was conducted as described above.

Following expression and purification of polyketoacyl-CoA thiolases as described above, the concentrated and dialyzed enzymes were recovered through 4° C., 1000G, 2 min centrifugation. The protein concentration was established using the Bradford Reagent (Thermo Scientific, Waltham, Mass.) using BSA as the protein standard. SDS-PAGE monitor of purified proteins was performed through XCell SureLock™ Mini-cell system (Invitrogen, Carlsbad, Calif.) with gels (12% acrylamide resolving gel and 4% acrylamide stacking gel) prepared through SureLock™ Mini-cell system (Invitrogen, Carlsbad, Calif.). The composition of the running buffer for SDS-PAGE was 3 g/L tris base, 14.4 g/L glycine and 1 g/L SDS in water. The SDS-PAGE gel can be seen in FIG. 9.

Dehydroacetic acid synthesis through polyketoacyl-CoA thiolase condensation between two molecules of acetoacetyl-CoA was performed in the presence of 100 mM potassium phosphate pH 7, 3 mM EDTA and 1 mM acetoacetyl—in a total volume of 200 µL for FadAx, or 220 µL for DcaF and PcaF at 25° C. For FadAx, 4 µL of undiluted enzyme elute was added in the assay system, while for PcaF and DcaF, 24 µL of undiluted enzymes were added. Activity was monitored in a Biomate 5 Spectrophotometer (Thermo Scientific, Waltham, Mass.) by the increase in absorbance at 312 nm (absorbance of dehydroacetic acid) using an extinction coefficient of 4.8567 $mM^{-1}$ $cm^{-1}$ measured through calibration of dehydroacetic acid standards. Two controls were also tested for each assay: one without the addition of substrate acetoacetyl-CoA; one without the addition of enzyme.

Among the tested polyketoacyl-CoA thiolases (FadAx, PcaF and DcaF), sample of DcaF did not show the increase of 312 nm absorbance. The sample of PcaF showed the sharp increase of 312 nm absorbance at first then remained flat at saturated level, as shown in FIG. 16, indicating its activity of dehydroacetic acid synthesis. The sample of FadAx first showed linear increase in absorbance at 312 nm, and then the increase rate diminished, indicating their activities on dehydroacetic acid synthesis, as shown in FIG. 17. No controls showed the increase of 312 nm wavelength. The measured specific activity of PcaF was calculated from the increase rate at the initial phase (0.044 µmol/min/mg), which is close to its measured specific activity on TAL synthesis (0.052±0.014 µmol/min/mg) as shown above.

This demonstrates the ability of certain polyketoacyl-CoA thiolases to condense two ketoacyl-CoA molecules (one as the primer and one as the extender) for the formation of polyketoacyl-CoAs with different functionalization compared to the use of acetyl-CoA as the priming molecule. Thus, polyketoacyl-CoA thiolases not only use ketoacyl-CoAs (e.g. acetoacetyl-CoA) as a primer, but also as extender units.

(Prophetic) In Vivo Synthesis of Dehydroacetic Acid

The purpose of this experiment is to clone and express polyketoacyl-CoA thiolases in an *Escherichia coli* strain already overexpressing acetoacetyl-CoA thiolase AtoB (NP_416728.1, EC 2.3.1.9) for in vivo microbial synthesis of dehydroacetic acid through polyketoacyl-CoA thiolase-catalyzed non-decarboxylative Claisen condensation between two acetoacetyl-CoAs (ketoacyl-CoAs), one serving as the primer and the other serving as the extender unit. Acetoacetyl-CoA is supplied through AtoB-catalyzed non-decarboxylative Claisen condensation between two acetyl-CoAs. Acetyl-CoA is supplied through glycolysis from a carbon source such as glycerol, or sugars.

JST06(DE3) atoB$^{CT5}$ serves as the host strain for the in vivo production of dehydroacetic acid. JST06(DE3) (MG1655(DE3) ΔldhA ΔpoxB Δpta ΔadhE ΔfrdA ΔyciA ΔybgC ΔydiI ΔtesA ΔfadM ΔtesB) (Cheong et al. 2016) is an *E. coli* strain deficient in mixed-acid fermentation pathways due to deletions of genes ldhA, poxB, pta, adhE and frdA, which maximize the supply of acetyl-CoA, and deletions of genes encoding major thioesterases (yciA, ybgC, ydiI, tesA, fadM and tesB), which minimize the hydrolysis of acetyl-CoA and acetoacetyl-CoA. This strain is constructed as described above, with the primers used in the construction of JST06(DE3) atoB$^{CT5}$ listed in Table 10.

Two polyketoacyl-CoA thiolases are selected and overexpressed in JST06(DE3) atoB$^{CT5}$ strain: FadAx (AAK18171.1) and PcaF (AAA85138.1) from *Pseudomonas putida*. These polyketoacyl-CoA thiolases are chosen because they showed the ability to catalyze the synthesis of dehydroacetic acid in in vitro assays as shown above. Genes encoding *Pseudomonas putida* FadAx and PcaF are cloned into appropriate vectors as described above and transformed into the appropriate host strain.

Fermentations are conducted as described above using a media such as MOPS minimal medium (Neidhardt et al., 1974). Inoculation and induction are as described above with flasks then incubated for 48 hours post-induction. After the fermentation, the supernatant obtained through 5000G, 5 min centrifuge in an Optima L-80XP Ultracentrifuge (Beckman-Coulter, Schaumburg, Ill.) of 2 mL culture is prepared for GC-FID analysis.

The supernatant aliquots of 2 mL are transferred to 5 mL glass vials (Fisher Scientific Co., Pittsburgh, Pa.). Samples were supplemented with 2 mg of 4-pentylbenzoic acid as internal standard and extracted with 2 mL of hexane. 80 µL of 50% $H_2SO_4$ and 340 µL of 30% NaCl solution are also added for pH and ionic strength adjustment, respectively. Vials are tightly closed, vortexed for 30 s, and mixed in a Glas-Col rotator (Glas-Col, Terre Haute, Ind.) at 60 rpm for 2 h. Samples are then vortexed again for 30 s and centrifuged at 8000 rpm at 4° C. for 1 min. Aliquots of 1.5 mL of the organic layer were transferred to 2 mL borosilicate glass vials with PTFE/silicone screw caps (Fisher Scientific Co., Pittsburgh, Pa.) and mixed with 100 µL of pyridine and 100 µL of N,O-bis(trimethylsilyl)trifluoroacetamide (BSTFA). Samples are incubated in sealed vials at 70° C. for 60 min using an AccuBlock Digital Dry Bath (LabNet, Woodbridge, N.J.), and silylated samples are analyzed via GC-FID quantification analysis.

The quantification of dehydroacetic acid is performed in a Varian CP-3800 gas chromatograph (Varian Associates, Inc., Palo Alto, Calif.), equipped with a flame ionization detector (GC-FID) and an HP-INNOWax capillary column (0.32 mm internal diameter, 0.50 µm film thickness, 30 m length; Agilent Technologies, Inc., Santa Clara, Calif.), following the method: 100° C. initial column temperature, 15° C./min to 300° C., and 300° C. held for 8 min. Helium (1 mL/min, Matheson Tri-Gas, Longmont, Colo.) is used as the carrier gas. The injector and detector are maintained at 280 and 300° C., respectively. A 1 µL sample is injected in splitless injection mode.

(Prophetic) In Vivo Synthesis of Olivetolic Acid

The purpose of this experiment is to clone and express polyketoacyl-CoA thiolases along with olivetolic acid cyclase OAC (AFN42527.1) from *Cannabis sativa* in an *Escherichia coli* strain already overexpressing polyketoacyl-CoA thiolase BktB (AAC38322.1) from *Ralstonia eutropha*, 3-hydroxyacyl-CoA dehydrogenase and enoyl-CoA hydratase multifunctional enzyme FadB from *E. coli* (NP_418288.1) and enoyl-CoA reductase Ter from *Euglena gracilis* (abbreviated egTER) (Q5EU90.1) for in vivo microbial synthesis of olivetolic acid.

Polyketoacyl-CoA thiolase catalyzes two sequential non-decarboxylative Claisen condensation reactions with 3-oxooctanoyl-CoA as the initial primer and acetyl-CoA as the extender unit. The first reaction condenses 3-oxooctanoyl-CoA and acetyl-CoA to a diketoacyl-CoA 3,5-dioxo-decanoyl-CoA. The second reaction condenses 3,5-dioxo-decanoyl-CoA and acetyl-CoA to a triketoacyl-CoA 3,5,7-trioxododecanoyl-CoA.

Olivetolic acid cyclase OAC converts 3,5,7-trioxodode-canoyl-CoA to olivetolic acid. BktB catalyzes the non-decarboxylative Claisen condensation reaction between hexanoyl-CoA and acetyl-CoA to supply 3-oxoocatonyl-CoA. Hexanoyl-CoA is supplied through β-oxidation reversal pathway composed of BktB, FadB and egTER with acetyl-CoA as the initial primer and extender unit. Acetyl-CoA is supplied through glycolysis from a carbon source such as glycerol or sugars. This pathway for olivetolic acid synthesis is shown in FIG. 18.

JST06(DE3) ΔfadE bktB$^{CT5}$ ΔatoB fadB$^{CT5}$ ΔfadA egter$^{CT5}$ @fabI serves as the host strain for the in vivo production of olivetolic acid. JST06(DE3) (MG1655(DE3) ΔldhA ΔpoxB Δpta ΔadhE ΔfadA ΔyciA ΔybgC ΔydiI ΔtesA ΔfadM ΔtesB) (Cheong et al. 2016) is an *E. coli* strain deficient in mixed-acid fermentation pathways due to deletions of genes ldhA, poxB, pta, adhE and frdA, which maximize the supply of acetyl-CoA, and deletion of genes encoding major thioesterases (yciA, ybgC, ydiI, tesA, fadM and tesB), which minimize the hydrolysis of intermediate acyl-CoAs. As such, this strain is selected to maximize the flux of β-oxidation reversal for hexanoyl-CoA supply required for the synthesis of olivetolic acid via polyketoacyl-CoA thiolases.

BktB, FadB and egTER are chromosomally expressed under $p^{CT5}$ promoter with control by cumate. The chromosomal gene atoB is replaced with cumate controlled bktB. For the replacement of atoB with bktB from *Ralstonia eutropha*, a cat-sacB cassette was PCR amplified from genomic DNA with appropriate primers with appended homology for recombination after atoB. This cat-sacB cassette is recombineered into a HME45 strain already harboring a kanamycin resistance marker, cymR repressor gene and hybrid cumate-controlled phage T5 promoter in place of the native atoB promoter whose construction has been described above, resulting in an atoB$^{CT5}$-cat-sacB insertion cassette. bktB is then PCR amplified from with appropriate primers containing homology for recombination, and recombineered into the HME45 strain resulting in a kan-cymR-$P^{CT5}$-bktB construct at the atoB locus after negative selection on sucrose plates. Integration of the cumate-controlled bktB constructs in the chromosome of the target strain is achieved via standard recombineering protocols by using this HME45 derivative strain and selection on LB drug plates (Thomason et al. 2001).

To enable the cumate-inducible chromosomal expression of fadB gene, *E. coli* fadB gene is first PCR amplified using appropriate primers from genomic DNA extracted through Genomic DNA Purification kit (Promega, Fitchburg, Wis.), digested with BglII and NotI (New England Biolabs, Ipswich, Mass.), and ligated by T4 ligase (Invitrogen, Carlsbad, Calif.) into pUCBB-ntH6-eGFP (Vick et al. 2011) that is previously digested with BglII and NotI to produce pUCBB-$P^{CT5}$-fadB. The resulting ligation products are used to transform *E. coli* DH5a (Invitrogen, Carlsbad, Calif.), and positive clones identified by PCR were confirmed by DNA sequencing.

To integrate the cumate-controlled bktB construct into the chromosome of the target strain, first the cumate repressor (cymR), promoter/operator regions ($P^{CT5}$), and respective ORFs are PCR amplified using appropriate primers, as is chloramphenicol drug construct via pKD4 (Datsenko and Wanner, 2000). These respective products are linked together via overlap extension PCR to create a final chromosomal targeting construct. Integration of the cumate-controlled fadB constructs is achieved via standard recombineering protocols by using strain HME45 and selection on LB drug plates (Thomason et al. 2001).

The fadA gene was separately deleted via recombineering in the HME45 derivative harboring the cumate-controlled fadBA construct by replacement of the fadA ORF with a zeocin resistance marker amplified from pKDzeo (Magner et al. 2007). For the creation of the cumate-controlled egTER, the cat gene, cymR repressor gene, hybrid cumate-controlled phage T5 promoter, and egTER gene are PCR amplified from genomic DNA of a strain with egTER seamlessly replacing fadBA at the cumate controlled fadBA locus (see below for details). This product is recombineered into strain HME45 at the end of the fabI locus, selecting on chloramphenicol (12.5 μg/ml) LB plates. Integration is done in a manner to duplicate the last 22 bp of fabI (including stop codon) so as retain an overlapping promoter for the next native downstream gene.

Construction of the strain serving as the PCR template for egTER described above was accomplished by first creating a kan-sacB fusion cassette via overlap extension PCR using pKD4 and genomic DNA, respectively. This kan-sacB cassette was integrated between fadB and fadA of the fadBA$^{CT5}$ strain formerly constructed (Vick et al., 2014) through subsequent recombineering. Seamless replacement of the kan-sacB cassette to create the cat-cymR-$P^{CT5}$-egTER at the fadBA locus was done via recombineering and subsequent sucrose selection with codon optimized egter (Genscript, Piscataway, N.J.) PCR product.

Four polyketoacyl-CoA thiolases were selected and overexpressed: FadAx (AAK18171.1) and PcaF (AAA85138.1) from *Pseudomonas putida*, DcaF (CAG68532.1) from *Acinetobacter* sp. ADP1, and ScFadA (AAL10298.1) from *Streptomyces collinus*. These polyketoacyl-CoA thiolases are selected based on their ability to catalyze the synthesis of TAL in in vitro assays, and they do not cause crosstalk with the overexpressed β-oxidation reversal pathway.

Codon-optimized genes encoding these thiolases are cloned together with the codon-optimized gene encoding OAC into appropriate vectors. These genes are amplified through PCR using appropriate primers to append homology on each end for recombination into the vector backbone with Phusion polymerase (Thermo Scientific, Waltham, Mass.) to serve as the gene insert. Cloning and isolation of confirmed plasmids are conducted as described above.

MOPS minimal medium (Neidhardt et al., 1974) with 125 mM MOPS and $Na_2HPO_4$ in place of $K_2HPO_4$ (2.8 mM), supplemented with 10 g/L tryptone, 5 g/L yeast extract, 100 μM $FeSO_4$, 5 mM calcium pantothenate, 5 mM $(NH_4)_2SO_4$, and 30 mM $NH_4Cl$ is used for fermentations. Antibiotics (50 μg/mL carbenicillin and 50 μg/mL spectinomycin) were included when appropriate. All chemicals are obtained from Fisher Scientific Co. (Pittsburgh, Pa.) and Sigma-Aldrich Co. (St. Louis, Mo.).

Fermentations are conducted in a SixFors multi-fermentation system (Infors HT, Bottmingen, Switzerland) with an air flowrate of 2 N L/hr, independent control of temperature (37° C.), pH (controlled at 7.0 with NaOH and $H_2SO_4$), and stirrer speed (660 rpm). The above fermentation media with 50 g/L glycerol, the inclusion of 5 µM sodium selenite, and 1 µM IPTG are used. Pre-cultures are grown as described above and incubated for 4 hours post-induction. An appropriate amount of this pre-culture is centrifuged, washed twice with fresh media, and used for inoculation with a target initial optical density of 0.05-0.1 (400 mL initial volume).

At various fermentation times samples are taken and 2 mL supernatant is collected through 5000G, 5 min centrifuge in an Optima L-80XP Ultracentrifuge (Beckman-Coulter, Schaumburg, Ill.) of culture and is prepared for GC-FID analysis.

The supernatant aliquots of 2 mL are transferred to 5 mL glass vials (Fisher Scientific Co., Pittsburgh, Pa.) and extraction and derivatization with BSTFA conducted as described above. The quantification of olivetolic acid is performed in a Varian CP-3800 gas chromatograph (Varian Associates, Inc., Palo Alto, Calif.), equipped with a flame ionization detector (GC-FID) and an HP-INNOWax capillary column (0.32 mm internal diameter, 0.50 µm film thickness, 30 m length; Agilent Technologies, Inc., Santa Clara, Calif.), following the method: 100° C. initial column temperature, 15° C./min to 300° C., and 300° C. held for 8 min. Helium (1 mL/min, Matheson Tri-Gas, Longmont, Colo.) is used as the carrier gas. The injector and detector are maintained at 280 and 300° C., respectively. A 1 µL sample is injected in splitless injection mode.

(Prophetic) In Vivo Synthesis of Cannabigerolic Acid (CBGA)

The purpose of this experiment is to clone and express polyketoacyl-CoA thiolases along with olivetolic acid cyclase OAC (AFN42527.1) and from *Cannabis sativa* and aromatic prenyltransferases in an *Escherichia coli* strain already overexpressing ketoacyl-CoA thiolase BktB (AAC38322.1) from *Ralstonia eutropha*, 3-hydroxyacyl-CoA dehydrogenase and enoyl-CoA hydratase multifunctional enzyme FadB from *E. coli* (NP_418288.1) and egTER (Q5EU90.1) for in vivo microbial synthesis of cannabigerolic acid (CBGA). Note that BktB has the three thiolase activities: 1) ketoacyl-CoA thiolase; 2) acetoacetyl-CoA thiolase; and 3) polyketoacyl-CoA thiolase. In this specific example, we are using BktB for its ketoacyl-CoA thiolase activity.

Polyketoacyl-CoA thiolase catalyzes two sequential non-decarboxylative Claisen condensation reactions with 3-oxooctanoyl-CoA as the initial primer and acetyl-CoA as the extender unit. The first reaction condenses 3-oxooctanoyl-CoA and acetyl-CoA to a diketoacyl-CoA 3,5-dioxodecanoyl-CoA. The second reaction condenses 3,5-dioxodecanoyl-CoA and acetyl-CoA to a triketoacyl-CoA 3,5,7-trioxododecanoyl-CoA. Olivetolic acid cyclase OAC converts 3,5,7-trioxododecanoyl-CoA to olivetolic acid. BktB catalyzes the non-decarboxylative Claisen condensation reaction between hexanoyl-CoA and acetyl-CoA to supply 3-oxoocatonyl-CoA.

Aromatic prenyltransferase transfers geranyl group from geranyl pyrophosphate to olivetolic acid to generate cannabigerolic acid. Hexanoyl-CoA is supplied through β-oxidation reversal pathway composed of BktB, FadB and egTer with acetyl-CoA as the initial primer and extender unit. Geranyl pyrophosphate can be supplied through endogenous pathway composed of methylerythritol phosphate pathway and the reaction of geranyl pyrophosphate synthase. Acetyl-CoA is supplied through glycolysis the carbon source as such glycerol or sugars. This pathway for cannabigerolic acid synthesis is shown in FIG. 19A-B.

JST06(DE3) ΔfadE bktB$^{CT5}$ ΔatoB fadB$^{CT5}$ ΔfadA egter$^{CT5}$ @fabI serves as the host strain for the in vivo production of cannabigerolic acid. JST06(DE3) (MG1655 (DE3) ΔldhA ΔpoxB Δpta ΔadhE ΔfadA ΔyciA ΔybgC ΔydiI ΔtesA ΔfadM ΔtesB) (Cheong et al. 2016) is an *E. coli* strain deficient in mixed-acid fermentation pathways due to deletions of genes ldhA, poxB, pta, adhE and frdA, which maximize the supply of acetyl-CoA, and deletions of genes encoding major thioesterases (yciA, ybgC, ydiI, tesA, fadM and tesB), which minimize the hydrolysis of intermediate acyl-CoAs. As such, this strain is selected to maximize the flux of β-oxidation reversal for hexanoyl-CoA supply required for the synthesis of olivetolic acid via polyketoacyl-CoA thiolases. Construction of this strain is described above.

Four polyketoacyl-CoA thiolases were selected and overexpressed: FadAx (AAK18171.1) and PcaF (AAA85138.1) from *Pseudomonas putida*, DcaF (CAG68532.1) from *Acinetobacter* sp. ADP1, and ScFadA (AAL10298.1) from *Streptomyces collinus*. These polyketoacyl-CoA thiolases are chosen because they showed the ability to catalyze the synthesis of TAL in in vitro assays and they do not cause crosstalk with the overexpressed β-oxidation reversal pathway.

Enzymes with potential aromatic prenyltransferase activity include *Cannabis sativa* CsPT1 (sequence available in U.S. Pat. No. 8,884,100), *Humulus lupulus* H1PT (AJD80255.1), *E. coli* UbiA (NP_418464.1), *Saccharomyces cerevisiae* Coq2 (AAA34507.1), *Lithospermum erythrorhizon* LePGT-1 (BAB84122.1), *Lithospermum erythrorhizon* LePGT-2 (BAB84123.1) and other homologs and mutants. Genes encoding these polyketoacyl-CoA thiolases and aromatic prenyltransferases are cloned together with the gene encoding OAC into appropriate vectors through cloning and isolation procedures described above.

Fermentations are conducted in a SixFors multi-fermentation system (Infors HT, Bottmingen, Switzerland) with an air flowrate of 2 N L/hr, independent control of temperature (37° C.), pH (controlled at 7.0 with NaOH and $H_2SO_4$), and stirrer speed (660 rpm). The above described MOPS fermentation media with 50 g/L glycerol, the inclusion of 5 µM sodium selenite, and 1 µM IPTG are used. Pre-culture and inoculation procedures are as described above.

At various fermentation times samples are taken and 2 mL supernatant is collected through 5000G, 5 min centrifuge in an Optima L-80XP Ultracentrifuge (Beckman-Coulter, Schaumburg, Ill.) of culture and is prepared for GC-FID analysis.

The supernatant aliquots of 2 mL are transferred to 5 mL glass vials (Fisher Scientific Co., Pittsburgh, Pa.) and extraction and derivatization with BSTFA conducted as described above.

The quantification of cannabigerolic acid is performed in a Varian CP-3800 gas chromatograph (Varian Associates, Inc., Palo Alto, Calif.), equipped with a flame ionization detector (GC-FID) and an HP-INNOWax capillary column (0.32 mm internal diameter, 0.50 µm film thickness, 30 m length; Agilent Technologies, Inc., Santa Clara, Calif.), following the method: 200° C. held for 1 min, 30° C./min to 300° C., and 300° C. held for 5 min. Helium (1.2 mL/min, Matheson Tri-Gas, Longmont, Colo.) is used as the carrier gas. The injector and detector are maintained at 290 and 300° C., respectively. A 1 µL sample is injected in splitless injection mode.

(Prophetic) In Vivo Synthesis of Orsellinic Acid

The purpose of this experiment is to clone and express polyketoacyl-CoA thiolases in an *Escherichia coli* strain already overexpressing acetoacetyl-CoA thiolase AtoB (NP_416728.1) for in vivo microbial synthesis of orsellinic acid. Polyketoacyl-CoA thiolase catalyzes two sequential non-decarboxylative Claisen condensation reactions with acetoacetyl-CoA as the initial primer and acetyl-CoA as the extender unit, yielding a triketoacyl-CoA, which is then spontaneously cyclized into orsellinic acid. Acetoacetyl-CoA is supplied through AtoB-catalyzed non-decarboxylative Claisen condensation between two acetyl-CoAs. Acetyl-CoA is supplied through glycolysis from a carbon source such as glycerol or sugars. This pathway for orsellinic acid synthesis is shown in FIG. 20.

JST06(DE3) atoB$^{CT5}$ serves as the host strain for the in vivo production of orsellinic acid. JST06(DE3) (MG1655 (DE3) ΔldhA ΔpoxB Δpta ΔadhE ΔfrdA ΔyciA ΔybgC ΔydiI ΔtesA ΔfadM ΔtesB) (Cheong et al. 2016) is an *E. coli* strain deficient in mixed-acid fermentation pathways due to deletions of genes ldhA, poxB, pta, adhE and frdA, which maximize the supply of acetyl-CoA, and deletions of genes encoding major thioesterases (yciA, ybgC, ydiI, tesA, fadM and tesB), which minimize the hydrolysis of acetyl-CoA and acetoacetyl-CoA. The genotype atoB$^{CT5}$ refers to chromosomal atoB gene under the p$^{CT5}$ promoter for controlled induction by cumate. Construction of this strain is described above.

Five polyketoacyl-CoA thiolases are selected and overexpressed in JST06(DE3) atoB$^{CT5}$ strain: FadAx (AAK18171.1) and PcaF (AAA85138.1) from *Pseudomonas putida*, DcaF (CAG68532.1) from *Acinetobacter* sp. ADP1, BktB (AAC38322.1) from *Ralstonia eutropha* and ScFadA (AAL10298.1) from *Streptomyces collinus*. These polyketoacyl-CoA thiolases are selected based on their ability to catalyze the synthesis of TAL in in vitro assays. Codon-optimized genes encoding these thiolases are cloned into appropriate vectors as described above.

Fermentations are performed using the above described MOPS media in 25 mL Pyrex Erlenmeyer flasks or Six-Fors fermentation system as described above with supernatant samples obtained at various times obtained through 5000G, 5 min centrifuge in an Optima L-80XP Ultracentrifuge (Beckman-Coulter, Schaumburg, Ill.) of 2 mL culture is prepared for GC-FID analysis.

The supernatant aliquots of 2 mL are transferred to 5 mL glass vials (Fisher Scientific Co., Pittsburgh, Pa.) and extraction and derivatization with BSTFA conducted as described above.

The quantification of orsellinic acid is performed in a Varian CP-3800 gas chromatograph (Varian Associates, Inc., Palo Alto, Calif.), equipped with a flame ionization detector (GC-FID) and an HP-INNOWax capillary column (0.32 mm internal diameter, 0.50 μm film thickness, 30 m length; Agilent Technologies, Inc., Santa Clara, Calif.), following the method: 100° C. initial column temperature, 15° C./min to 300° C., and 300° C. held for 8 min. Helium (1 mL/min, Matheson Tri-Gas, Longmont, Colo.) is used as the carrier gas. The injector and detector are maintained at 280 and 300° C., respectively. A 1 μL sample is injected in splitless injection mode.

(Prophetic) In Vivo Synthesis

The purpose of this experiment is to clone and express polyketoacyl-CoA thiolases, 3-OH-polyketoacyl-CoA dehydrogenases and polyketoenoyl-CoA hydratases in an *Escherichia coli* strain already overexpressing acetoacetyl-CoA thiolase AtoB (NP_416728.1) for in vivo microbial synthesis of 6-methylsalicylic acid. Polyketoacyl-CoA thiolase catalyzes non-decarboxylative Claisen condensation reaction with acetoacetyl-CoA as the primer and acetyl-CoA as the extender unit, yielding a diketoacyl-CoA. Sequential β-reduction reactions catalyzed by 3-OH-polyketoacyl-CoA dehydrogenase and polyketoenoyl-CoA hydratase convert diketoacyl-CoA to a 5-ketoenoyl-CoA. Polyketoacyl-CoA thiolase then catalyzes non-decarboxylative Claisen condensation reaction with 5-ketoenoyl-CoA as the primer and acetyl-CoA as the extender unit, and the condensation product is then spontaneously cyclized into 6-methylsalicylic acid. Acetoacetyl-CoA is supplied through AtoB-catalyzed non-decarboxylative Claisen condensation between two acetyl-CoAs. Acetyl-CoA is supplied through glycolysis from a carbon source such as glycerol or sugars. This pathway for 6-methylsalicylic acid synthesis is shown in FIG. 21A-B.

JST06(DE3) atoB$^{CT5}$ serves as the host strain for the in vivo production of 6-methylsalicylic acid. JST06(DE3) (MG1655(DE3) ΔldhA ΔpoxB Δpta ΔadhE ΔfrdA ΔyciA ΔybgC ΔydiI ΔtesA ΔfadM ΔtesB) (Cheong et al. 2016) is an *E. coli* strain deficient in mixed-acid fermentation pathways due to deletions of genes ldhA, poxB, pta, adhE and frdA, which maximize the supply of acetyl-CoA, and deletions of genes encoding major thioesterases (yciA, ybgC, ydiI, tesA, fadM and tesB), which minimize the hydrolysis of acetyl-CoA and acetoacetyl-CoA. The genotype atoB$^{CT5}$ refers to chromosomal atoB gene under the p$^{CT5}$ promoter for controlled induction by cumate. Construction of this strain is as described above.

Five polyketoacyl-CoA thiolases are selected and overexpressed in JST06(DE3) atoB$^{CT5}$ strain: FadAx (AAK18171.1) and PcaF (AAA85138.1) from *Pseudomonas putida*, DcaF (CAG68532.1) from *Acinetobacter* sp. ADP1, BktB (AAC38322.1) from *Ralstonia eutropha* and ScFadA (AAL10298.1) from *Streptomyces collinus*.

The candidates of 3-OH-polyketoacyl-CoA dehydrogenases include *E. coli* FabG (NP_415611.1), *E. coli* FadB (NP_418288.1), *E. coli* FadJ (NP_416843.1), *E. coli* PaaH (NP_415913.1), *Pseudomonas putida* FadB (AAK18167.2), *P. putida* FadB2x (AAK18170.1), *Acinetobacter* sp. ADP1 DcaH (CAG68533.1), *Ralstonia eutrophus* PhaB (P14697.1), *Clostridium acetobutylicum* Hbd (AAA95971.1) and other homologs and mutants.

The candidates of polyketoenoyl-CoA hydratases include *E. coli* FabA (NP_415474.1), *E. coli* FabZ (NP_414722.1), *E. coli* FadB (NP_418288.1), *E. coli* FadJ (NP_416843.1), *E. coli* PaaF (NP_415911.1), *P. putida* FadB (AAK18167.2), *P. putida* FadB1x (AAK181730.1), *Acinetobacter* sp. ADP1 DcaE (CAG68535.1), *Clostridium acetobutylicum* Crt (AAA95967.1), *Aeromonas caviae* PhaJ (032472.1) and other homologs and mutants.

Genes encoding these polyketoacyl-CoA thiolases, 3-OH-polyketoacyl-CoA dehydrogenases and polyketoenoyl-CoA hydratases are cloned together into appropriate vectors. Genes from *E. coli* are amplified from genomic DNA extracted through Genomic DNA Purification kit (Promega, Fitchburg, Wis.), and genes from other organisms are amplified from gene product synthesized by either GeneArt (Life Technologies, Carlsbad, Calif., USA) or GenScript (Piscataway, N.J.) with codon-optimization. These genes are amplified through PCR using appropriate primers to append homology on each end for recombination into the vector backbone with Phusion polymerase (Thermo Scientific, Waltham, Mass.) to serve as the gene insert. Plasmids are linearized by the appropriate restriction enzymes (New England Biolabs, Ipswich, Mass.) and recombined with the gene inserts using the In-Fusion HD Eco-Dry Cloning system (Clontech laboratories, Mountain View, Calif.). The mixture is subsequently transformed into Stellar competent cells (Clontech laboratories, Mountain View, Calif.). Transformants that grow on solid media (LB+Agar) supplemented with the appropriate antibiotic are isolated and screened for the gene insert by PCR. Plasmid from verified transformants are isolated and the sequence of the gene insert is further confirmed by DNA sequencing (Lone Star Labs, Houston, Tex.). The sequence confirmed plasmids are then introduced to competent host strain cells.

Fermentations are performed using the above described MOPS media in 25 mL Pyrex Erlenmeyer flasks or Six-Fors fermentation system as described above with supernatant samples obtained at various times obtained through 5000G, 5 min centrifuge in an Optima L-80XP Ultracentrifuge (Beckman-Coulter, Schaumburg, Ill.) of 2 mL culture is prepared for GC-FID analysis.

The supernatant aliquots of 2 mL are transferred to 5 mL glass vials (Fisher Scientific Co., Pittsburgh, Pa.) and extraction and derivatization with BSTFA conducted as described above.

The quantification of 6-methylsalicylic acid is performed in a Varian CP-3800 gas chromatograph (Varian Associates, Inc., Palo Alto, Calif.), equipped with a flame ionization detector (GC-FID) and an HP-INNOWax capillary column (0.32 mm internal diameter, 0.50 µm film thickness, 30 m length; Agilent Technologies, Inc., Santa Clara, Calif.), following the method: 100° C. initial column temperature, 15° C./min to 300° C., and 300° C. held for 8 min. Helium (1 mL/min, Matheson Tri-Gas, Longmont, Colo.) is used as the carrier gas. The injector and detector are maintained at 280 and 300° C., respectively. A 1 µL sample is injected in splitless injection mode.

(Prophetic) Identification of Polyketoacyl-CoA Thiolases

The purpose of this experiment is to identify additional polyketoacyl-CoA thiolases capable of the non-decarboxylative Claisen condensation between a ketoacyl-CoA or a polyketoacyl-CoA, which serves as the primer, and an acyl-CoA serving as the extender unit to form a polyketoacyl-CoA. The identification is through measuring the presence of polyketides, like TAL, dehydroacetic acid, olivetolic acid, orsellinic acid and 6-methylsalicylic acid, derived from the polyketoacyl-CoA generated through polyketoacyl-CoA thiolase-catalyzed non-decarboxylative Claisen condensation reactions.

A library of potential polyketoacyl-CoA thiolases can be generated through expression of synthesized genes encoding thiolases based on sequences from databases like KEGG (genome.jp/kegg), MetaCyc (metacyc.org) and NCBI Protein Database (ncbi.nlm.nih.gov/protein). In MetaCyc, around 100 thiolases are listed; in KEGG, around 1,000 thiolases are listed; in NCBI Protein Database, more than 100,000 thiolases are listed. Genes are synthesized by either GeneArt (Life Technologies, Carlsbad, Calif., USA) or GenScript (Piscataway, N.J., USA) with option of codon-optimization. A thiolase library can also be a library of mutants of a certain thiolase generated through methods selected from error prone PCR random mutagenesis with usage of GeneMorph II Random Mutagenesis Kit (Agilent Technologies, Inc., Santa Clara, Calif.), site-specific saturation mutagenesis of certain sites of the gene encoding the thiolase by QuikChange Multi Site-Directed Mutagenesis Kit (Agilent Technologies, Inc., Santa Clara, Calif., USA) and DNA shuffling of the gene encoding thiolase by JBS DNA-Shuffling Kit (Jena Bioscience GmbH, Jena, Germany).

For expression of members of the thiolase library, genes encoding thiolase members are cloned into appropriate vectors with expression of a His-tag. These genes are amplified from their vectors in the library through PCR using appropriate primers to append homology on each end for recombination into the vector backbone with Phusion polymerase (Thermo Scientific, Waltham, Mass.) to serve as the gene insert.

Plasmids are linearized by the appropriate restriction enzymes (New England Biolabs, Ipswich, Mass., USA) and recombined with the gene inserts using the In-Fusion HD Eco-Dry Cloning system (Clontech laboratories, Mountain View, Calif., USA). The mixture is subsequently transformed into Stellar competent cells (Clontech laboratories, Mountain View, Calif., USA). Transformants that grow on solid media (LB+Agar) supplemented with the appropriate antibiotic are isolated and screened for the gene insert by PCR. Plasmids from verified transformants are isolated and the sequence of the gene insert is further confirmed by DNA sequencing (Lone Star Labs, Houston, Tex., USA). The sequence confirmed plasmids are then introduced to competent host strain cells.

All molecular biology techniques are performed with standard methods (Miller, 1972; Sambrook et al., 2001) or by manufacturer protocol. Strains are kept in glycerol stocks at −80° C. Plates are prepared using LB medium containing 1.5% agar, and appropriate antibiotics are included at the following concentrations: ampicillin (100 µg/mL), kanamycin (50 µg/mL), spectinomycin (50 µg/mL) and chloramphenicol (12.5 µg/mL).

The target polyketide product to identify can be produced in vitro by purified query thiolases exhibiting polyketoacyl-CoA thiolase activity. To express the query thiolases, cultures can be grown in 25 mL of LB media in 125 mL flasks (Wheaton Industries, Inc., Millville, N.J.) at 37° C. A single colony of the desired strain is cultivated overnight (14-16 hrs) in 10 mL of LB medium in baffled flasks (Wheaton Industries, Inc., Millville, N.J.) with appropriate antibiotics and used as the inoculum (1 mL). The cells are induced with appropriate inducer at an OD550~0.6.

After post-induction growth of ASKA strains for 4 hr, or 16 hr for other strains, the cells are collected and washed twice by 9 g/L sodium chloride solution. Cells are then re-suspended in lysis buffer (50 mM $NaH_2PO_4$, 300 mM NaCl, 10 mM imidazole, pH 8.0) to an OD~40. After re-suspension, the cells are disrupted using glass beads and then centrifuged at 4° C., 13000G, 10 min in an Optima L-80XP Ultracentrifuge (Beckman-Coulter, Schaumburg, Ill.). The resultant supernatant is the crude enzyme extract.

The His-tagged enzymes are then purified from crude extract by using Ni-NTA spin kit (Qiagen, Valencia, Calif.). The crude extracts are centrifuged (270G, 5 min) in spin columns, which have been equilibrated with lysis buffer and then washed twice by wash buffer (50 mM $NaH_2PO_4$, 300 mM NaCl, 20 mM imidazole, pH 8.0). After washing, the enzyme is eluted twice in elution buffer (50 mM $NaH_2PO_4$, 300 mM NaCl, 500 mM imidazole, pH 8.0). Both washing and elution steps are centrifuged at 890 g for 2 min.

The purified enzyme extracts are then further concentrated and dialyzed through Amicon® Ultra 10K Device (Millipore, Billerica, Mass.). The enzymes are first filtered by centrifugation at 4° C., 14000G, 10 min, and then washed with 100 mM potassium phosphate, pH 7 buffer under the same centrifugation conditions. Finally, the concentrated and dialyzed enzymes are recovered through 4° C., 1000G, 2 min centrifugation.

The protein concentration is established using the Bradford Reagent (Thermo Scientific, Waltham, Mass.) using BSA as the protein standard. SDS-PAGE monitor of purified proteins is performed through XCell SureLock™ Mini-cell system (Invitrogen, Carlsbad, Calif.) with gels (12% acrylamide resolving gel and 4% acrylamide stacking gel) prepared through SureLock™ Mini-cell system (Invitrogen, Carlsbad, Calif.). The composition of the running buffer for SDS-PAGE was 3 g/L tris base, 14.4 g/L glycine and 1 g/L SDS in water.

The reaction system of in vitro non-decarboxylative Claisen condensation consists of a solution containing appropriate buffer, co-factors, and substrates, such as one containing 100 mM potassium phosphate pH 7, 3 mM EDTA, 1 mM primer CoA thioester, 1 mM extender unit thioester and certain amount of purified query thiolase. Inclusion of additional enzymes, such as thioesterases and olivetolic acid cyclase, can be included to catalyze conversion of polyketoacyl-CoA generated from the non-decarboxylative Claisen condensation to the target polyketide in the reaction system. These additional enzymes are cloned, expressed and purified in same ways as query thiolase, which are described above. The reaction can be performed in a centrifuge tube, a spectroscopy cuvette or a 96-well plate.

The identification of the target polyketide generated in in vitro reaction can be performed by monitoring the increase of its absorbance of certain wavelength, like 298 nm for TAL and 312 nm for dehydroacetic acid, in a Synergy HT plate reader (BioTek Instruments, Inc., Winooski, Vt.) at 25° C. or in a Biomate 5 Spectrophotometer (Thermo Scientific, Waltham, Mass.).

The identification of the target polyketide generated in in vitro reaction can also be performed through GC-FID using appropriate extraction, derivatization, and GC methods. One such example includes the in vitro reaction samples being transferred to 5 mL glass vials (Fisher Scientific Co., Pittsburgh, Pa.), supplemented with 2 mg of 4-pentylbenzoic acid as internal standard, and extracted with 2 mL of hexane. 80 μL of 50% $H_2SO_4$ and 340 μL of 30% NaCl solution are also added for pH and ionic strength adjustment, respectively. Vials are tightly closed, vortexed for 30 s, and mixed in a Glas-Col rotator (Glas-Col, Terre Haute, Ind.) at 60 rpm for 2 h. Samples are then vortexed again for 30 s and centrifuged at 8000 rpm at 4° C. for 1 min. Aliquots of 1.5 mL of the organic layer were transferred to 2 mL borosilicate glass vials with PTFE/silicone screw caps (Fisher Scientific Co., Pittsburgh, Pa.) and mixed with 100 μL of pyridine and 100 μL of BSTFA (N,O-bis(trimethyl silyl)trifluoroacetamide).

Samples are incubated in sealed vials at 70° C. for 60 min using an AccuBlock Digital Dry Bath (LabNet, Woodbridge, N.J.), and silylated samples are analyzed via GC-FID quantification analysis. The GC-FID quantification analysis is performed in a Varian CP-3800 gas chromatograph (Varian Associates, Inc., Palo Alto, Calif.), equipped with a flame ionization detector (GC-FID) and an HP-INNOWax capillary column (0.32 mm internal diameter, 0.50 μm film thickness, 30 m length; Agilent Technologies, Inc., Santa Clara, Calif.), following the method: 200° C. held for 1 min, 30° C./min to 300° C., and 300° C. held for 5 min. Helium (1.2 mL/min, Matheson Tri-Gas, Longmont, Colo.) is used as the carrier gas. The injector and detector are maintained at 290 and 300° C., respectively. A 1 μL sample is injected in splitless injection mode. The GC-FID analysis conditions can be changed depending on the target polyketide.

The identification of the target polyketide generated in in vitro reaction can also be performed via ion-exclusion HPLC using a Shimadzu Prominence SIL 20 system (Shimadzu Scientific Instruments, Inc., Columbia, Md.) equipped with an HPX-87H organic acid column (Bio-Rad, Hercules, Calif.) with operating conditions to optimize peak separation (0.3 mL/min flow rate, 30 mM $H_2SO_4$ mobile phase, column temperature 42° C.). The HPLC analysis conditions can be changed depending on the target polyketide.

The identification of the target polyketide generated in in vitro reactions can also be performed via RP-HPLC using Shimadzu LC-20AD HPLC system with an SPD-20A dual-wavelength UV-vis detector and a Phenomonex Luna C18 column (25 cm×4.6 mm, 5 μm) (Tang et al. 2013). Following elution profile (Xie et al. 2006) can be used: solvent A, 1% (v/v) acetic acid in water; solvent B, 1% (v/v) acetic acid in acetonitrile; gradient: 5% B (0-5 min), 5-15% B (5-18 min), 15-100% B (18-23 min), 100% B (23-30 min); flow rate 1.0 mL/min; wavelength, 300 nm. The RP-HPLC analysis conditions can be changed depending on the target polyketide.

The identification of the target polyketide generated in in vitro reactions can also be performed through one-dimensional proton nuclear magnetic resonance (NMR) spectroscopy. 60 ml of $D_2O$ and 1 ml of 600 mM NMR internal standard TSP [3-(trimethylsilyl) propionic acid-D4, sodium salt] are added to 540 ml of the sample. The resulting solution is then transferred to a 5-mm NMR tube, and one-dimensional proton NMR spectroscopy is performed at 25° C. in a Varian 500-MHz Inova spectrometer equipped with a Penta probe (Varian) using the following parameters: 8,000-Hz sweep width, 2.8-s acquisition time, 256 acquisitions, 6.3 ms pulse width, 1.2-s pulse repetition delay, and pre-saturation for 2 s. The resulting spectrum is analyzed using FELIX 2001 software (Accelrys Software). Peaks are identified by their chemical shifts and J-coupling values, which are obtained in separate experiments in which samples are spiked with metabolite standards (2 mM final concentration).

The target polyketide product to identify can be produced in vivo by expressing the query thiolase in an appropriate host strain that harbors the pathway supplying the primer and the extender unit of the non-decarboxylative Claisen condensation.

One way to identify the target polyketide produced in vivo is through screening the expression of β-galactosidase reporter activated by the mutant AraC biosensor in the response of the target polyketide. The AraC mutant can be acquired through methods selected from error prone PCR random mutagenesis with usage of GeneMorph II Random Mutagenesis Kit (Agilent Technologies, Inc., Santa Clara, Calif.), site-specific saturation mutagenesis of certain sites of the gene encoding the thiolase by QuikChange Multi Site-Directed Mutagenesis Kit (Agilent Technologies) and DNA shuffling of the gene encoding thiolase by JBS DNA-Shuffling Kit (Jena Bioscience GmbH, Jena, Germany) on wild-type AraC. The AraC mutant able to respond on the target polyketide can be screened through Fluorescence-activated cell-sorting (FACS). The genes encoding AraC mutants are cloned into an appropriate plasmid together with the gene encoding GFP in the method as mentioned above. The gfp gene is expressed under $P_{BAD}$ promoter.

The resultant plasmid is introduced to an appropriate host strain for expression of AraC and GFP. Cells are prepared for screening by preculturing overnight in LB medium containing appropriate antibiotics and inducer, followed by dilution to $OD_{600}$=0.2 in the same medium containing appropriate inducer. Induced cells are then grown for 15 h. Fluorescence-activated cell-sorting (FACS) is performed on an inFlux V-GS Cytometry Workbench (Cytopeia) using Spigot software. Fluorescence is excited at 488 nm, and emission is collected using a 531/40 nm filter.

In the first round of screening, the most fluorescent $10^4$ cells are sorted from a total of $10^7$ cells (i.e., the top 0.1% were selected). Flow cytometry analysis is performed on an FC500 flow cytometer (Beckman-Coulter). Flow cytometry of libraries resulting from the first round of positive screening reveals two subpopulations of cells: a majority are highly fluorescent in the absence of any inducer (constitutive or nonspecific phenotypes) and a smaller fraction are significantly less fluorescent in the absence of the target polyketide. The low-fluorescent cells are collected and subjected to another negative screen in the presence of the target polyketide (10 mM) to eliminate clones that are still induced by this polyketide.

This procedure is repeated in a second round of positive and negative FACS screening except the top 1% of cells are selected in the positive screen, yielding at most 100 different mutants induced by d-arabinose and not by 1-arabinose. Ten clones from each library are selected for rescreening and the mutant identified in the most highly induced clones is used as the biosensor. The genes encoding query thiolases are cloned together with the gene encoding β-galactosidase reporter LacZ and AraC mutant biosensor in an appropriate plasmid in the method described as above, with LacZ expressed under $P_{BAD}$ promoter. The resultant plasmid is introduced to an appropriate host strain that harbors the pathway supplying the primer and the extender unit of the non-decarboxylative Claisen condensation. Cells are plated onto LB containing appropriate inducer, carbon source and antibiotics with appropriate amount of X-Gal, and incubated at 37° C. for 20 hours. The cells expressing the thiolase exhibiting the desired polyketoacyl-CoA thiolase activity show darker blue color and can be easily screened.

Another way to identify the target polyketide produced in vivo is growing the cells expressing the query thiolase and analyze the supernatant sample by methods selected from GC-FID, HPLC, RP-HPLC and NMR as described above. MOPS minimal medium (Neidhardt et al., 1974) with 125 mM MOPS and $Na_2HPO_4$ in place of $K_2HPO_4$ (2.8 mM), supplemented with 20 g/L glycerol, 10 g/L tryptone, 5 g/L yeast extract, 100 μM $FeSO_4$, 5 mM calcium pantothenate, 5 mM $(NH_4)_2SO_4$, and 30 mM $NH_4Cl$ is used for fermentations. Antibiotics (50 μg/mL carbenicillin and 50 μg/mL spectinomycin) and additional carbon sources are included when appropriate. All chemicals are obtained from Fisher Scientific Co. (Pittsburgh, Pa.) and Sigma-Aldrich Co. (St. Louis, Mo.). The growth of cells is performed in 25 mL Pyrex Erlenmeyer flasks (narrow mouth/heavy duty rim, Corning Inc., Corning, N.Y.) filled with 20 mL fermentation medium and sealed with foam plugs filling the necks. A single colony of the desired strain is cultivated overnight (14-16 hrs) in LB medium with appropriate antibiotics and used as the inoculum (1%). After inoculation, flasks are incubated in a NBS I24 Benchtop Incubator Shaker (New Brunswick Scientific Co., Inc., Edison, N.J.) at 200 rpm and 37° C. When optical density (550 nm, $OD_{550}$) reached ~0.3-0.5, appropriate concentrations of inducers are added for plasmid and chromosomal expressions. Flasks are then incubated under the same conditions for 48 hours post-induction. After the fermentation, the supernatant obtained through 5000G, 5 min centrifuge in an Optima L-80XP Ultracentrifuge (Beckman-Coulter, Schaumburg, Ill.) of 2 mL culture is prepared for analysis.

The following are incorporated by reference herein in its entirety for all purposes:

Cheong, S., et al., Energy- and carbon-efficient synthesis of functionalized small molecules in bacteria using non-decarboxylative Claisen condensation reactions. Nat Biotech 34, 556-561 (2016).

Choi, K.-H., et al., β-Ketoacyl-Acyl Carrier Protein Synthase III (FabH) Is a Determining Factor in Branched-Chain Fatty Acid Biosynthesis. J. Bacteriol. 182, 365-370 (2000).

Clomburg, J. M., et al., A Synthetic Biology Approach to Engineer a Functional Reversal of the β-Oxidation Cycle. ACS Synthetic Biology 1, 541-554 (2012).

Datsenko, K. A. & Wanner, B. L. One-step inactivation of chromosomal genes in Escherichia coli K-12 using PCR products. Proc. Natl. Acad. Sci. U.S.A 97, 6640-6645 (2000).

Dellomonaco, C., et al., Engineered reversal of the β-oxidation cycle for the synthesis of fuels and chemicals. Nature 476, 355-359 (2011).

Dunn, B. J. & Khosla, C. Engineering the acyltransferase substrate specificity of assembly line polyketide synthases. J. R. Soc. Interface 10 (2013).

Haapalainen, A. M., et al., The thiolase superfamily: condensing enzymes with diverse reaction specificities. Trends in Biochemical Sciences 31, 64-71 (2006).

Heath, R. J. & Rock, C. O. The Claisen condensation in biology. Nat. Prod. Rep. 19, 581-596 (2002).

Jiang, C., et al., Divergent evolution of the thiolase superfamily and chalcone synthase family. Molecular Phylogenetics and Evolution 49, 691-701 (2008).

Kitagawa, M., et al., Complete set of ORF clones of Escherichia coli ASKA library (a complete set of E. coli K-12 ORF archive): unique resources for biological research. DNA Res. 12 291-9 (2005).

Magner, D. B. et al. RecQ Promotes Toxic Recombination in Cells Lacking Recombination Intermediate-Removal Proteins. Mol. Cell 26, 273-286 (2007).

Miller, J. H. Experiments in Molecular Genetics, (Cold Spring Harbor Laboratory Press, 1972)

Moore, B. S. & Hertweck, C. Biosynthesis and attachment of novel bacterial polyketide synthase starter units. Nat. Prod. Rep. 19, 70-99 (2002).

Neidhardt, F. C., et al., Culture medium for enterobacteria J. Bacteriol. 119, 736-747 (1974).

Pfleger, B. F., et al., J. Metabolic engineering strategies for microbial synthesis of oleochemicals. Metab. Eng. 29, 1-11 (2015).

Sambrook, J., et al., Molecular Cloning: A Laboratory Manual, 3rd ed., (Cold Spring Harbor Laboratory Press, 2011).

Studier, F. W. & Moffatt, B. A. Use of bacteriophage T7 RNA polymerase to direct selective high-level expression of cloned genes. J. Mol. Biol. 189, 113-130 (1986).

Tang, S.-Y. et al. Screening for Enhanced Triacetic Acid Lactone Production by Recombinant Escherichia coli Expressing a Designed Triacetic Acid Lactone Reporter. J. Am. Chem. Soc. 135, 10099-10103 (2013).

Tang, S.-Y., et al., AraC Regulatory Protein Mutants with Altered Effector Specificity. J. Am. Chem. Soc. 130, 5267-5271 (2008).

Thomason, L. C., et al., in Current Protocols in Molecular Biology (John Wiley & Sons, Inc., 2001).

Vick, J. E. et al. *Escherichia coli* enoyl-acyl carrier protein reductase (FabI) supports efficient operation of a functional reversal of the β-oxidation cycle. Appl. Environ. Microbiol. 81, 1406-1416 (2015).

Xie, D. et al. Microbial synthesis of triacetic acid lactone. Biotechnol. Bioeng. 93, 727-736 (2006).

61/440,192, filed Feb. 7, 2011, WO2012109176, US20130316413, REVERSE BETA OXIDATION PATHWAY 62/140,628, Mar. 31, 2015, 62/140,628, Mar. 31, 2016 BIOCONVERSION OF SHORT-CHAIN HYDROCARBONS TO FUELS AND CHEMICALS 61/932,057, Jan. 27, 2014, WO2015112988 TYPE II FATTY ACID SYNTHESIS ENZYMES IN REVERSE BETA-OXIDATION 62/069,850 Oct. 29, 2014, PCT/US15/58121, Oct. 29, 2015, SYNTHETIC PATHWAY FOR BIOSYNTHESIS FROM 1-CARBON COMPOUNDS 61/272,117 Aug. 18, 2009; 61/272,057 Aug. 12, 2009; PCT/CA2010/001222 Aug. 4, 2010, AROMATIC PRENYLTRANSFERASE FROM CANNABIS 61/531,911, Sep. 7, 2011; 61/440,192, Feb. 7, 2011, WO2013036812, US20140273110, FUNCTIONALIZED CARBOXYLIC ACIDS AND ALCOHOLS BY REVERSE FATTY ACID OXIDATION sp. pcaF, *P. putida* fadAx, *P. putida* fadA, *Acinetobacter* sp. ADP1 dcaF, or *Ralstonia eutropha* bktB;

c) optionally, C(n+4)-polyketoacyl-CoA→3-OH—C(n+4)-polyketoacyl-CoA;

d) optionally, 3-OH—C(n+4)-polyketoacyl-CoA→C(n+4)-polyketoenoyl-CoA; and e) optionally, C(n+4)-polyketoenoyl-CoA→C(n+4)-α,β-saturated-polyketoacyl-CoA;

f) iterations of at least one of the reactions in steps b), c), d), and e) wherein said iterations are achieved by utilizing a product generated in reactions steps b), c), d), and e), respectively, as a substrates for condensation with acetyl-CoA to elongate said product by two carbons and add a beta-keto group; and g) conversion of said product formed in steps b), c), d), e), or a product formed in step f) to a polyketide or a spontaneously rearranged form of said polyketide or a derivative of said polyketide;

wherein n>0 and <30.

2. The method of claim 1, wherein:
step f is catalyzed by a polyketoacyl-CoA thiolase.

3. The method of claim 1, wherein:
step c is catalyzed by a 3-OH-polyketoacyl-CoA dehydrogenase; or
step d is catalyzed by a 3-OH-polyketoacyl-CoA dehydratase; or
step e is catalyzed by a polyketoenoyl-CoA reductase; or

The invention claimed is:

1. A method of making a polyketide, comprising growing a genetically engineered microorganism in a nutrient broth for a time sufficient to produce a polyketide and isolating said polyketide or a spontaneously rearranged form of said polyketide or a derivative of said polyketide, said polyketide selected from triacetic acid lactone, dehydroacetic acid, olivetolic acid, orsellinic acid, or 6-methylsalicylic acid and said derivative of said polyketide is a prenylated aromatic, or a cannabinoid, or dehydroacetic acid, or olivetolic acid, or cannabigerolic acid, or orsellinic acid, or 6-methylsalicylic acid, wherein said microorganism has a polyketide-producing pathway comprising the following substrate(s) to product(s) conversions:

a) C(n)-acyl-CoA+acetyl-CoA→C(n+2)-ketoacyl-CoA catalyzed by a ketoacyl-CoA thiolase encoded by *Streptomyces collinus* fadA, *Rhodococcus opacus* pcaF, *Pseudomonas putida* pcaF, *Streptomyces* sp. pcaF, *P. putida* fadAx, *P. putida* fadA, *Acinetobacter* sp. ADP1 dcaF, or *Ralstonia eutropha* bktB;

b) C(n+2)-ketoacyl-CoA+acetyl-CoA→C(n+4)-polyketoacyl-CoA catalyzed by a polyketoacyl-CoA thiolase encoded by *Streptomyces collinus* fadA, *Rhodococcus opacus* pcaF, *Pseudomonas putida* pcaF, *Streptomyces* step g is catalyzed by a thioesterase or takes place spontaneously.

4. The method of claim 3, wherein said thioesterase is encoded by a gene(s) selected from the group consisting of *E. coli* tesA, *E. coli* tesB, *E. coli* yciA, *E. coli* fadM, *E. coli* ydiI, *E. coli* ybgC, *E. coli* paaI, *Mus musculus* acot8, *Alcanivorax borkumensis* tesB2, *Fibrobacter succinogenes* Fs2108, *Prevotella ruminicola* Pr655, *Prevotella ruminicola* Pr1687, *Lycopersicon hirsutum* glabratum mks2 and homologs with the same catalytic activity.

5. The method of claim 3, wherein said 3-OH-polyketoacyl-CoA dehydrogenase is encoded by a gene(s) selected from the group consisting of *E. coli* fabG, *E. coli* fadB, *E. coli* fadJ, *E. coli* paaH, *P. putida* fadB, *P. putida* fadB2x, *Acinetobacter* sp. ADP1 dcaH, *Ralstonia eutrophus* phaB, *Clostridium acetobutylicum* hbd and homologs with the same catalytic activity.

6. The method of claim 3, wherein said 3-OH-polyketoacyl-CoA dehydratase is encoded by a gene(s) selected from the group consisting of *E. coli* fabA, *E. coli* fabZ, *E. coli* fadB, *E. coli* fadJ, *E. coli* paaF, *P. putida* fadB, *P. putida* fadB1x, *Acinetobacter* sp. ADP1 dcaE, *Clostridium acetobutylicum* crt, *Aeromonas caviae* phaF and homologs with the same catalytic activity.

7. The method of claim 3, wherein said polyenoylacyl-CoA reductase is encoded by a gene(s) selected from the group consisting of *E. coli* fadE, *E. coli* ydiO, *Euglena gracilis* TER, *Treponema denticola* TEA, *Clostridium acetobutylicum* TER, *E. coli* fabI, *Enterococcus faecalis* fabK, *Bacillus subtilis* fabL, *Vibrio cholerea* fabV and homologs with the same catalytic activity.

8. A method, comprising:
a) combining a polyketoacyl-CoA thiolase with acetyl-CoA and an acetoacetyl-CoA primer, or a ketoacyl-CoA primer or a polyketoacyl-CoA primer under conditions sufficient to allow said polyketoacyl-CoA thiolase to perform non-decarboxylative Claisen condensations with said acetyl-CoA and said primer to form a polyketoacyl-CoA product, said polyketoacyl-CoA thiolase encoded by *Streptomyces collinus* fadA, *Rhodococcus opacus* pcaF, *Pseudomonas putida* pcaF, *Streptomyces* sp. pcaF, *P. putida* fadAx, *P. putida* fadA, *Acinetobacter* sp. ADP1 dcaF, or *Ralstonia eutropha* bktB;

b) hydrolyzing said polyketoacyl-CoA product to form a polyketide or a spontaneous rearrangement form of said polyketide and free Co-A; and
c) isolating said polyketide or said spontaneous rearrangement form of said polyketide or a derivative of said polyketide, wherein said derivative of said polyketide is a prenylated aromatic, or a cannabinoid, or dehydroacetic acid, or olivetolic acid, or cannabigerolic acid, or orsellinic acid, or 6-methylsalicylic acid.

9. The method of claim 8, wherein said method is performed in vivo using a genetically engineered microorganism that expresses said polyketoacyl-CoA thiolase.

10. The method of claim 8, wherein said acetyl-CoA is omega functionalized.

11. The method of claim 8, wherein said method is performed in vitro using a purified polyketoacyl-CoA thiolase.

12. The method of claim 1, wherein said microorganism is *Escherichia coli*.

13. The method of claim 8, wherein said microorganism is *Escherichia coli*.

* * * * *

UNITED STATES PATENT AND TRADEMARK OFFICE
CERTIFICATE OF CORRECTION

PATENT NO. : 11,781,120 B2
APPLICATION NO. : 16/930220
DATED : October 10, 2023
INVENTOR(S) : Ramon Gonzalez, Seokjung Cheong and James M. Clomburg It is certified that error appears in the above-identified patent and that said Letters Patent is hereby corrected as shown below:

In the Claims

On Column 53, Line 4, of Claim 7:
'gracilis TER, Treponema denticola TEA, Clostridium'
Should read as:
---gracilis TER, Treponema denticola TER, Clostridium---

Signed and Sealed this
Fifth Day of December, 2023

Katherine Kelly Vidal
*Director of the United States Patent and Trademark Office*